US010500288B2

(12) United States Patent
Chao

(10) Patent No.: US 10,500,288 B2
(45) Date of Patent: Dec. 10, 2019

(54) CYTOTOXIC HEXIM1 PEPTIDES AND USES THEREOF

(71) Applicant: AGENCY FOR SCIENCE, TECHNOLOGY AND RESEARCH, Singapore (SG)

(72) Inventor: Sheng-Hao Chao, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/555,482

(22) PCT Filed: Mar. 3, 2016

(86) PCT No.: PCT/SG2016/050101
§ 371 (c)(1),
(2) Date: Sep. 1, 2017

(87) PCT Pub. No.: WO2016/140624
PCT Pub. Date: Sep. 9, 2016

(65) Prior Publication Data
US 2018/0243441 A1 Aug. 30, 2018

(30) Foreign Application Priority Data

Mar. 4, 2015 (SG) .......................... 10201501642V
Jun. 17, 2015 (SG) .......................... 10201504803T

(51) Int. Cl.
| | | |
|---|---|---|
| A61K 38/04 | (2006.01) | |
| A61K 47/69 | (2017.01) | |
| C07K 14/00 | (2006.01) | |
| C07K 14/47 | (2006.01) | |
| A61K 47/66 | (2017.01) | |
| A61K 47/68 | (2017.01) | |
| C07K 7/08 | (2006.01) | |
| A61K 38/00 | (2006.01) | |
| A61P 3/04 | (2006.01) | |
| A61P 35/00 | (2006.01) | |
| A61K 39/395 | (2006.01) | |
| A61K 45/06 | (2006.01) | |
| A61K 39/00 | (2006.01) | |

(52) U.S. Cl.
CPC .......... *A61K 47/6931* (2017.08); *A61K 38/04* (2013.01); *A61K 47/66* (2017.08); *A61K 47/6851* (2017.08); *C07K 7/08* (2013.01); *C07K 14/00* (2013.01); *C07K 14/4703* (2013.01); *A61K 38/00* (2013.01); *A61K 39/39558* (2013.01); *A61K 45/06* (2013.01); *A61K 2039/572* (2013.01); *A61K 2300/00* (2013.01); *A61P 3/04* (2018.01); *A61P 35/00* (2018.01)

(58) Field of Classification Search
None
See application file for complete search history.

(56) References Cited

U.S. PATENT DOCUMENTS 6,753,418 B2 * 6/2004 Montano ............ C07K 14/4703
435/252.3
8,470,976 B2 * 6/2013 Chook .................. C07K 14/47
530/300

FOREIGN PATENT DOCUMENTS

WO    WO2012129395 A2    9/2012

OTHER PUBLICATIONS

Sioud, Biochemical Pharmacology 84 (2012) 1123-1132 (Year: 2012).*
PCT International Search Report for PCT Counterpart Application No. PCT/SG2016/050101, 6 pgs. dated (May 13, 2016).
PCT Written Opinion for PCT Counterpart Application No. PCT/SG2016/050101, 6 pgs. dated (May 13, 2016).
Bryan Whittmann, et al., "Identification of a novel inhibitor of breast cell growth that is down-regulated by estrogens and decreased in breast tumors," Cancer Res., vol. 63, No. 16, pp. 5151-5158 (Aug. 15, 2003).
Bryan Whitmann, et al., "The breast cell growth inhibitor, estrogen down regulated gene 1, modulates a novel functional interaction between estrogen receptor alpha and transcriptional elongation factor cyclin T1," Oncogene, vol. 24, No. 36, pp. 5576-5586 (May 23, 2005).
Noritada Yoshikawa, et al., "Cardiomyocyte-Specific Overexpression of HEXIM1 Prevents Right Ventricular Hypertrophy in Hypoxia-Induced Pulmonary Hypertension in Mice," PloS One, vol. 7, No. 12, pp. 1-13 (Dec. 31, 2012).
Qiao Jing Lew, et al., "Identification of HEXIM1 as a Positive Regulator of p53," J. Biol Chem, vol. 287, No. 43, pp. 36443-36454 (Sep. 4, 2012).

(Continued)

*Primary Examiner* — Satyanarayana R Gudibande
(74) *Attorney, Agent, or Firm* — Womble Bond Dickinson (US) LLP

(57) ABSTRACT

Disclosed are isolated cytotoxic peptides having similar sequences as the basic region (BR) of Hexamethylene Bisacetamide Inducible Protein 1 (HEXIM1). Preferred embodiments include QLGKKKHRRRPSKKKRHW (SEQ ID No: 3). QLGRRRHRRRPSRRRRHW (SEQ ID No: 4) and QLGKKILAARPSKKKRHW (SEQ ID No: 5). Also encompassed are isolated nucleic acid molecules encoding for the claimed peptides, vectors comprising the isolated nucleic acids, compositions comprising peptides conjugated to cell-targeting or penetrating peptides or antibodies, nucleic acid molecules or vectors expressing conjugates thereof; methods of treating or preventing diseases or conditions, including cancers and obesity as well as a method of eliminating undifferentiated stem cells.

9 Claims, 12 Drawing Sheets

Specification includes a Sequence Listing.

(56) References Cited

OTHER PUBLICATIONS

Meera Gurumurthy, et al., "Nucleophosmin Interacts with HEXIM1 and Regulates RNA Polymerase II Transcription," J Mol Biol., vol. 378, No. 2, pp. 302-317 (Mar. 4, 2008).
Joanne Lau, et al., "Ubiquitination of HEXIM1 by HDM2," Cell Cycle, Vo. 8, No. 14, pp. 2247-2254 (Jul. 15, 2009).
Shu Hui Neo, et al., "Use of a novel cytotoxic HEXIM1 peptide in the directed breast cancer therapy," Oncotarget, vol. 7, No. 5, pp. 5483-5494 (Dec. 29, 2015).
Interplay between 7SK snRNA and oppositely charged Regions in HEXIM1 Direct the inhibition of P-TEFb, by Matjaz barboric, Jiri Kohoutek, Jason P Price, Dalibor Blazek, David H Price & B Matija Peterlin; The European Molecular Biology Organization (EMBO) Journal; 2005; pp. 4291-4303.
Inhibition of metastasis by HEXIM1 through effects on cell invasion and angiogenesis, by Ketchart W, Smith KM, Krupka T, Wittmann BM, Hu Y, Rayman PA, Doughman YQ, Albert JM, Bai X, Finke JH, Xu Y, Exner AA, Montano MM; National Institute of Health (NIH) Public Access, Author Manuscript, Oncogene 2013; 26 pages.
Brd4 and HEXIM1: Multiple Roles in P-TEFb Regulation and Cancer, by Ruichuan Chen, Jasper H. N. Yik, Qiao Jing Lew, and Sheng-Hao Chao; BioMed Research International; vol. 2014, Article ID 232870, 11 pages.
HEXIM1, a New Player in the P53 Pathway, by Lew QJ, Chu KL, Chia YL, Cheong N, Chao SH; Cancers (Basel). 2013; pp. 838-356 <www.mdpi.com/journals/cancers>.
P-TEFb, a Cyclin-Dependent Kinase Controlling Elongation by RNA Polymerase II, by David H. Price; Molecular and Cellular Biology; American Society for Microbiology; vol. 20, No. 8; 2000; pp. 2629-2634.
Flavopiridol Inactives P-TEFb and Blocks Most RNA Polymerase II Transcription in Vivo*, by Chao SH1, Price DH; The Journal of Biological Chemistry; American Society for Biochemistry and Molecular Biology, Inc.; 2001; pp. 31793-31799.
A chromatin Landmark and Transcription Initiation at Most Promoters in Human Cells, by Guenther MG, Levine SS, Boyer LA, Jaenisch R, Young RA; Cell 130, 77-88; 2007; pp. 77-88.
HEMIM1 and the Control of Transcription Elongation From Cancer and Inflammation to AIDS and Cardiac Hypertrophy, by Dey A, Chao SH, Lane DP; Landes Bioscience; Cell Cycle 6:15; vol. 6, Issue 15; 2007; pp. 1856-1863.
Multiple C-Terminal Lysine Residues Target p53 for Ubiquitin-Proteasome-Mediated Degradation, by Manuel S. Rodriguez, Joana M. P. Desterro, Sonia Lain, David P. Lane, and Ronald T. Hay; Molecular and Cellular Biology, vol. 20, No. 22; American Society for Microbiology; 2000; pp. 8458-8467.
NPMc+ AML cell line shows differential protein expression and lower sensitivity to DNA-damaging and p53-inducing anticancer compounds, by Qiao Jing Lew,Chuan Hao Tan,Meera Gurumurthy,Kai Ling Chu,Nge Cheong,David P. Lane &Sheng-Hao Chao; Cell Cycle 10:12; Landes Bioscience; Jun. 2011; pp. 1978-1987.
Selective killing of cancer cells by peptide-targeted delivery of an anti-microbial peptide, by Sioud M, Mobergslien A; Biochemical Pharmacology 84; 2012; pp. 1123-1132.
Cancer Research; Amphipathic peptide-based Fusion Peptides and Immunoconjugates for the Targeted Ablation of Prostate Cancer Cells, by Kaushal Rege, Suraj J. Patel, Zaki Megeed and Martin L. Yarmush; American Association for Cancer Research; 2007; pp. 6368-6375.
A mitochondria-Trageting Gold-Peptide Nanoassembly for Enhanced Cancer-Cell Killing, by Ma X, Wang X, Zhou M, Fei H; Advanced Healthcare Materials; 2013; pp. 1638-1643.
Cancer Research; Selective Apoptotic killing of Malignant Hemopoietic Cells by Anitibody-Targeted Delivery of an Amphipathic Peptide, by A J. Marks, M S. Cooper, R J. Anderson, K H. Orchard, G Hale, J M. North, K Ganeshaguru, A J. Steele, A B. Mehta, M W. Lowdell & R. G Wickremasinghe; American Association for Cancer Research; 2005; 65: pp. 2373-2377.
Anti-cancer activity of targeted pro-apoptotic peptides, by H. M Ellerby, W Arap, L M Ellerby, R Kain, R Andrusiak, G Del Rio, S Krajewski, C R Lombardo, R Rao, E Ruoslahti, D E Bredesen & R Pasqualini; Nature America Inc.; vol. 5, No. 9; Sep. 1999; pp. 1032-1038 < https://www.medicine.nature.com/>.
Cancer statistics, 2014, by Siegel R, Ma J, Zou Z, Jernal A.; CA Cancer J Clin; Jan.-Feb. 2014; vol. 64, No. 1; pp. 9-29.
Studies on mechanism of action of anticancer peptides by modulation of hydrophobicity within a defined structural framework, by Huang YB, Wang XF, Wang HY, Liu Y, Chen Y; Therapeutic discovery; Molecular Cancer Therapeutics; American Association for Cancer Research; 2011; pp. 416-427.
Peptides Targeting Caspase Inhibitors*, by Tamm I, Trepel M, Cardó-Vila M, Sun Y, Welsh K, Cabezas E, Swatterthwait A, Arap W, Reed JC, Pasqualini R; The Journal of Biological Chemistry; American Society for Biochemistry and Molecular Biology, Inc., vol. 278, No. 16; 2003; pp. 14401-14405.
A Proapoptotic Peptide for the Treatment of Solid Tumors, by Mai JC, Mi Z, Kim SH, Ng B, Robbins PD; Cancer Research; American Association for Cancer Research 61; 2001; pp. 7709-7712.
Synthetic therapeutic peptides: science and market, by Vlieghe P, Lisowski V, Martinez J, Khrestchatisky M; Drug Discovery Today, vol. 15, Nos. ½; Jan. 2010; pp. 40-56.
Cationic amphiphilic peptides with cancer-selective toxicity, by F Schweizer; European Journal of Pharmacology 625; 2009; pp. 190-194.
Cloning of hexamethylene-bis-acetamide-inducible transcript, HEXIM1, in human vascular smooth muscle cells, by M Kusuhara, K Nagasaki, K Kimura, NMaass, T Manabe, S Ishikawa, M Aikawa, K Miyazaki, K Yamaguchi; Biomedical Research 20 (5); 1999; pp. 273-279.
Flavopiridol Inhibits P-TEFb and Blocks HIV-1 Replication*, by Chao SH, Fujinaga K, Marion JE, Taube R, Sausville EA, Senderowicz AM, Peterlin BM, Price DH; The Journal of Biological Chemistry; vol. 275, No. 37; 2000; pp. 28345-28348.
Binding of the 7SK snRNA turns the HEXIM1 protein into a P-TEFb (CDK9/cyclin T) inhibitor, by Michels AA, Fraldi A, Li Q, Adamson TE, Bonnet F, Nguyen VT, Sedore SC, Price JP, Price DH, Lania L, Bensaude O; European Molecular Biology Organization; 2004; pp. 2608-2619.
Inhibition of P-TEFb (CDK9/Cyclin T) kinase and RNA polymerase II transcription by the coordinated actions of HEXIM1 and 7SK snRNA, by Yik JH1, Chen R, Nishimura R, Jennings JL, Link AJ, Zhou Q; Molecular Cell vol. 12; Oct. 2003; pp. 971-982.
The 3'UTR of HIC mRNA improves the production of recombinant proteins in Chinese hamster ovary cells, by Liu J, Ku SC, Lee J, Young TM, Pe'ery T, Mathews MB, Chao SH; Journal of Biotechnology 139; 2009; pp. 152-155.
Identification of a prominent nuclear protein associated with proliferation of normal and malignant B Cells, by Feuerstein N, Mond JJ; The Journal of Immunology 139; 1987; pp. 1818-1822.
Mapping the functional domains of nucleolar protein B23, by Hingorani K, Szebeni A, Olson MO; The Journal of Biological Chemistry; vol. 275, No. 32; 2000; pp. 24451-24457.
Nucleophosmin and cancer, by Silvia Grisendi, Cristina Mecucci, Brunangelo Falini & Pier Paolo Pandolfi; Nature Reviews Cancer, vol. 6; 2006; pp. 493-505.
Cytoplasmic nucleophosmin in acute myelogenous leukemia with a normal karyotype, by F B, Mecucci C, Tiacci E, A M, RR, Pasqualucci L, La Starza R, Diverio D, Colombo E, Santucci A, Bigerna B, Pacini R, Pucciarini A, et al.; The New England Journal of Medicine; 2007; pp. 254-267.
HEIM1 Induces Differentiation of Human Pluripotent Stem Cells, by V Ding, Q J Lew, K L Chu, S Natarajan, V Rajasegaran, M Gurumurthy, A B. H. Choo, Sheng-Hao Chao; Open Access; PLOS One; 2013; <https://doi.org/10.1371/journal.pone.0072823>.
Restoration of the Growth Suppression Function of mutant p53 by a Synthetic Peptide Derived from the p53 C-terminal Domain, by Selivanova G, Iotsova V, Okan I, Fritsche M, Ström M, Groner B, Grafström RC, Wiman KG; Nature Medicine, vol. 3, No. 6; 1997; pp. 632-638.

(56) References Cited

OTHER PUBLICATIONS

The Design, Synthesis, and Evaluation of Molecules that Enable or Enhance Cellular Uptake: Peptoid Molecular Transporters, by Wender PA, Mitchell DJ, Pattabiraman K, Pelkey ET, Steinman L, Rothbard JB; Proc Natl Acad Sci, vol. 97, No. 24; 2000; pp. 13003-13008.
Apoptosis Inducing, Conformationally Constrained, Dimeric Peptide Analogs of KLA with submicromolar cell penetrating abilities, by Hyun S, Lee S, Kim S, Jang S, Yu J, Lee Y; Biomacromolecules; ACS Publications 2014; pp. 3746-3752.
Morphologic Criteria and Detection of Apoptosis, by Antti Saraste; Hertz; Urban & Vogel; 1999; pp. 189-195.
Overexpression of bcl-2 Protects Prostate Cancer Cells from Apoptosis in Vitro and Confers Resistance to Androgen Depletion in Vivo, by Raffo AJ, Perlman H, Chen MW, Day ML, Streitman JS, Buttyan R; Canccer Research 55; 1995; pp. 4438-4-445.
Expression of Bcl-xl Can Confer a Multidrug Resistance Phenotype by Minn AJ, Rudin CM, Boise LH, Thompson CB; Blood Journal, vol. 86, No. 5; 2017; pp. 1903-1910.
Polycomb Protien EZH2 Supresses Apoptosis by silencing the proapoptotic miR-31, by Zhang Q, Padi SK1, Tindall DJ2, Guo B; Cell Death Disease; NPG; 2014; 7 Pages.
Dual-Targeting Pro-apototic Peptide for Programmed cancer cell death via specific mitochondria damage, by Chen WH, Xu XD, Luo GF, Jia HZ, Lei Q, Cheng SX, Zhuo RX, Zhang XZ; Scientific Reports 3:3468; pp. 1-7.
A Propototic Peptide Conjugated to Penetratin Selectively Inhibits Tumor Cell Growth, by Alves ID, Carré M, Montero MP, Castano S, Lecomte S, Marquant R, Lecorché P, Burlina F, Schatz C, Sagan S, Chassaing G, Braguer D, Lavielle S; Biochimica et Biophysica Acta; 2014; pp. 2087-2098.
Kinetics of Apoptotic Markers in Exogeneously Induced Apoptosis of EL4 Cells, by Jessel R, Haertel S, Socaciu C, Tykhonova S, Diehl HA; J Cell Mol Med, vol. 6, No. 1; 2002; pp. 82-92.
Necrotic Death as a Cell Fate, by Zong WX & Thompson CB; Genes & Development 20; Cold Spring Harbor Laboratory Press; 2006; pp. 1-15.
Necrosis Methods and Protocols, by Kimberly McCall, & Charles Klein; Methods in Molecular Biology, Springer Protocols; Humana Press; 2013; 253 Pages.
Necrosis: A specific Form of Programmed Cell Death?, by Proskuryakov SY, Konoplyannikov AG, Gabai VL; Science Direct, Experimental Cell Research 283; 2003; pp. 1-16.
Targeting the Na+/K+-ATPase $\alpha 1$ Sbunit of Hepatoma HepG2 Cell Line to Induce Apoptosis and Cell Cycle Arresting, by Xu ZW1, Wang FM, Gao MJ, Chen XY, Hu WL, Xu RC; Biol Pharm Bull, vol. 33, No. 5; Pharmaceutical Society of Japan; 2010; pp. 743-751.
Targeted Nanoparticle enhanced Proapoptotic peptide as potential therapy for glioblastoma, by Agemy L, Friedmann-Morvinski D, Kotamraju VR, Roth L, Sugahara KN, Girard OM, Mattrey RF, Verma IM, Ruoslahti E; Proc Natl Acad Sci (PNAS) vol. 108, No. 42; 2011; pp. 17450-17455.
Requirement for p53 and p21 to Sustain G2 Arrest After DNA Damage, by Bunz F, Dutriaux A, Lengauer C, Waldman T, Zhou S, Brown JP, Sedivy JM, Kinzler KW, Vogelstein B; Reports; Science Magazine vol. 282; 1998; pp. 1497-1501.
Human Cytomegalovirus: Glycoproteins Associated with Virions and Dense Bodies, by Mark F. Stinski; American Society for Microbiology; Journal of Virology vol. 19, No. 2; 1976; pp. 594-609.

\* cited by examiner

A
| | | |
|---|---|---|
| p53 (a.a. 370-386) | KSKKGQSTSRHKKLMFK | (SEQ ID NO: 34) |
| HEXIM1 (a.a. 150-161) | K-KKHRRRPS-KK---K | (SEQ ID NO: 35) |
B
| | | |
|---|---|---|
| BR-WT | QLGKKKHRRRPSKKKRHW | (SEQ ID NO: 3) |
| BR-RRR12 | QLGRRRHRRRPSRRRRHW | (SEQ ID NO: 4) |
| BR-ILAA | QLGKKILAARPSKKKRHW | (SEQ ID NO: 5) |
C
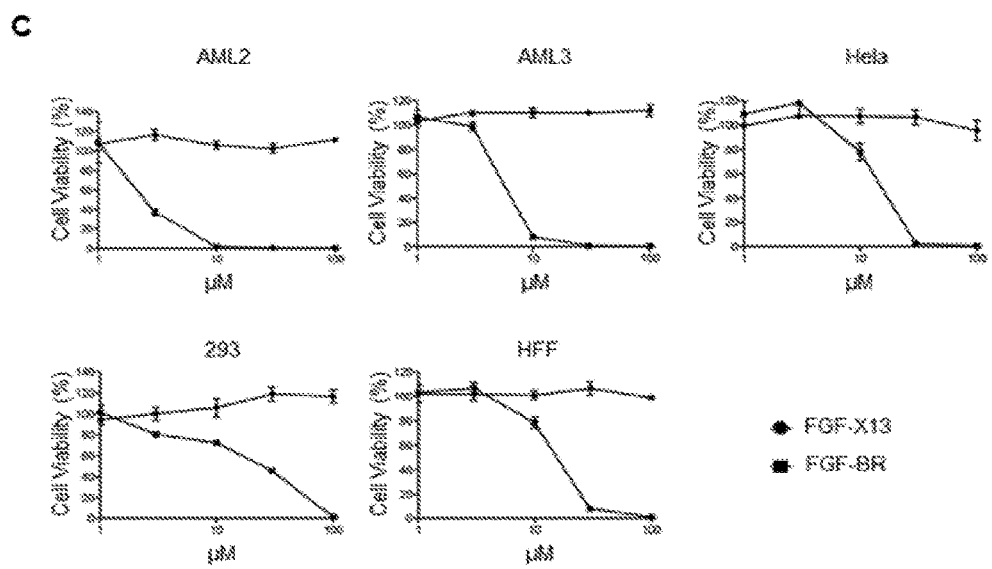
D
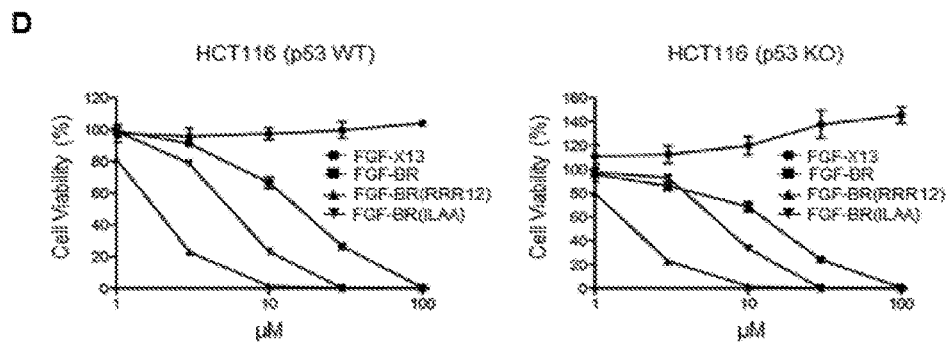
Fig. 1

| Name | Sequence | | Cell Killing Potency |
|---|---|---|---|
| LTV-BR | LTVSPWYGCQQLGKKKHRRRPSKKKRHW | (SEQ ID NO: 15) | ++ |
| LTV-Mut1 | LTVSPWYGCQQLGKKKR------------ | (SEQ ID NO: 22) | - |
| LTV-Mut2 | LTVSPWYGCQQLGKKKHRRRPS-------- | (SEQ ID NO: 23) | - |
| LTV-Mut3 | LTVSPWYGCG------------PSKKKRHW | (SEQ ID NO: 24) | - |
| LTV-Mut4 | LTVSPWYGCG--------HRRRPSKKKRHW | (SEQ ID NO: 25) | + |
| LTV-Mut5 | LTVSPWYGCG--------HRRRPS------ | (SEQ ID NO: 26) | - |

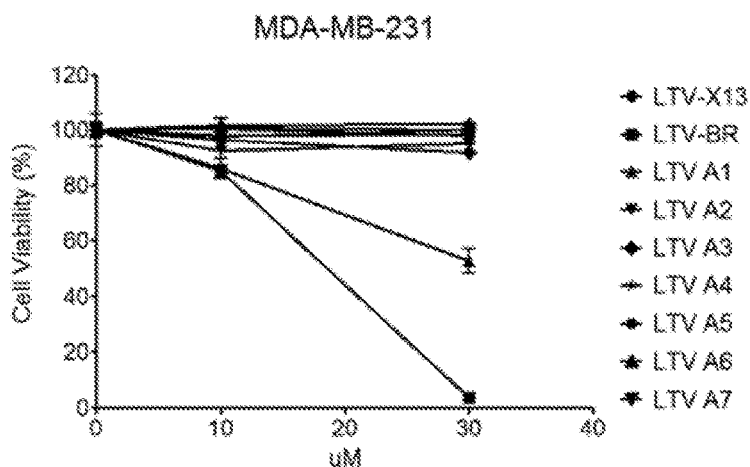

| Name | Sequence | | Cell Killing Potency |
|---|---|---|---|
| LTV-BR | LTVSPWYGCGQLGKKKHRRRPSKKKRW | (SEQ ID NO: 15) | ++ |
| LTV-BR(A1) | LTVSPWYGCGQLGAAAHRRRPSKKKRW | (SEQ ID NO: 27) | + |
| LTV-BR(A2) | LTVSPWYGCGQLGKKKHAAAPSKKKRW | (SEQ ID NO: 28) | - |
| LTV-BR(A3) | LTVSPWYGCGQLGKKKHRRRPSAAAAW | (SEQ ID NO: 29) | - |
| LTV-BR(A4) | LTVSPWYGCGQLGAAAHAAAPSKKKRW | (SEQ ID NO: 30) | - |
| LTV-BR(A5) | LTVSPWYGCGQLGAAAHRRRPSAAARW | (SEQ ID NO: 31) | - |
| LTV-BR(A6) | LTVSPWYGCGQLGKKKHAAAPSAAARW | (SEQ ID NO: 32) | - |
| LTV-BR(A7) | LTVSPWYGCGQLGAAAHAAAPSAAARW | (SEQ ID NO: 33) | - |

Fig. 8

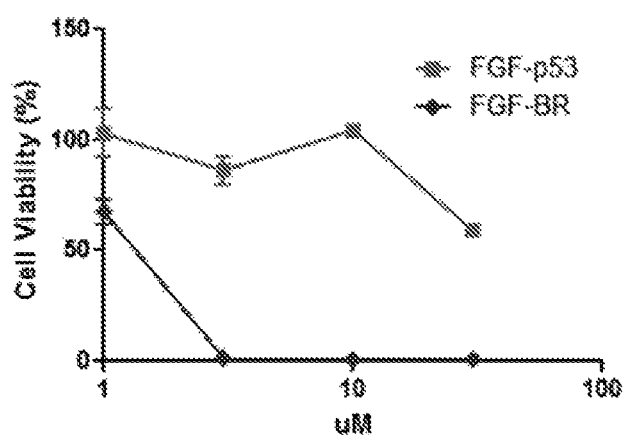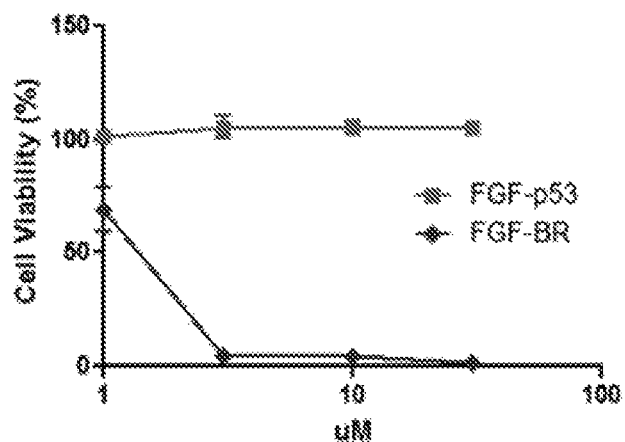
Fig. 11

SEQUENCE LISTING

```
<160> NUMBER OF SEQ ID NOS: 798

<210> SEQ ID NO 1
<211> LENGTH: 359
<212> TYPE: PRT
<213> ORGANISM: Homo sapiens

<400> SEQUENCE: 1

Met Ala Glu Pro Phe Leu Ser Glu Tyr Gln His Gln Pro Gln Thr Ser
1               5                  10                  15

Asn Cys Thr Gly Ala Ala Ala Val Gln Glu Glu Leu Asn Pro Glu Arg
            20                  25                  30

Pro Pro Gly Ala Glu Glu Arg Val Pro Glu Glu Asp Ser Arg Trp Gln
        35                  40                  45

Ser Arg Ala Phe Pro Gln Leu Gly Gly Arg Pro Gly Pro Gly Gly Glu
    50                  55                  60

Gly Ser Leu Glu Ser Gln Pro Pro Leu Gln Thr Gln Ala Cys Pro
65                  70                  75                  80

Glu Ser Ser Cys Leu Arg Glu Gly Glu Lys Gly Gln Asn Gly Asp Asp
            85                  90                  95

Ser Ser Ala Gly Gly Asp Phe Pro Pro Pro Ala Glu Val Glu Pro Thr
        100                 105                 110

Pro Glu Ala Glu Leu Leu Ala Gln Pro Cys His Asp Ser Glu Ala Ser
    115                 120                 125

Lys Leu Gly Ala Pro Ala Ala Gly Gly Glu Glu Glu Trp Gly Gln Gln
    130                 135                 140

Gln Arg Gln Leu Gly Lys Lys Lys His Arg Arg Arg Pro Ser Lys Lys
145                 150                 155                 160

Lys Arg His Trp Lys Pro Tyr Tyr Lys Leu Thr Trp Glu Glu Lys Lys
                165                 170                 175

Lys Phe Asp Glu Lys Gln Ser Leu Arg Ala Ser Arg Ile Arg Ala Glu
            180                 185                 190

Met Phe Ala Lys Gly Gln Pro Val Ala Pro Tyr Asn Thr Thr Gln Phe
        195                 200                 205

Leu Met Asp Asp His Asp Gln Glu Glu Pro Asp Leu Lys Thr Gly Leu
    210                 215                 220

Tyr Ser Lys Arg Ala Ala Ala Lys Ser Asp Asp Thr Ser Asp Asp Asp
225                 230                 235                 240

Phe Met Glu Glu Gly Gly Glu Gly Gly Ser Asp Gly Met Gly
                245                 250                 255

Gly Asp Gly Ser Glu Phe Leu Gln Arg Asp Phe Ser Glu Thr Tyr Glu
            260                 265                 270

Arg Tyr His Thr Glu Ser Leu Gln Asn Met Ser Lys Gln Glu Leu Ile
        275                 280                 285
```

```
Lys Glu Tyr Leu Glu Leu Glu Lys Cys Leu Ser Arg Met Glu Asp Glu
    290                 295                 300

Asn Asn Arg Leu Arg Leu Glu Ser Lys Arg Leu Gly Gly Asp Asp Ala
305                 310                 315                 320

Arg Val Arg Glu Leu Glu Leu Glu Leu Asp Arg Leu Arg Ala Glu Asn
                325                 330                 335

Leu Gln Leu Leu Thr Glu Asn Glu Leu His Arg Gln Gln Glu Arg Ala
            340                 345                 350

Pro Leu Ser Lys Phe Gly Asp
            355
```

```
<210> SEQ ID NO 2
<211> LENGTH: 31
<212> TYPE: PRT
<213> ORGANISM: Homo sapiens

<400> SEQUENCE: 2

Lys Lys Lys His Arg Arg Arg Pro Ser Lys Lys Lys Arg His Trp Lys
1               5                   10                  15

Pro Tyr Tyr Lys Leu Thr Trp Glu Glu Lys Lys Lys Phe Asp Glu
            20                  25                  30
```

```
<210> SEQ ID NO 3
<211> LENGTH: 18
<212> TYPE: PRT
<213> ORGANISM: Homo sapiens

<400> SEQUENCE: 3

Gln Leu Gly Lys Lys His Arg Arg Arg Pro Ser Lys Lys Lys Arg
1               5                   10                  15

His Trp
```

```
<210> SEQ ID NO 4
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 4

Gln Leu Gly Arg Arg Arg His Arg Arg Arg Pro Ser Lys Lys Lys Arg
1               5                   10                  15

His Trp
```

```
<210> SEQ ID NO 5
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 5

Gln Leu Gly Lys Lys Ile Leu Ala Ala Arg Pro Ser Lys Lys Lys Arg
1               5                   10                  15

His Trp
```

```
<210> SEQ ID NO 6
<211> LENGTH: 21
<212> TYPE: PRT
<213> ORGANISM: Artificial Sequence
<220> FEATURE:
<223> OTHER INFORMATION: Synthetic Sequence
```

```
<400> SEQUENCE: 6

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Arg Arg Trp Trp Arg Arg Trp Arg Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 8

Leu Thr Val Ser Pro Trp Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 9

Ile Phe Leu Leu Trp Gln Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 10

Cys Gly Asn Ser Asn Pro Lys Ser Cys
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 11

Ser Val Ser Val Gly Met Lys Pro Ser Pro Arg Pro
1               5                   10

<210> SEQ ID NO 12
<211> LENGTH: 13
<212> TYPE: PRT
<213> ORGANISM: Artificial Sequence
```

```
<220> FEATURE:
<223> OTHER INFORMATION: Synthetic Sequence

<400> SEQUENCE: 12

Met Pro Phe Ser Thr Gly Lys Arg Ile Met Leu Gly Glu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 13

Lys Leu Ala Lys Leu Ala Lys Lys Leu Ala Lys Leu Ala Lys
1               5                   10

<210> SEQ ID NO 14
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 14

Leu Thr Val Ser Pro Trp Tyr Gly Cys Gly Met Pro Phe Ser Thr Gly
1               5                   10                  15

Lys Arg Ile Met Leu Gly Glu
            20

<210> SEQ ID NO 15
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 15

Leu Thr Val Ser Pro Trp Tyr Gly Cys Gly Gln Leu Gly Lys Lys Lys
1               5                   10                  15

His Arg Arg Arg Pro Ser Lys Lys Lys Arg His Trp
            20                  25

<210> SEQ ID NO 16
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 16

Leu Thr Val Ser Pro Trp Tyr Gly Cys Gly Gln Leu Gly Arg Arg Arg
1               5                   10                  15

His Arg Arg Arg Pro Ser Arg Arg Arg Arg His Trp
            20                  25

<210> SEQ ID NO 17
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 17
```

-continued

```
Leu Thr Val Ser Pro Trp Tyr Gly Cys Gly Lys Leu Ala Lys Leu Ala
1               5                   10                  15

Lys Lys Leu Ala Lys Leu Ala Lys
            20

<210> SEQ ID NO 18
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 18

Ala Ala Val Ala Leu Leu Pro Ala Val Leu Leu Ala Leu Leu Ala Pro
1               5                   10                  15

Met Pro Phe Ser Thr Gly Lys Arg Ile Met Leu Gly Glu
            20                  25

<210> SEQ ID NO 19
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 19

Ala Ala Val Ala Leu Leu Pro Ala Val Leu Leu Ala Leu Leu Ala Pro
1               5                   10                  15

Gln Leu Gly Lys Lys Lys His Arg Arg Arg Pro Ser Lys Lys Lys Arg
            20                  25                  30

His Trp

<210> SEQ ID NO 20
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 20

Ala Ala Val Ala Leu Leu Pro Ala Val Leu Leu Ala Leu Leu Ala Pro
1               5                   10                  15

Gln Leu Gly Arg Arg Arg His Arg Arg Arg Pro Ser Arg Arg Arg Arg
            20                  25                  30

His Trp

<210> SEQ ID NO 21
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 21

Ala Ala Val Ala Leu Leu Pro Ala Val Leu Leu Ala Leu Leu Ala Pro
1               5                   10                  15

Gln Leu Gly Lys Lys Ile Leu Ala Ala Arg Pro Ser Lys Lys Lys Arg
            20                  25                  30

His Trp

<210> SEQ ID NO 22
<211> LENGTH: 17
```

<212> TYPE: PRT
<213> ORGANISM: Artificial Sequence
<220> FEATURE:
<223> OTHER INFORMATION: Synthetic Sequence

<400> SEQUENCE: 22

Leu Thr Val Ser Pro Gln Tyr Gly Cys Gly Gln Leu Gly Lys Lys Lys
1               5                   10                  15

His

<210> SEQ ID NO 23
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 23

Leu Thr Val Ser Pro Gln Tyr Gly Cys Gly Gln Leu Gly Lys Lys Lys
1               5                   10                  15

His Arg Arg Arg Pro Ser
            20

<210> SEQ ID NO 24
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 24

Leu Thr Val Ser Pro Gln Tyr Gly Cys Gly Pro Ser Lys Lys Lys Arg
1               5                   10                  15

His Trp

<210> SEQ ID NO 25
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 25

Leu Thr Val Ser Pro Gln Tyr Gly Cys Gly His Arg Arg Arg Pro Ser
1               5                   10                  15

Lys Lys Lys Arg His Trp
            20

<210> SEQ ID NO 26
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 26

Leu Thr Val Ser Pro Gln Tyr Gly Cys Gly His Arg Arg Arg Pro Ser
1               5                   10                  15

<210> SEQ ID NO 27
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 27

Leu Thr Val Ser Pro Gln Tyr Gly Cys Gly Gln Leu Gly Ala Ala Ala
1               5                   10                  15

His Arg Arg Arg Pro Ser Lys Lys Lys Arg His Trp
            20                  25

<210> SEQ ID NO 28
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 28

Leu Thr Val Ser Pro Gln Tyr Gly Cys Gly Gln Leu Gly Lys Lys Lys
1               5                   10                  15

His Ala Ala Ala Pro Ser Lys Lys Lys Arg His Trp
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 29

Leu Thr Val Ser Pro Gln Tyr Gly Cys Gly Gln Leu Gly Lys Lys Lys
1               5                   10                  15

His Arg Arg Arg Pro Ser Ala Ala Ala Ala His Trp
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 30

Leu Thr Val Ser Pro Gln Tyr Gly Cys Gly Gln Leu Gly Ala Ala Ala
1               5                   10                  15

His Ala Ala Ala Pro Ser Lys Lys Lys Arg His Trp
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 31

Leu Thr Val Ser Pro Gln Tyr Gly Cys Gly Gln Leu Gly Ala Ala Ala
1               5                   10                  15

His Arg Arg Arg Pro Ser Ala Ala Ala Ala His Trp
            20                  25

<210> SEQ ID NO 32
<211> LENGTH: 28
<212> TYPE: PRT
<213> ORGANISM: Artificial Sequence
<220> FEATURE:

<223> OTHER INFORMATION: Synthetic Sequence

<400> SEQUENCE: 32

Leu Thr Val Ser Pro Gln Tyr Gly Cys Gly Gln Leu Gly Lys Lys Lys
1               5                   10                  15
His Ala Ala Ala Pro Ser Ala Ala Ala His Trp
            20                  25

<210> SEQ ID NO 33
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 33

Leu Thr Val Ser Pro Gln Tyr Gly Cys Gly Gln Leu Gly Ala Ala Ala
1               5                   10                  15
His Ala Ala Ala Pro Ser Ala Ala Ala His Trp
            20                  25

<210> SEQ ID NO 34
<211> LENGTH: 17
<212> TYPE: PRT
<213> ORGANISM: Homo sapiens

<400> SEQUENCE: 34

Lys Ser Lys Lys Gly Gln Ser Thr Ser Arg His Lys Lys Leu Met Phe
1               5                   10                  15
Lys

<210> SEQ ID NO 35
<211> LENGTH: 12
<212> TYPE: PRT
<213> ORGANISM: Homo sapiens

<400> SEQUENCE: 35

Lys Lys Lys His Arg Arg Arg Pro Ser Lys Lys Lys
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(6)
<223> OTHER INFORMATION: is any amino acid
<220> FEATURE:
<221> NAME/KEY: MISC_FEATURE
<222> LOCATION: (4)..(6)
<223> OTHER INFORMATION: is positively charged amino acid
<220> FEATURE:
<221> NAME/KEY: MISC_FEATURE
<222> LOCATION: (7)..(7)
<223> OTHER INFORMATION: is H or L
<220> FEATURE:
<221> NAME/KEY: MISC_FEATURE
<222> LOCATION: (8)..(9)
<223> OTHER INFORMATION: is small amino acid
<220> FEATURE:
<221> NAME/KEY: MISC_FEATURE
<222> LOCATION: (8)..(9)
<223> OTHER INFORMATION: is A
<220> FEATURE:
<221> NAME/KEY: MISC_FEATURE

```
<222> LOCATION: (13)..(15)
<223> OTHER INFORMATION: is positively charged amino acid

<400> SEQUENCE: 36

Gln Leu Gly Xaa Xaa Xaa Xaa Xaa Arg Pro Ser Xaa Xaa Xaa Arg
1               5                   10                  15

His Trp

<210> SEQ ID NO 37
<211> LENGTH: 12
<212> TYPE: PRT
<213> ORGANISM: Homo sapiens

<400> SEQUENCE: 37

His Arg Arg Arg Pro Ser Lys Lys Lys Arg His Trp
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 38

Gln Leu Gly Ala Ala Ala His Arg Arg Arg Pro Ser Lys Lys Lys Arg
1               5                   10                  15

His Trp

<210> SEQ ID NO 39
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 39

Cys Lys Gly Gly Arg Ala Lys Asp Cys
1               5

<210> SEQ ID NO 40
<211> LENGTH: 29
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (12)..(29)
<223> OTHER INFORMATION: is D-amino acid

<400> SEQUENCE: 40

Cys Lys Gly Gly Arg Ala Lys Asp Cys Gly Gly Gln Leu Gly Lys Lys
1               5                   10                  15

Lys His Arg Arg Arg Pro Ser Lys Lys Lys Arg His Trp
            20                  25

<210> SEQ ID NO 41
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 41
```

Ala Val Gly Pro Tyr Ser Gly Leu Lys Val Phe Arg
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 42

Ser Pro Leu Ser Lys Gly Ser Thr His Leu Ser Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 43

Thr Asn Lys Pro Val Gln Pro Arg Gln Thr Leu Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 44

Ala Met His Pro Ser Pro Ala Ser Ala Lys Met Asn
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 45

Ala Gly Ala Pro Tyr Arg Asn Thr Asn Ala Gly Thr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 46

Thr Pro Thr Glu Arg Phe Asn Thr His His Val Glu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 47

Gln Ala Gly Asp Glu Lys Glu Trp Leu Gly Pro Lys

<210> SEQ ID NO 48
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 48

Gly Ser Asn Gln Ser Val Arg Tyr Leu Gln Gln Thr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 49

Asn Val Asp Tyr Ala Phe Gly Lys Arg Glu Gln Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 50

Asp Pro Leu Leu His Ser Gln Ala Asp Val Gln Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 51

Leu Pro His Ser Ser Trp Asn Pro Lys Leu Ala Leu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 52

His Gln Val His Ala Lys Pro Leu Asp Leu Met Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 53

Gln Tyr Thr Phe Ser Val Asn Pro Leu Met Arg Ala
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 54

Val Pro His Phe Ser Thr Pro Thr Ser Val Phe Gln
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 55

Asn Tyr Ala Ile Ala Val Val Asn Val Leu Ser His
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 56

Asn Thr Lys Val Pro Asp Pro Thr Ala Arg Leu Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 57

His Gly Ala Ala Trp Gly Thr Arg Thr Gly His Val
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 58

Val Pro Ala Thr Glu Thr Ala Gln Ala Gly His Ala
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 59

Val Glu Tyr His Phe Asn His Thr Met Thr Ala Tyr
1               5                   10

```
<210> SEQ ID NO 60
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 60

Val Gly Gly Glu Ala Trp Ser Ser Pro Thr Asp Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 61

His Ser Asp Gln Val Ala Leu Lys Met Thr Arg Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 62

Gln Pro His Ser Val Ser Val Ser Asp Thr Trp His
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 63

Ser Asn Asn Asp Asn Leu Ala His Arg Val Arg Leu
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 64

Cys Ser Asn Ile Asp Ala Arg Ala Cys
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 65

Cys Asp Pro Ser Arg Gly Lys Asn Cys
1               5
```

```
<210> SEQ ID NO 66
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 66

Cys Pro Ser Asp Leu Lys Asp Ala Cys
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 67

Cys Arg Thr Thr Arg Gly Thr Lys Cys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 68

Cys Arg Met Thr Arg Asn Lys Pro Cys
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 69

Cys Arg Val Ser Arg Gln Asn Lys Cys
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 70

Cys Ala Lys Ile Asp Pro Glu Leu Cys
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 71

Cys Gly Gly Glu Arg Gly Lys Ser Cys
1               5

<210> SEQ ID NO 72
```

```
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 72

Tyr Ser Ile Asn Asp Trp His
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 73

Tyr Ser Phe Asn Ser Trp Met
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 74

Pro Asn Pro Asn Asn Ser Thr
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 75

Tyr Pro Thr Pro Tyr Asp Ile
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 76

Leu Pro Ala Met Pro Asn Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 77

Cys Asn Arg Arg Thr Lys Ala Gly Cys
1               5

<210> SEQ ID NO 78
<211> LENGTH: 7
```

```
<212> TYPE: PRT
<213> ORGANISM: Artificial Sequence
<220> FEATURE:
<223> OTHER INFORMATION: Synthetic Sequence

<400> SEQUENCE: 78

Ser Arg His Asp Leu Asn Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 79

Ser Thr Val Ala Thr Ser Gln
1               5

<210> SEQ ID NO 80
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 80

Gln Arg Leu Gly Asn Gln Trp Ala Val Gly His Leu Met
1               5                   10

<210> SEQ ID NO 81
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 81

Arg Gly Asp Phe
1

<210> SEQ ID NO 82
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 82

Lys Gly Val Ser Leu Ser Tyr Arg
1               5

<210> SEQ ID NO 83
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 83

Gln Phe Pro Pro Lys Leu Thr Asn Asn Ser Met Leu
1               5                   10

<210> SEQ ID NO 84
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 84

Ser Tyr Asp Ile Leu Lys Pro Asn Pro Gln Arg Leu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 85

Ser His Gly Lys Pro Pro Ser Phe Ser Pro Tyr Thr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 86

Leu Leu Ala Asp Thr Thr His His Arg Pro Trp Thr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 87

Cys Thr Pro Ser Pro Pro Phe Ser His Cys
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 88

Cys Pro Asn Gly Arg Cys
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 89

Cys Leu Ser Tyr Tyr Pro Ser Tyr Cys
1               5

<210> SEQ ID NO 90
<211> LENGTH: 6
<212> TYPE: PRT
<213> ORGANISM: Artificial Sequence
```

```
<220> FEATURE:
<223> OTHER INFORMATION: Synthetic Sequence

<400> SEQUENCE: 90

Arg Thr Arg Tyr Glu Asp
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 91

Gly Met Met Tyr Arg Ser
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 92

Arg Trp Arg Thr Asn Phe
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 93

Arg Leu Gln Leu Lys Leu
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 94

Arg Ile Pro Leu Glu Met
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 95

Gln Phe Asp Glu Pro Arg
1               5

<210> SEQ ID NO 96
<211> LENGTH: 6
<212> TYPE: PRT
<213> ORGANISM: Artificial Sequence
<220> FEATURE:
```

```
<223> OTHER INFORMATION: Synthetic Sequence

<400> SEQUENCE: 96

Thr Ser Ala Val Arg Thr
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 97

Gly Leu Trp Gln Gly Pro
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 98

Gln Cys Thr Gly Arg Phe
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 99

Leu Pro Gly Met Met Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 100

Asp Val Gly Thr Thr Glu
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 101

Thr Asp Leu Gly Ala Met
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Sequence
```

<400> SEQUENCE: 102

Asp Ser Asn Ala Glu Ser
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 103

Ile Thr Asp Met Ala Ala
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 104

Trp Arg Pro Cys Glu Ser
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 105

Trp Arg Asn Thr Ile Ala
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 106

Ile Asp Lys Gln Leu Glu
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 107

Phe Met Glu Ile Glu Thr
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 108

His Glu Val Val Ala Gly
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 109

Gly Gly His Thr Arg Gln
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 110

Ile Asn Gly Lys Val Thr
1               5

<210> SEQ ID NO 111
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: is any amino acid

<400> SEQUENCE: 111

Val Pro Trp Xaa Glu Pro Ala Tyr Gln Arg Phe Leu
1               5                   10

<210> SEQ ID NO 112
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 112

Gly Arg Asp Ser
1

<210> SEQ ID NO 113
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 113

Arg Gly Glu Pro Ala Tyr Gln Arg Phe Leu
1               5                   10

<210> SEQ ID NO 114
<211> LENGTH: 10
<212> TYPE: PRT
<213> ORGANISM: Artificial Sequence

```
<220> FEATURE:
<223> OTHER INFORMATION: Synthetic Sequence

<400> SEQUENCE: 114

Arg Gly Asp Pro Ala Tyr Gln Arg Phe Leu
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 115

Trp Xaa Glu Pro Ala Tyr Gln Gly Arg Phe Leu
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 116

Trp Xaa Glu Pro Ala Tyr Asn Gly Arg Phe Leu
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 117

Arg Gly Glu Pro Ala Tyr Gln Gly Arg Phe Leu
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 118

Arg Gly Asp Pro Ala Tyr Gln Gly Arg Phe Leu
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 119

Arg Gly Glu Pro Ala Tyr Asn Gly Arg Phe Leu
```

1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 120

Arg Gly Asp Pro Ala Tyr Asn Gly Arg Phe Leu
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 121

Trp Xaa Glu Pro Ala Tyr Gln Arg Phe Leu
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 122

Ala Xaa Glu Pro Ala Tyr Gln Arg Phe Leu
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 123

Trp Ala Glu Pro Ala Tyr Gln Arg Phe Leu
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 124

Trp Xaa Ala Pro Ala Tyr Gln Arg Phe Leu
1               5                   10

```
<210> SEQ ID NO 125
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 125

Trp Xaa Glu Ala Ala Tyr Gln Arg Phe Leu
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 126

Trp Xaa Glu Pro Ala Ala Gln Arg Phe Leu
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 127

Trp Xaa Glu Pro Ala Tyr Ala Arg Phe Leu
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 128

Trp Xaa Glu Pro Ala Tyr Gln Ala Phe Leu
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid
```

```
<400> SEQUENCE: 129

Trp Xaa Glu Pro Ala Tyr Gln Ala Ala Leu
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 130

Trp Xaa Glu Pro Ala Tyr Gln Ala Phe Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 131

Glu Xaa Glu Pro Ala Tyr Gln Arg Phe Leu
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 132

Leu Xaa Glu Pro Ala Tyr Gln Arg Phe Leu
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 133

Lys Xaa Glu Pro Ala Tyr Gln Arg Phe Leu
1               5                   10

<210> SEQ ID NO 134
<211> LENGTH: 10
<212> TYPE: PRT
<213> ORGANISM: Artificial Sequence
```

```
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 134

Gln Xaa Glu Pro Ala Tyr Gln Arg Phe Leu
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 135

Tyr Xaa Glu Pro Ala Tyr Gln Arg Phe Leu
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 136

Phe Xaa Glu Pro Ala Tyr Gln Arg Phe Leu
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is 4-chlorophenylalanine
<220> FEATURE:
<221> NAME/KEY: MISC_FEATURE
<222> LOCATION: (2)..(2)
<223> OTHER INFORMATION: is any amino acid

<400> SEQUENCE: 137

Phe Xaa Glu Pro Ala Tyr Gln Arg Phe Leu
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid
```

```
<400> SEQUENCE: 138

Trp Xaa Glu Pro Ala Tyr Gln Arg Glu Leu
 1               5                  10

<210> SEQ ID NO 139
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 139

Trp Xaa Glu Pro Ala Tyr Gln Arg Leu Leu
 1               5                  10

<210> SEQ ID NO 140
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 140

Trp Xaa Glu Pro Ala Tyr Gln Arg Lys Leu
 1               5                  10

<210> SEQ ID NO 141
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 141

Trp Xaa Glu Pro Ala Tyr Gln Arg Gln
 1               5

<210> SEQ ID NO 142
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 142

Trp Xaa Glu Pro Ala Tyr Gln Arg Tyr Leu
 1               5                  10

<210> SEQ ID NO 143
<211> LENGTH: 10
<212> TYPE: PRT
<213> ORGANISM: Artificial Sequence
<220> FEATURE:
```

```
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid
<220> FEATURE:
<221> NAME/KEY: MISC_FEATURE
<222> LOCATION: (9)..(9)
<223> OTHER INFORMATION: is 4-chlorophenylalanine

<400> SEQUENCE: 143

Trp Xaa Glu Pro Ala Tyr Gln Arg Phe Leu
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 144

Trp Xaa Glu Pro Ala Tyr Gln Arg Phe Leu
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 145

Trp Xaa Glu Pro Ala Tyr Gln Arg Arg Glu
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 146

Trp Xaa Glu Pro Ala Tyr Gln Arg Phe Lys
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 147
```

Trp Xaa Glu Pro Ala Tyr Gln Arg Phe Gln
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 148

Trp Xaa Glu Pro Ala Tyr Gln Arg Phe Thr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 149

Trp Xaa Glu Pro Ala Tyr Gln Arg Phe Phe
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 150

Xaa Glu Pro Ala Tyr Gln Arg Phe Leu
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 151

Xaa Glu Pro Ala Tyr Gln Arg Glu Leu
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Sequence

```
<220> FEATURE:
<221> NAME/KEY: MISC_FEATURE
<222> LOCATION: (1)..(1)
<223> OTHER INFORMATION: is any amino acid

<400> SEQUENCE: 152

Xaa Glu Pro Ala Tyr Gln Arg Leu Leu
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 153

Xaa Glu Pro Ala Tyr Gln Arg Lys Leu
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 154

Xaa Glu Pro Ala Tyr Gln Arg Gln Leu
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 155

Xaa Glu Pro Ala Tyr Gln Arg Tyr Leu
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid
<220> FEATURE:
<221> NAME/KEY: MISC_FEATURE
<222> LOCATION: (8)..(8)
<223> OTHER INFORMATION: is 4-chlorophenylalanine

<400> SEQUENCE: 156
```

```
Xaa Glu Pro Ala Tyr Gln Arg Phe Leu
1               5
```

<210> SEQ ID NO 157
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 157

```
Xaa Glu Pro Ala Tyr Gln Arg Phe Leu
1               5
```

<210> SEQ ID NO 158
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 158

```
Xaa Glu Pro Ala Tyr Gln Arg Phe Glu
1               5
```

<210> SEQ ID NO 159
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 159

```
Xaa Glu Pro Ala Tyr Gln Arg Phe Lys
1               5
```

<210> SEQ ID NO 160
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 160

```
Xaa Glu Pro Ala Tyr Gln Arg Phe Gln
1               5
```

<210> SEQ ID NO 161
<211> LENGTH: 9
<212> TYPE: PRT
<213> ORGANISM: Artificial Sequence
<220> FEATURE:
<223> OTHER INFORMATION: Synthetic Sequence
<220> FEATURE:

```
<221> NAME/KEY: MISC_FEATURE
<222> LOCATION: (1)..(1)
<223> OTHER INFORMATION: is any amino acid

<400> SEQUENCE: 161

Xaa Glu Pro Ala Tyr Gln Arg Phe Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: is any amino acid

<400> SEQUENCE: 162

Xaa Glu Pro Ala Tyr Gln Arg Phe Phe
1               5

<210> SEQ ID NO 163
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 163

Lys Ser Leu Ser Arg His Asp His Ile His His His
1               5                   10

<210> SEQ ID NO 164
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 164

Gly Gly Cys Leu Gln Ile Leu Pro Thr Leu Ser Glu Cys Phe Gly Arg
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 165

Gly Leu Lys Val Cys Gly Arg Tyr Pro Gly Ile Cys Asp Gly Ile Arg
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 166

Gly Lys Tyr Thr Trp Tyr Gly Tyr Ser Leu Arg Ala Asn Trp Met Arg
1               5                   10                  15
```

```
<210> SEQ ID NO 167
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 167

Val Pro Cys Gln Lys Arg Pro Gly Trp Val Cys Leu Trp
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 168

Lys Trp Cys Val Ile Trp Ser Lys Glu Gly Cys Leu Phe
1               5                   10

<210> SEQ ID NO 169
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 169

Ser Ser Trp Cys Met Arg Gly Gln Tyr Asn Lys Ile Cys Met Trp
1               5                   10                  15

<210> SEQ ID NO 170
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 170

Val Glu Cys Tyr Leu Ile Arg Asp Asn Leu Cys Ile Tyr
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 171

Trp Trp Cys Leu Gly Glu Arg Val Val Arg Cys Ala His
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 172

Phe Tyr Cys Val Ile Glu Arg Leu Gly Val Cys Leu Tyr
1               5                   10

<210> SEQ ID NO 173
```

```
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 173

Arg Val Cys Phe Leu Trp Gln Asp Gly Arg Cys Val Phe
1               5                   10

<210> SEQ ID NO 174
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 174

Asn Arg Leu Lys Cys Arg Ala Gln Ala Thr His Ser Ala Ala Pro Cys
1               5                   10                  15

Ile Arg Gly Tyr
            20

<210> SEQ ID NO 175
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 175

Arg Gln Asn Ser Cys Thr Tyr Ser Asp Ala Arg Arg Trp Ala Leu Cys
1               5                   10                  15

Trp Ser Gly Glu
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 176

Gln Leu Asn Ser Cys Ile His Ser Gly Asp Arg Ala Ile Arg Gly Cys
1               5                   10                  15

Met Asp Trp Val
            20

<210> SEQ ID NO 177
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 177

Lys Tyr Gly Leu Cys Arg Asp Glu Thr Val Phe Pro Ser His Ser Cys
1               5                   10                  15

Thr Phe Thr Gly
            20

<210> SEQ ID NO 178
<211> LENGTH: 20
<212> TYPE: PRT
```

```
<213> ORGANISM: Artificial Sequence
<220> FEATURE:
<223> OTHER INFORMATION: Synthetic Sequence

<400> SEQUENCE: 178

Gly Ser Pro Gln Cys Pro Gly Gly Phe Asn Cys Pro Arg Cys Asp Cys
1               5                   10                  15

Gly Ala Gly Tyr
            20

<210> SEQ ID NO 179
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 179

Gly Thr Gly Ser Cys Gly Tyr Gly Lys Leu His Thr Gly Tyr Trp Cys
1               5                   10                  15

Ser Tyr Phe Pro
            20

<210> SEQ ID NO 180
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 180

Asn Ser Ser Ser Cys Asp Thr Ser Val Val Arg Ser Thr Trp Ala Cys
1               5                   10                  15

Ile Leu Gln Pro
            20

<210> SEQ ID NO 181
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 181

Val Arg Ala Val Cys Thr Thr Leu Lys Ser Arg Gly His Glu Glu Cys
1               5                   10                  15

Trp Ser Leu Gln
            20

<210> SEQ ID NO 182
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 182

Val Tyr Ala Gln Cys Gly Val Asn Val Arg Thr Gly Arg Gly Gly Cys
1               5                   10                  15

Ser Arg Leu Met
            20

<210> SEQ ID NO 183
<211> LENGTH: 20
```

```
<212> TYPE: PRT
<213> ORGANISM: Artificial Sequence
<220> FEATURE:
<223> OTHER INFORMATION: Synthetic Sequence

<400> SEQUENCE: 183

Val His Met Asn Cys Ser Trp Met Arg Val Ser Glu Gly His Pro Cys
1               5                   10                  15

Glu Ser Ala Asp
            20

<210> SEQ ID NO 184
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 184

Gly Arg Gln Gly Cys Tyr Glu His Leu Trp Arg Leu Ile Ala Trp Cys
1               5                   10                  15

Ala Ile Phe Leu
            20

<210> SEQ ID NO 185
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 185

Leu Arg Met Thr Cys Ala Phe Gly Val Ala Gln Arg Ser Ala Asp Cys
1               5                   10                  15

Ala Leu Ser Ser
            20

<210> SEQ ID NO 186
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 186

Ser Ile Val Asn Cys Ser Ala Ala Leu Thr Asp Leu Pro Thr Arg Cys
1               5                   10                  15

Gly Gly Asn Ile
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 187

Cys Gly Thr Arg Cys Val Arg Cys Gln Asn Gly Pro Glu Ala Ser Cys
1               5                   10                  15

Glu Gln Pro Leu
            20

<210> SEQ ID NO 188
```

```
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 188

Thr Pro Leu Phe Cys Gly Asn His Gly Arg Gln Pro Ser Pro Leu Cys
1               5                   10                  15

Met Lys Trp Asp
            20

<210> SEQ ID NO 189
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 189

Phe Thr Thr Val Cys Arg Gln Pro Arg Gly His Glu Ala Ile Val Cys
1               5                   10                  15

Gly Ser Gly Lys
            20

<210> SEQ ID NO 190
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 190

Ala Pro Ser Phe Cys Gly Thr Ala Met Leu Gly Ala Ser Arg Tyr Cys
1               5                   10                  15

Tyr Ser Gly Pro
            20

<210> SEQ ID NO 191
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 191

Gly Ala Arg Glu Cys Glu Ser Gly Gly Pro Gly Met Arg Lys Leu Cys
1               5                   10                  15

Thr Gln Ile Asn
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 192

Asn Asn Arg Ala Cys Phe Arg Thr Ser Lys Gly Asn Pro Ala Glu Cys
1               5                   10                  15

Pro Tyr Leu Gly
            20
```

```
<210> SEQ ID NO 193
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 193

Gly Ser Leu Ala Cys Gln Asn Ile Val Val Cys Val Lys Lys Gln Cys
1               5                   10                  15

Asn Ala Leu Cys
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 194

Lys Arg Ala Ser Cys Gln Asn Pro Leu Phe Ser Asn Phe Phe Val Cys
1               5                   10                  15

Gly Leu Ser Glu
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 195

Leu Pro Asn Phe Cys Met Asp Thr Ser Gly Arg Ala Gly Pro Leu Cys
1               5                   10                  15

Met Gly Ser Glu
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 196

Arg His Thr Val Cys Arg Val Ser Leu Ser Ser Val Gln Gly Ser Cys
1               5                   10                  15

Ser His Glu Tyr
            20

<210> SEQ ID NO 197
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 197

Cys Gly Leu Ile Ile Gln Lys Asn Glu Cys
1               5                   10

<210> SEQ ID NO 198
<211> LENGTH: 10
```

```
<212> TYPE: PRT
<213> ORGANISM: Artificial Sequence
<220> FEATURE:
<223> OTHER INFORMATION: Synthetic Sequence

<400> SEQUENCE: 198

Cys Asn Ala Gly Glu Ser Ser Lys Asn Cys
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 199

Gly Arg Arg Thr Arg Ser Arg Arg Leu Arg Arg Ser
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 200

Ser Met Ser Ile Ala Ser Pro Gln Ile Pro Trp Ser
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 201

Thr Pro Arg Asn Leu Arg Thr Ser Asn Thr His Arg
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 202

Gly Arg Arg Ile Ala Gly Pro Tyr Ile Ala Leu Glu
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 203

Ser Met Pro Ile Asn Ser Pro Tyr Ile Pro Trp Ser
1               5                   10

<210> SEQ ID NO 204
<211> LENGTH: 11
<212> TYPE: PRT
```

<213> ORGANISM: Artificial Sequence
<220> FEATURE:
<223> OTHER INFORMATION: Synthetic Sequence

<400> SEQUENCE: 204

Gly Arg Arg Pro Met Lys Leu Asn Lys Thr Pro
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 205

Gly Arg Arg Ile Asn Arg Leu Ile Leu Pro Arg Asn
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 206

Gly Arg Arg Thr Arg Ser Ser Arg Leu Arg Asn Ser
1               5                   10

<210> SEQ ID NO 207
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 207

Cys Leu Ser Asp Gly Lys Arg Lys Cys
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 208

Cys Leu Asp Gly Gly Arg Pro Lys Cys
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 209

Cys Arg Glu Ala Gly Arg Lys Ala Cys
1               5

<210> SEQ ID NO 210
<211> LENGTH: 9
<212> TYPE: PRT
<213> ORGANISM: Artificial Sequence

```
<220> FEATURE:
<223> OTHER INFORMATION: Synthetic Sequence

<400> SEQUENCE: 210

Cys Ala Gly Arg Arg Ser Ala Tyr Cys
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 211

Cys Asn Arg Arg Thr Lys Ala Gly Cys
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 212

Cys Pro Ile Glu Asp Arg Pro Met Cys
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 213

Cys Gly Arg Arg Ala Gly Gly Ser Cys
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 214

Cys Gly Asn Ser Asn Pro Lys Ser Cys
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 215

Cys Pro His Asn Leu Thr Lys Leu Cys
1               5

<210> SEQ ID NO 216
<211> LENGTH: 6
<212> TYPE: PRT
<213> ORGANISM: Artificial Sequence
<220> FEATURE:
```

<223> OTHER INFORMATION: Synthetic Sequence

<400> SEQUENCE: 216

Gly Pro Leu Pro Leu Arg
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 217

Cys Asp Cys Arg Gly Asp Cys Phe Cys
1               5

<210> SEQ ID NO 218
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 218

Gly His Gly Lys His Lys Asn Lys
1               5

<210> SEQ ID NO 219
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 219

His Lys His Gly His Gly His Gly Lys His Lys Asn Lys Gly Lys
1               5                   10                  15

<210> SEQ ID NO 220
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 220

Lys His Gly His Gly His Gly Lys
1               5

<210> SEQ ID NO 221
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 221

Lys Gly His His Gly Lys His Gly
1               5

<210> SEQ ID NO 222
<211> LENGTH: 8
<212> TYPE: PRT
<213> ORGANISM: Artificial Sequence
<220> FEATURE:
<223> OTHER INFORMATION: Synthetic Sequence

```
<400> SEQUENCE: 222

His Lys Asn Lys Gly Lys Lys Asn
1               5

<210> SEQ ID NO 223
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 223

Cys Arg Gly Arg Arg Ser Thr
1               5

<210> SEQ ID NO 224
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 224

Cys Arg Ser Arg Lys Gly
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 225

Cys Lys Ala Ala Lys Asn Lys
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 226

Cys Lys Gly Ala Lys Ala Arg
1               5

<210> SEQ ID NO 227
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 227

Phe Arg Val Gly Val Ala Asp Val
1               5

<210> SEQ ID NO 228
<211> LENGTH: 8
<212> TYPE: PRT
<213> ORGANISM: Artificial Sequence
<220> FEATURE:
<223> OTHER INFORMATION: Synthetic Sequence
```

```
<400> SEQUENCE: 228

Cys Glu Tyr Gln Leu Asp Val Glu
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 229

Cys Ser Arg Pro Arg Ser Glu Cys
1               5

<210> SEQ ID NO 230
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 230

Cys Gly Lys Arg Lys
1               5

<210> SEQ ID NO 231
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 231

Cys Asp Thr Arg Leu
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 232

Cys Gly Thr Lys Arg Lys Cys
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 233

Cys Asp Thr Ala Val Val Glu Gly Leu
1               5

<210> SEQ ID NO 234
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 234
```

Cys Arg Ser Arg Lys Gly
1               5

<210> SEQ ID NO 235
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 235

Cys Glu Tyr Gln Leu Asp Val Glu
1               5

<210> SEQ ID NO 236
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 236

Cys Pro Ile Glu Asp Arg Pro Met Cys
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 237

Pro Ile Glu Asp Arg Pro Met
1               5

<210> SEQ ID NO 238
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 238

Pro Ile Asp Glu Arg Pro Met
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 239

Ala Leu Arg Asp Arg Pro Met
1               5

<210> SEQ ID NO 240
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 240

```
Pro Met Met Arg Gln Arg Pro Met
1               5
```

<210> SEQ ID NO 241
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 241

```
Pro Leu Ala Ser Arg Pro Met
1               5
```

<210> SEQ ID NO 242
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 242

```
Pro Glu Lys Phe Arg Pro Met
1               5
```

<210> SEQ ID NO 243
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 243

```
Val Pro Glu Gln Arg Pro Met
1               5
```

<210> SEQ ID NO 244
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 244

```
Asp Leu Pro Met His Pro Met
1               5
```

<210> SEQ ID NO 245
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 245

```
Gln Phe Gln Ser Gln Pro Met
1               5
```

<210> SEQ ID NO 246
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 246

```
Gln Pro Pro Met Glu Tyr Ser
```

```
1               5

<210> SEQ ID NO 247
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 247

Asn Gly Arg Ser Leu
1               5

<210> SEQ ID NO 248
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 248

Met Thr Gln Met Ile Ser
1               5

<210> SEQ ID NO 249
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 249

Thr Ala Leu Ser Pro Gln
1               5

<210> SEQ ID NO 250
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 250

Trp Asn Leu Pro Trp Tyr Tyr Ser Val Ser Pro Thr
1               5                   10

<210> SEQ ID NO 251
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 251

Leu Thr Val Leu Pro Trp
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 252

Leu Thr Val Glu Pro Trp Leu
1               5
```

<210> SEQ ID NO 253
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 253

Leu Thr Val Ser Pro Leu Trp Asp
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 254

Leu Thr Val Thr Pro Trp Leu
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 255

Leu Thr Val Gln Pro Trp Pro
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 256

Leu Thr Val Ser Pro Trp Thr
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 257

Val Leu Thr Val Gln Pro Trp
1               5

<210> SEQ ID NO 258
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 258

Leu Thr Val Ser Leu Trp Thr
1               5

```
<210> SEQ ID NO 259
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 259

Pro Gly Val Ile Pro Trp Asn
1               5

<210> SEQ ID NO 260
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 260

Leu Thr Tyr Gln Thr Trp Pro
1               5

<210> SEQ ID NO 261
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 261

Glu Leu Tyr Val Ser Arg Leu
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 262

Asn Leu Tyr Tyr Ala Ser Trp
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 263

Thr Leu Thr Val Leu Pro Trp
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 264

Asn Leu Tyr Val Ala Ser Trp
1               5
```

```
<210> SEQ ID NO 265
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 265

Ser Met Ser Ile Ala Arg Leu
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 266

Val Ser Phe Leu Glu Tyr Arg
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 267

Cys Pro Gly Pro Glu Gly Ala Gly Cys
1               5

<210> SEQ ID NO 268
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: is D-phenylalanine

<400> SEQUENCE: 268

Arg Gly Asp Phe Lys
1               5

<210> SEQ ID NO 269
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 269

Pro Arg Pro Gly Ala Pro Leu Ala Gly Ser Trp Pro Gly Thr Ser
1               5                   10                  15

<210> SEQ ID NO 270
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 270

Ala Asp Gly Ala Pro Arg Pro Gly Ala Pro Leu Ala
```

<210> SEQ ID NO 271
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 271

Asp Arg Trp Arg Pro Ala Leu Pro Val Val Leu Phe Pro Leu His
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 272

Ala Ser Ser Ser Tyr Pro Leu Ile His Trp Arg Pro Trp Ala Arg
1               5                   10                  15

<210> SEQ ID NO 273
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 273

Asp Arg Trp Arg Pro Ala Leu Pro
1               5

<210> SEQ ID NO 274
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 274

Ile His Trp Arg Pro Trp Ala Arg
1               5

<210> SEQ ID NO 275
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 275

Ala Ala Glu Trp Leu Asp Ala Phe Phe Val Arg His Val Asp Arg
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 276

Gly Asp Val Trp Leu Phe Leu Thr Ser Thr Ser His Phe Ala Arg
1               5                   10                  15

```
<210> SEQ ID NO 277
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 277

Gly Cys Ser Val Ser Ser Val Gly Ala Leu Cys Thr His Val
1               5                   10

<210> SEQ ID NO 278
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 278

Ala Pro Cys Cys Ser His Leu Asp Ala Ser Pro Phe Gln Arg Pro
1               5                   10                  15

<210> SEQ ID NO 279
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 279

Ala Gln Ser Asn Phe Val Thr Trp Gly Tyr Asn Val Ala Val
1               5                   10

<210> SEQ ID NO 280
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 280

Arg Ala Ser Asp Val Gly Ser Asp Val Val Pro Arg Tyr Pro Phe
1               5                   10                  15

<210> SEQ ID NO 281
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 281

Met Ala Arg Ser Gly Leu
1               5

<210> SEQ ID NO 282
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 282

Met Ala Arg Ala Lys Glu
1               5
```

<210> SEQ ID NO 283
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 283

Met Ser Arg Thr Met Ser
1               5

<210> SEQ ID NO 284
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 284

Met Thr Lys Ser Ala Gly
1               5

<210> SEQ ID NO 285
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 285

Met Thr Lys Cys Arg Gly
1               5

<210> SEQ ID NO 286
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 286

Met Thr Arg Asn Leu Gln
1               5

<210> SEQ ID NO 287
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 287

Met Thr Arg Gln Ile Gly
1               5

<210> SEQ ID NO 288
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 288

Met Ser Arg Pro His Lys
1               5

```
<210> SEQ ID NO 289
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 289

Met Ala Lys His Ala Met
1               5

<210> SEQ ID NO 290
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 290

Cys Trp Trp Arg Leu Glu Gly Cys
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 291

Cys Leu Gln Leu Phe Ser Thr Cys
1               5

<210> SEQ ID NO 292
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 292

Cys Ala Lys Gly Tyr Arg Ser Cys
1               5

<210> SEQ ID NO 293
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 293

Cys Thr Gly Ser Trp Leu Gly Cys
1               5

<210> SEQ ID NO 294
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 294

Ala Glu Gly Glu Phe Met Tyr Trp Gly Asp Ser His Trp Leu Gln Tyr
1               5                   10                  15

Trp Tyr Glu Gly Asp Pro Ala Lys
            20
```

```
<210> SEQ ID NO 295
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 295

Ala Glu Gly Glu Phe Trp Gly Asp Ser His Trp Leu Gln Tyr Trp Tyr
1               5                   10                  15

Glu Gly Asp Pro Ala Lys
            20

<210> SEQ ID NO 296
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 296

Ala Glu Gly Glu Phe Ile His Asn Arg Tyr Asn Arg Phe Phe Tyr Trp
1               5                   10                  15

Tyr Gly Asp Pro Ala Lys
            20

<210> SEQ ID NO 297
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 297

Ala Glu Gly Glu Phe Pro Arg Trp Gly Asp Ser His Trp Leu Gln Tyr
1               5                   10                  15

Trp Tyr Glu Gly Asp Pro Ala Lys
            20

<210> SEQ ID NO 298
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 298

Ala Glu Gly Glu Phe Leu Met Trp Gly Gly Ser His Trp Leu Glu Tyr
1               5                   10                  15

Trp Tyr Glu Gly Asp Pro Ala Lys
            20

<210> SEQ ID NO 299
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 299

Ala Glu Gly Glu Phe Gly His Trp Cys Asp Gln His Trp Leu Gln Tyr
1               5                   10                  15

Trp Tyr Glu Gly Asp Pro Ala Lys
```

20

<210> SEQ ID NO 300
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 300

Ala Glu Gly Glu Phe Gly Trp Trp Gly Asp Ser His Trp Leu Gln Tyr
1               5                   10                  15

Glu Gly Asp Pro Ala Lys
            20

<210> SEQ ID NO 301
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 301

Cys Arg Gly Asp Cys Phe
1               5

<210> SEQ ID NO 302
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 302

Cys Asp Cys Arg Gly Asp Cys Phe Cys
1               5

<210> SEQ ID NO 303
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 303

Cys Asn Gly Arg Cys Val Ser Gly Cys Ala Gly Arg Cys
1               5                   10

<210> SEQ ID NO 304
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 304

Cys Gly Ser Leu Val Arg Cys
1               5

<210> SEQ ID NO 305
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 305

```
Cys Arg Gly Asp Cys Gly Gly Lys Trp Cys Phe Arg Val Cys Tyr Arg
1               5                   10                  15

Gly Ile Cys Tyr Arg Arg Cys Arg
            20
```

<210> SEQ ID NO 306
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 306

```
Met Cys Pro Lys His Pro Leu Gly Cys
1               5
```

<210> SEQ ID NO 307
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 307

```
Leu Cys Pro Lys His Pro Leu Gly Cys
1               5
```

<210> SEQ ID NO 308
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 308

```
His Leu Gln Ile Gln Pro Trp Tyr Pro Gln Ile Ser
1               5                   10
```

<210> SEQ ID NO 309
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 309

```
Val Pro Trp Met Glu Pro Ala Tyr Gln Arg Phe Leu
1               5                   10
```

<210> SEQ ID NO 310
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 310

```
Leu Ser Ser Val Asn Ser Phe Pro Val Val Thr Pro
1               5                   10
```

<210> SEQ ID NO 311
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 311

Gln Pro Trp Leu Glu Gln Ala Tyr Tyr Ser Thr Phe
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 312

Ser Ala Leu Leu Pro Trp Pro Val Leu Val Asn Tyr
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 313

Ile Thr Thr Pro Trp Asp Glu Met Arg Ser Phe Leu
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 314

His Ser Phe Leu His Pro Trp Asp Leu Phe Asp Tyr
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 315

Val Pro Trp Met Glu Pro Ala Tyr Gln Arg Phe Leu
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 316

Met Leu Pro Lys Pro Ser Ser Phe Pro Val Pro Gly
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 317

His Ser Phe Leu His Pro Trp Asp Leu Phe Asp Tyr
1               5                   10

<210> SEQ ID NO 318
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 318

Cys Asn Gly Arg Cys Val Ser Gly Cys Ala Gly Arg Cys
1               5                   10

<210> SEQ ID NO 319
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 319

Cys Val Leu Asn Gly Arg Met Glu Cys
1               5

<210> SEQ ID NO 320
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 320

Phe Asp Asp Ala Arg Leu
1               5

<210> SEQ ID NO 321
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 321

Phe Ser Asp Ala Arg Leu
1               5

<210> SEQ ID NO 322
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 322

Phe Ser Asp Met Arg Leu
1               5

<210> SEQ ID NO 323
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 323

Phe Val Asp Val Arg Leu
1               5

<210> SEQ ID NO 324
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 324

Phe Thr Asp Ile Arg Leu
1               5

<210> SEQ ID NO 325
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 325

Phe Asn Asp Tyr Arg Leu
1               5

<210> SEQ ID NO 326
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 326

Phe Ser Asp Thr Arg Leu
1               5

<210> SEQ ID NO 327
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 327

Asp Pro Ala Phe Ile Phe Tyr His Ser Thr Leu Phe Phe Asn Ser
1               5                   10                  15

<210> SEQ ID NO 328
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 328

Gly Gly His Asp Gly Asp Pro Val Leu Thr Gly Thr Leu Phe Tyr
1               5                   10                  15

<210> SEQ ID NO 329
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 329

```
Ala Val Asp Pro Arg Met Phe Tyr Leu Leu Arg Gly Gly Ala
1               5                   10                  15

<210> SEQ ID NO 330
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 330

Pro Ile His Tyr Ile Phe
1               5

<210> SEQ ID NO 331
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 331

Tyr Ile His Tyr Ile Phe
1               5

<210> SEQ ID NO 332
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 332

Arg Ile His Tyr Ile Phe
1               5

<210> SEQ ID NO 333
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 333

Trp Arg Glu Trp Phe Leu
1               5

<210> SEQ ID NO 334
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 334

Trp Trp Ala Met Lys Pro
1               5

<210> SEQ ID NO 335
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 335

Leu Ile Leu Ser Ser Gly Glu Leu Leu Arg His Pro Arg Gly
```

```
1               5                   10
```

<210> SEQ ID NO 336
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 336

```
Thr Ala Ala Ser Gly Val Arg Ser Met His
1               5                   10
```

<210> SEQ ID NO 337
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 337

```
Leu Thr Leu Arg Trp Val Gly Leu Met Ser
1               5                   10
```

<210> SEQ ID NO 338
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 338

```
Gly Gly Gly Thr Arg Ala Gly Met Lys Tyr
1               5                   10
```

<210> SEQ ID NO 339
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 339

```
Trp Gly Lys Ile Glu Asp Pro Leu Arg Ala
1               5                   10
```

<210> SEQ ID NO 340
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 340

```
Ala Gly Gln Thr Leu Thr Ala Ser Gly Asp
1               5                   10
```

<210> SEQ ID NO 341
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 341

```
Asp Leu Leu Ala Val Ser Trp Leu Arg Ala
1               5                   10
```

<210> SEQ ID NO 342
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 342

Ser Ala Glu Arg Gly Val Val Ala Met Ser
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 343

Ala Ile His Ser Glu Leu Met Trp Val Ser
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 344

Phe Trp Thr Glu Arg Ala Gly Trp Ala Tyr
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 345

Met Val Trp Ser Lys Gly Pro Leu Phe Leu
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 346

Ala Gly Thr Arg Met Ser Trp Glu Val Leu
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 347

Val Ser Arg Ser Ser Arg Trp Gly Ser Ile
1               5                   10

<210> SEQ ID NO 348
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 348

Asp Ala His Val Leu Val Pro Arg Thr Pro
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 349

Ala Gln Gly Ile Val Leu Gln Leu Ala Leu
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 350

Leu Ser Pro Leu Leu Ser Pro Ala Thr Ala
1               5                   10

<210> SEQ ID NO 351
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 351

Cys Asp Cys Arg Gly Asp Cys Phe Cys
1               5

<210> SEQ ID NO 352
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 352

Cys Asn Gly Arg Cys Val Ser Gly Cys Ala Gly Arg Cys
1               5                   10

<210> SEQ ID NO 353
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 353

Asn Gly Arg Ala His Ala
1               5

```
<210> SEQ ID NO 354
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 354

Cys Val Leu Asn Gly Arg Met Glu Cys
1               5

<210> SEQ ID NO 355
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 355

His Gly Arg Phe Ile Leu Pro Trp Trp Tyr Ala Phe Ser Pro Ser
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 356

Arg Phe Arg Gly Leu Ile Ser Leu Ser Gln Val Tyr Leu Ser Pro
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 357

Ala Arg Val Ser Phe Trp Arg Tyr Ser Ser Phe Ala Pro Thr Tyr
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 358

Gly Ser Trp Tyr Ala Trp Ser Pro Leu Val Pro Ser Ala Gln Ile
1               5                   10                  15

<210> SEQ ID NO 359
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 359

Lys Lys Glu Lys Asp Ile Met Lys Lys Thr Ile
1               5                   10

<210> SEQ ID NO 360
```

```
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 360

Gly Arg Gly Asp Ser Pro Lys
1               5

<210> SEQ ID NO 361
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 361

Ser Asn Pro Phe Ser Lys Pro Tyr Gly Leu Thr Val
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 362

Tyr Pro His Tyr Ser Leu Pro Gly Ser Ser Thr Leu
1               5                   10

<210> SEQ ID NO 363
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 363

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 364
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 364

Thr Leu Thr Tyr Thr Trp Ser
1               5

<210> SEQ ID NO 365
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 365

Cys Arg Glu Lys Ala
1               5
```

<210> SEQ ID NO 366
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 366

Cys Gly Gln Lys Arg Thr Arg Gly Cys
1               5

<210> SEQ ID NO 367
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 367

Arg Pro Ala Arg Pro Ala Arg
1               5

<210> SEQ ID NO 368
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 368

Cys Arg Gly Asp Gly Trp Cys
1               5

<210> SEQ ID NO 369
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 369

Arg Gly Asp Gly Trp Lys
1               5

<210> SEQ ID NO 370
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 370

Thr Ser Pro Leu Asn Ile His Asn Gly Gln Lys Leu
1               5                   10

<210> SEQ ID NO 371
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 371

Cys Arg Gly Asp Lys Gly Pro Asp Cys
1               5

```
<210> SEQ ID NO 372
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 372

Cys Arg Gly Asp Arg Gly Pro Asp Cys
1               5

<210> SEQ ID NO 373
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 373

Cys Arg Gly Asp Lys Thr Thr Asn Cys
1               5

<210> SEQ ID NO 374
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 374

Cys Arg Gly Asp His Ala Gly Asp Cys
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 375

Cys Arg Gly Asp His Gly Val Glu Cys
1               5

<210> SEQ ID NO 376
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 376

Cys Gly Arg Gly Asp Asn Leu Pro Cys
1               5

<210> SEQ ID NO 377
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 377

Cys Gly Arg Gly Asp Asn Leu Ala Cys
1               5

<210> SEQ ID NO 378
```

```
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 378

Cys Glu Lys Arg Gly Asp Asn Leu Cys
1               5

<210> SEQ ID NO 379
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 379

Cys Glu Lys Arg Gly Asp Ser Val Cys
1               5

<210> SEQ ID NO 380
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 380

Cys Ser Gly Arg Gly Asp Ser Leu Cys
1               5

<210> SEQ ID NO 381
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 381

Cys Gly Lys Arg Gly Asp Ser Ile Cys
1               5

<210> SEQ ID NO 382
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 382

Cys Thr Gly Arg Gly Asp Ala Leu Cys
1               5

<210> SEQ ID NO 383
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 383

Cys Arg Gly Asp Ser Ala Cys
1               5

<210> SEQ ID NO 384
<211> LENGTH: 9
```

-continued

```
<212> TYPE: PRT
<213> ORGANISM: Artificial Sequence
<220> FEATURE:
<223> OTHER INFORMATION: Synthetic Sequence

<400> SEQUENCE: 384

Cys Arg Gly Asp Lys Gly Glu Asn Cys
1               5

<210> SEQ ID NO 385
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 385

Cys Gly Arg Gly Asp Ser Pro Asp Cys
1               5

<210> SEQ ID NO 386
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 386

Cys Arg Gly Asp Lys Gly Pro Glu Cys
1               5

<210> SEQ ID NO 387
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 387

Cys Arg Gly Asp Lys His Ala Asp Cys
1               5

<210> SEQ ID NO 388
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 388

Cys Arg Gly Asp His Ala Ala Asn Cys
1               5

<210> SEQ ID NO 389
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 389

Cys Arg Gly Asp Ala Gly Ile Asn Cys
1               5

<210> SEQ ID NO 390
<211> LENGTH: 9
<212> TYPE: PRT
```

```
<213> ORGANISM: Artificial Sequence
<220> FEATURE:
<223> OTHER INFORMATION: Synthetic Sequence

<400> SEQUENCE: 390

Cys Gly Arg Gly Asp Met Pro Ser Cys
1               5

<210> SEQ ID NO 391
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 391

Cys Glu Lys Arg Gly Asp Ser Leu Cys
1               5

<210> SEQ ID NO 392
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 392

Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Ala Lys Lys
            20                  25                  30

<210> SEQ ID NO 393
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 393

Cys Arg Glu Lys Ala
1               5

<210> SEQ ID NO 394
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 394

Thr Asp Ser Ile Leu Arg Ser Tyr Asp Trp Thr Tyr
1               5                   10

<210> SEQ ID NO 395
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 395

Asp Met Pro Lys Gln Leu Leu Ala Pro Trp Tyr Tyr
1               5                   10

<210> SEQ ID NO 396
```

```
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 396

Asp Met Pro Lys Gln Leu Leu Ala Pro Trp Tyr Tyr
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 397

Ser Tyr Pro Leu Ser Phe Leu Gly Pro Leu Ile Ser
1               5                   10

<210> SEQ ID NO 398
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 398

Thr Gln Gln Pro Leu Glu Gly His Gln Leu Pro Tyr
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 399

Thr Gly Val Ser Trp Ser Val Ala Gln Pro Ser Phe
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 400

Ser Val Ser Val Gly Met Lys Pro Ser Pro Arg Pro
1               5                   10

<210> SEQ ID NO 401
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 401

Ser Gln Trp Asn Ser Pro Pro Ser Ser Ala Ala Phe
1               5                   10

<210> SEQ ID NO 402
<211> LENGTH: 9
```

<212> TYPE: PRT
<213> ORGANISM: Artificial Sequence
<220> FEATURE:
<223> OTHER INFORMATION: Synthetic Sequence

<400> SEQUENCE: 402

Cys Gly Asn Ser Asn Pro Lys Ser Cys
1               5

<210> SEQ ID NO 403
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 403

Ser Phe Ser Ile Ile His Thr Pro Ile Leu Pro Leu
1               5                   10

<210> SEQ ID NO 404
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 404

Gly Asn Gly Arg Ala His Ala
1               5

<210> SEQ ID NO 405
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 405

Ala His Leu Pro Ile Val Arg Ala Ser Leu Pro Ser
1               5                   10

<210> SEQ ID NO 406
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 406

Thr Pro Met Asn His His Ser Gln His Ala Glu Arg
1               5                   10

<210> SEQ ID NO 407
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 407

Gly Asn Ile Ile Pro Asp Arg Pro Met His Pro Thr
1               5                   10

<210> SEQ ID NO 408
<211> LENGTH: 12
<212> TYPE: PRT

<213> ORGANISM: Artificial Sequence
<220> FEATURE:
<223> OTHER INFORMATION: Synthetic Sequence

<400> SEQUENCE: 408

Phe Pro Ser Ser Leu Ile Ile Pro Pro Leu Pro Asn
1               5                   10

<210> SEQ ID NO 409
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 409

Glu Asp Ile Lys Pro Lys Thr Ser Leu Ala Phe Arg
1               5                   10

<210> SEQ ID NO 410
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 410

Tyr Glu Asp Ile Lys Pro Lys Thr Ser Leu Ala Phe Arg
1               5                   10

<210> SEQ ID NO 411
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 411

Thr Gln Pro Ala Asp Leu Gln Thr His Asn His Asn
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 412

Phe Asp His Ser Ser Lys Trp Thr Arg Thr Ser Pro
1               5                   10

<210> SEQ ID NO 413
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 413

Tyr Ser His Asn Thr Ile Thr Asn Leu Tyr Phe Ser
1               5                   10

<210> SEQ ID NO 414
<211> LENGTH: 12
<212> TYPE: PRT
<213> ORGANISM: Artificial Sequence

```
<220> FEATURE:
<223> OTHER INFORMATION: Synthetic Sequence

<400> SEQUENCE: 414

Trp Pro Arg Tyr Ala Glu Ser Thr Leu Gln Leu Arg
1               5                   10

<210> SEQ ID NO 415
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 415

Lys Gly Val Ser Leu Ser Tyr Arg Lys Lys Gly Val Ser Leu Ser Tyr
1               5                   10                  15

Arg

<210> SEQ ID NO 416
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 416

Ser Val Ser Val Gly Met Lys Pro Ser Pro Arg Pro
1               5                   10

<210> SEQ ID NO 417
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 417

Trp Pro Leu His Thr Ser Val Tyr Pro Pro Ser Pro
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 418

Asn Thr Leu Pro Pro Phe Ser Pro Ser Pro Pro
1               5                   10

<210> SEQ ID NO 419
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 419

Ser Phe Pro Asp Ser Asn Ile Ala Pro Ser Ser Pro
1               5                   10

<210> SEQ ID NO 420
<211> LENGTH: 12
<212> TYPE: PRT
```

<213> ORGANISM: Artificial Sequence
<220> FEATURE:
<223> OTHER INFORMATION: Synthetic Sequence

<400> SEQUENCE: 420

Gln His Ala Pro Ser Asn Ser Lys Ser Val Leu Thr
1               5                   10

<210> SEQ ID NO 421
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 421

Trp Pro Thr Tyr Leu Asn Pro Ser Ser Leu Lys Ala
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 422

Gly Pro Ser Gly Asn Leu His Ile Arg Pro Ala Ser
1               5                   10

<210> SEQ ID NO 423
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 423

Ser Pro Leu Leu Ser Thr Arg Ala Val Gln Leu Ser
1               5                   10

<210> SEQ ID NO 424
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 424

Ser Pro Met Phe Thr Met Ile Gln Gly Asp Ala Gln
1               5                   10

<210> SEQ ID NO 425
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 425

Val Asn Ser His Gln Ala Leu Trp Ser Pro Ala Gln
1               5                   10

<210> SEQ ID NO 426
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 426

Ser Thr Leu Pro Pro Pro Leu Arg Phe Ala Asn Val
1               5                   10

<210> SEQ ID NO 427
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 427

Ser Phe Asn Gln Pro Tyr Leu Tyr Lys Thr Ala Phe
1               5                   10

<210> SEQ ID NO 428
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 428

Tyr His Thr Arg Ile Ala Leu Pro Asp Asn Leu Pro
1               5                   10

<210> SEQ ID NO 429
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 429

Ala Gln Ser Thr Ala Phe Gln Lys Pro Leu Leu Met
1               5                   10

<210> SEQ ID NO 430
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 430

Lys Cys Cys Tyr Ser Leu
1               5

<210> SEQ ID NO 431
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 431

Arg Leu Leu Asp Thr Asn Arg Pro Leu Leu Pro Tyr
1               5                   10

<210> SEQ ID NO 432
<211> LENGTH: 9
<212> TYPE: PRT
<213> ORGANISM: Artificial Sequence
<220> FEATURE:

```
<223> OTHER INFORMATION: Synthetic Sequence

<400> SEQUENCE: 432

Cys Ser Asp Ser Trp His Tyr Trp Cys
1               5

<210> SEQ ID NO 433
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 433

Phe Gln His Pro Ser Phe Ile
1               5

<210> SEQ ID NO 434
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 434

Ser Met Ser Ile Ala Ser Pro Tyr Ile Ala Leu Glu
1               5                   10

<210> SEQ ID NO 435
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 435

Ser Met Ser Ile Ala Ser Pro Tyr Ile Pro Trp Ser
1               5                   10

<210> SEQ ID NO 436
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 436

Ser Pro Gly Pro Met Lys Leu Leu Lys Thr Pro Leu
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 437

Thr Leu Asn Ile Asn Arg Leu Ile Leu Pro Arg Thr
1               5                   10

<210> SEQ ID NO 438
<211> LENGTH: 12
<212> TYPE: PRT
<213> ORGANISM: Artificial Sequence
<220> FEATURE:
<223> OTHER INFORMATION: Synthetic Sequence
```

```
<400> SEQUENCE: 438

Ser Met Ser Ile Gly Ser Pro Tyr Ile Thr Phe Gly
1               5                   10

<210> SEQ ID NO 439
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 439

Val Pro Asn Thr Asn Ser Leu Pro Ala Ala Val Asn
1               5                   10

<210> SEQ ID NO 440
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 440

Leu Ile Ala Lys Thr Ala Leu Pro Gln Thr Asn Lys
1               5                   10

<210> SEQ ID NO 441
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 441

Leu Ile Ala Lys Thr Ala Leu Pro Gln Thr Asn
1               5                   10

<210> SEQ ID NO 442
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 442

Cys Pro His Ser Lys Pro Cys Leu Cys
1               5

<210> SEQ ID NO 443
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 443

Gly Gly Cys Arg Gly Asp Met Phe Gly Cys
1               5                   10

<210> SEQ ID NO 444
<211> LENGTH: 12
<212> TYPE: PRT
<213> ORGANISM: Artificial Sequence
<220> FEATURE:
<223> OTHER INFORMATION: Synthetic Sequence
```

```
<400> SEQUENCE: 444

Phe Arg Pro Asn Arg Ala Gln Asp Tyr Asn Thr Asn
1               5                   10

<210> SEQ ID NO 445
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 445

Gln Glu Phe Ser Pro Tyr Met Gly Leu Glu Phe Lys Lys His
1               5                   10

<210> SEQ ID NO 446
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 446

Gln Glu Phe Ser Pro Asn Leu Trp Gly Leu Glu Phe Gln Lys Asn
1               5                   10                  15

<210> SEQ ID NO 447
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 447

Gln Glu Tyr Ser Pro Asn Leu Trp Gly His Glu Phe Arg Ser His
1               5                   10                  15

<210> SEQ ID NO 448
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 448

His Thr Phe Glu Pro Gly Val
1               5

<210> SEQ ID NO 449
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 449

Pro Ser Thr Asn His Ala Leu
1               5

<210> SEQ ID NO 450
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 450
```

Pro Ser Thr Leu Thr Ser Ser
1               5

<210> SEQ ID NO 451
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 451

Ala Pro Ser Gln Thr Tyr His
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 452

Lys Ala Met Ser Trp Tyr Ala
1               5

<210> SEQ ID NO 453
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 453

Ser Arg Glu Ser Pro His Pro
1               5

<210> SEQ ID NO 454
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 454

Gln Ser Arg Leu Ser Leu Gly
1               5

<210> SEQ ID NO 455
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 455

Leu Asp His Phe Ala Pro Met
1               5

<210> SEQ ID NO 456
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 456

Leu Asp Lys Lys Thr Thr Ser
1               5

<210> SEQ ID NO 457
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 457

Asn Met Ser Pro Gln Leu Asp
1               5

<210> SEQ ID NO 458
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 458

Ser Gln Arg Gln Thr Leu Asp
1               5

<210> SEQ ID NO 459
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 459

Ser Thr Lys Leu Leu His Glu
1               5

<210> SEQ ID NO 460
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 460

Thr Ser Pro Thr Asn Arg Ser
1               5

<210> SEQ ID NO 461
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 461

Pro His Ser Pro Thr Ser Leu
1               5

<210> SEQ ID NO 462
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 462

His Gly Lys Tyr Phe Val Ser

```
<210> SEQ ID NO 463
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 463

Pro Gln Arg His Val Asn Tyr
1               5

<210> SEQ ID NO 464
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 464

Met Met Ser Gln Leu Ala His
1               5

<210> SEQ ID NO 465
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 465

Pro Met Ala His Leu Glu Phe
1               5

<210> SEQ ID NO 466
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 466

Glu Leu Ile Lys Glu Ser Arg
1               5

<210> SEQ ID NO 467
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 467

Gln Pro Glu Asn Leu Pro Thr
1               5

<210> SEQ ID NO 468
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 468

Asn Thr His Met Thr Ala Phe
1               5
```

<210> SEQ ID NO 469
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 469

Pro Phe Lys Leu Ser Lys His
1               5

<210> SEQ ID NO 470
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 470

Ala Ser Ser Leu His Thr Ile
1               5

<210> SEQ ID NO 471
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 471

His Pro Leu Arg Leu Pro Ala
1               5

<210> SEQ ID NO 472
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 472

His Gln Ser Val Asn Lys Glu
1               5

<210> SEQ ID NO 473
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 473

Leu Gln Asn Pro Thr Pro Glu
1               5

<210> SEQ ID NO 474
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 474

Pro Thr Glu Ala Gln Leu Gln
1               5

```
<210> SEQ ID NO 475
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 475

Leu Phe Ala Gln Leu Gly Pro
1               5

<210> SEQ ID NO 476
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 476

Asn Gln Pro Thr Arg Ala Leu
1               5

<210> SEQ ID NO 477
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 477

Thr Pro Arg Thr Gln Lys Ala
1               5

<210> SEQ ID NO 478
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 478

Ile His Phe Pro Ser Ala Ser
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 479

Pro Leu Arg Ile Ala Gln His
1               5

<210> SEQ ID NO 480
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 480

Cys Arg Leu Thr Gly Gly Lys Gly Val Gly Cys
1               5                   10
```

```
<210> SEQ ID NO 481
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 481

Cys Arg Arg Thr Asn Trp Gln Gly Ala Gly Cys
1               5                   10

<210> SEQ ID NO 482
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 482

Cys Gln Leu Thr Gly Thr His Gly Ala Gly Cys
1               5                   10

<210> SEQ ID NO 483
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 483

Cys Ala Asp Pro Asn Ser Val Arg Ala Met Cys
1               5                   10

<210> SEQ ID NO 484
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 484

Cys Ala Asp Pro Asn Ser Val Arg Ala His Cys
1               5                   10

<210> SEQ ID NO 485
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 485

Cys Ala Ala His Tyr Arg Val Gly Pro Trp Cys
1               5                   10

<210> SEQ ID NO 486
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 486

Pro Gln Asn Ser Lys Ile Pro Gly Pro Thr Phe Leu Asp Pro His
1               5                   10                  15

<210> SEQ ID NO 487
```

```
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 487

Ser Met Glu Pro Ala Leu Pro Asp Trp Trp Trp Lys Met Phe Lys
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 488

Asp Lys Pro Thr Ala Phe Val Ser Val Tyr Leu Lys Thr Ala Leu
1               5                   10                  15

<210> SEQ ID NO 489
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 489

Ala Pro Arg Pro Gly Pro Trp Leu Trp Ser Asn Ala Asp Ser Val
1               5                   10                  15

<210> SEQ ID NO 490
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 490

Gly Val Thr Asp Ser Ser Thr Ser Asn Leu Asp Met Pro His Trp
1               5                   10                  15

<210> SEQ ID NO 491
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 491

Pro Lys Met Thr Leu Gln Arg Ser Asn Ile Arg Pro Ser Met Pro
1               5                   10                  15

<210> SEQ ID NO 492
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 492

Leu Tyr Pro Leu His Thr Tyr Thr Pro Leu Ser Leu Pro Leu Phe
1               5                   10                  15

<210> SEQ ID NO 493
<211> LENGTH: 16
```

```
<212> TYPE: PRT
<213> ORGANISM: Artificial Sequence
<220> FEATURE:
<223> OTHER INFORMATION: Synthetic Sequence

<400> SEQUENCE: 493

Leu Thr Gly Thr Cys Leu Gln Tyr Gln Ser Arg Cys Gly Asn Thr Arg
1               5                   10                  15

<210> SEQ ID NO 494
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 494

Ala Tyr Thr Lys Cys Ser Arg Gln Trp Arg Thr Cys Met Thr Thr His
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 495

Ala Asn Thr Pro Cys Gly Pro Tyr Thr His Asp Cys Pro Val Lys Arg
1               5                   10                  15

<210> SEQ ID NO 496
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 496

Asn Ile Ser Arg Cys Thr His Pro Phe Met Ala Cys Gly Lys Gln Ser
1               5                   10                  15

<210> SEQ ID NO 497
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 497

Pro Arg Asn Ile Cys Ser Arg Arg Asp Pro Thr Cys Trp Thr Thr Tyr
1               5                   10                  15

<210> SEQ ID NO 498
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 498

Gly Cys Asn Gly Arg Cys
1               5

<210> SEQ ID NO 499
<211> LENGTH: 10
<212> TYPE: PRT
```

```
<213> ORGANISM: Artificial Sequence
<220> FEATURE:
<223> OTHER INFORMATION: Synthetic Sequence

<400> SEQUENCE: 499

Gln His Trp Ser Tyr Lys Cys Ile Arg Pro
1               5                   10

<210> SEQ ID NO 500
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 500

Cys Val Ser Asn Pro Arg Trp Lys Cys
1               5

<210> SEQ ID NO 501
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 501

Cys His Val Leu Trp Ser Thr Arg Cys
1               5

<210> SEQ ID NO 502
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 502

Ser Trp Leu Ala Tyr Pro Gly Ala Val Ser Tyr Arg
1               5                   10

<210> SEQ ID NO 503
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 503

Tyr Ser Ala Tyr Pro Asp Ser Val Pro Met Met Ser
1               5                   10

<210> SEQ ID NO 504
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 504

Ser Arg Glu Ser Pro His Pro
1               5

<210> SEQ ID NO 505
<211> LENGTH: 12
<212> TYPE: PRT
<213> ORGANISM: Artificial Sequence
```

```
<220> FEATURE:
<223> OTHER INFORMATION: Synthetic Sequence

<400> SEQUENCE: 505

Val Pro Trp Met Glu Pro Ala Tyr Gln Arg Phe Leu
1               5                   10

<210> SEQ ID NO 506
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 506

Cys Asp Ser Asp Ser Asp Ile Thr Trp Asp Gln Leu Trp Asp Leu Met
1               5                   10                  15
Lys

<210> SEQ ID NO 507
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 507

Ala Thr Leu Asp Gly Val Ser
1               5

<210> SEQ ID NO 508
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 508

Arg Arg His Ser Val Ser Gly
1               5

<210> SEQ ID NO 509
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 509

Ser Gly Trp Phe Ala Gly Ser
1               5

<210> SEQ ID NO 510
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 510

Gly Ser Val Ser His Arg Arg
1               5

<210> SEQ ID NO 511
<211> LENGTH: 7
<212> TYPE: PRT
```

```
<213> ORGANISM: Artificial Sequence
<220> FEATURE:
<223> OTHER INFORMATION: Synthetic Sequence

<400> SEQUENCE: 511

Gly Ser Val Leu Pro Val Leu
1               5

<210> SEQ ID NO 512
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 512

Arg Ser Gly Arg Val Ser Asn
1               5

<210> SEQ ID NO 513
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 513

Asn Ser Val Arg Gly Ser Arg
1               5

<210> SEQ ID NO 514
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 514

Asn Val Val Arg Gln
1               5

<210> SEQ ID NO 515
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 515

Cys Asp Cys Arg Gly Asp Cys Phe Cys
1               5

<210> SEQ ID NO 516
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 516

Cys Ser Asp Ser Trp His Tyr Trp Cys
1               5

<210> SEQ ID NO 517
<211> LENGTH: 9
<212> TYPE: PRT
<213> ORGANISM: Artificial Sequence
```

```
<220> FEATURE:
<223> OTHER INFORMATION: Synthetic Sequence

<400> SEQUENCE: 517

Cys Ser Asp Trp Gln His Pro Trp Cys
1               5

<210> SEQ ID NO 518
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 518

Cys Ser Asp Tyr Asn His His Trp Cys
1               5

<210> SEQ ID NO 519
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 519

Cys Ser Asp Gly Gln His Tyr Trp Cys
1               5

<210> SEQ ID NO 520
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 520

Cys Tyr Asp Ser Trp His Tyr Trp Cys
1               5

<210> SEQ ID NO 521
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 521

Cys Phe Asp Gly Asn His Ile Trp Cys
1               5

<210> SEQ ID NO 522
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 522

Cys Thr Asp Phe Pro Arg Ser Phe Cys
1               5

<210> SEQ ID NO 523
<211> LENGTH: 9
<212> TYPE: PRT
<213> ORGANISM: Artificial Sequence
<220> FEATURE:
```

```
<223> OTHER INFORMATION: Synthetic Sequence

<400> SEQUENCE: 523

Cys Thr Gln Asp Arg Gln His Pro Cys
1               5

<210> SEQ ID NO 524
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 524

Cys Leu Ser Arg Tyr Leu Asp Gln Cys
1               5

<210> SEQ ID NO 525
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 525

Cys Pro Arg Glu Cys Glu Ser Ile Cys
1               5

<210> SEQ ID NO 526
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 526

Cys Thr Thr His Trp Gly Phe Thr Leu Cys
1               5                   10

<210> SEQ ID NO 527
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 527

Cys Arg Arg His Trp Gly Phe Glu Phe Cys
1               5                   10

<210> SEQ ID NO 528
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 528

Cys Val Pro Glu Leu Gly His Glu Cys
1               5

<210> SEQ ID NO 529
<211> LENGTH: 12
<212> TYPE: PRT
<213> ORGANISM: Artificial Sequence
<220> FEATURE:
<223> OTHER INFORMATION: Synthetic Sequence
```

```
<400> SEQUENCE: 529

His Thr Met Tyr Tyr His His Tyr Gln His His Leu
1               5                   10

<210> SEQ ID NO 530
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 530

Cys Gly Asn Lys Arg Thr Arg Gly Cys
1               5

<210> SEQ ID NO 531
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 531

Cys Gly Arg Glu Cys Pro Arg Leu Cys Gln Ser Ser Cys
1               5                   10

<210> SEQ ID NO 532
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 532

Cys Gly Glu Ala Cys Gly Gly Gln Cys Ala Leu Pro Cys
1               5                   10

<210> SEQ ID NO 533
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 533

Ile Trp Ser Gly Tyr Gly Val Tyr Trp
1               5

<210> SEQ ID NO 534
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 534

Pro Ser Cys Ala Tyr Met Cys Ile Thr
1               5

<210> SEQ ID NO 535
<211> LENGTH: 9
<212> TYPE: PRT
<213> ORGANISM: Artificial Sequence
<220> FEATURE:
<223> OTHER INFORMATION: Synthetic Sequence
```

```
<400> SEQUENCE: 535

Trp Glu Ser Leu Tyr Phe Pro Arg Glu
1               5

<210> SEQ ID NO 536
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 536

Ser Lys Val Leu Tyr Tyr Asn Trp Glu
1               5

<210> SEQ ID NO 537
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 537

Cys Gly Leu Met Cys Gln Gly Ala Cys Phe Asp Val Cys
1               5                   10

<210> SEQ ID NO 538
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 538

Cys Glu Arg Ala Cys Arg Asn Leu Cys Arg Glu Gly Cys
1               5                   10

<210> SEQ ID NO 539
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 539

Cys Pro Arg Gly Cys Leu Ala Val Cys Val Ser Gln Cys
1               5                   10

<210> SEQ ID NO 540
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 540

Cys Lys Val Cys Asn Gly Arg Cys Cys Gly
1               5                   10

<210> SEQ ID NO 541
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 541
```

```
Cys Glu Met Cys Asn Gly Arg Cys Met Gly
1               5                   10

<210> SEQ ID NO 542
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 542

Cys Pro Leu Cys Asn Gly Arg Cys Ala Leu
1               5                   10

<210> SEQ ID NO 543
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 543

Cys Pro Thr Cys Asn Gly Arg Cys Val Arg
1               5                   10

<210> SEQ ID NO 544
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 544

Cys Gly Val Cys Asn Gly Arg Cys Gly Leu
1               5                   10

<210> SEQ ID NO 545
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 545

Cys Glu Gln Cys Asn Gly Arg Cys Gly Gln
1               5                   10

<210> SEQ ID NO 546
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 546

Cys Arg Asn Cys Asn Gly Arg Cys Glu Gly
1               5                   10

<210> SEQ ID NO 547
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 547
```

Cys Val Leu Cys Asn Gly Arg Cys Trp Ser
1               5                   10

<210> SEQ ID NO 548
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 548

Cys Val Thr Cys Asn Gly Arg Cys Arg Val
1               5                   10

<210> SEQ ID NO 549
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 549

Cys Thr Glu Cys Asn Gly Arg Cys Gln
1               5

<210> SEQ ID NO 550
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 550

Cys Arg Thr Cys Asn Gly Arg Cys Leu Glu
1               5                   10

<210> SEQ ID NO 551
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 551

Cys Glu Thr Cys Asn Gly Arg Cys Val Gly
1               5                   10

<210> SEQ ID NO 552
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 552

Cys Ala Val Cys Asn Gly Arg Cys Gly Phe
1               5                   10

<210> SEQ ID NO 553
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 553

Cys Ser Cys Cys Asn Gly Arg Cys Gly Asp

```
<210> SEQ ID NO 554
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 554

Cys Trp Gly Cys Asn Gly Arg Cys Arg Met
1               5                   10

<210> SEQ ID NO 555
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 555

Cys Pro Leu Cys Asn Gly Arg Cys Ala Arg
1               5                   10

<210> SEQ ID NO 556
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 556

Cys Lys Ser Cys Asn Gly Arg Cys Leu Ala
1               5                   10

<210> SEQ ID NO 557
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 557

Cys Val Pro Cys Asn Gly Arg Cys His Glu
1               5                   10

<210> SEQ ID NO 558
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 558

Cys Gln Ser Cys Asn Gly Arg Cys Val Arg
1               5                   10

<210> SEQ ID NO 559
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 559

Cys Arg Thr Cys Asn Gly Arg Cys Gln Val
1               5                   10
```

```
<210> SEQ ID NO 560
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 560

Cys Val Gln Cys Asn Gly Arg Cys Ala Leu
1               5                   10

<210> SEQ ID NO 561
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 561

Cys Arg Cys Cys Asn Gly Arg Cys Ser Pro
1               5                   10

<210> SEQ ID NO 562
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 562

Cys Ala Ser Asn Asn Gly Arg Val Val Leu
1               5                   10

<210> SEQ ID NO 563
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 563

Cys Gly Arg Cys Asn Gly Arg Cys Leu Leu
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 564

Cys Trp Leu Cys Asn Gly Arg Cys Gly Arg
1               5                   10

<210> SEQ ID NO 565
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 565

Cys Ser Lys Cys Asn Gly Arg Cys Gly His
1               5                   10
```

<210> SEQ ID NO 566
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 566

Cys Val Trp Cys Asn Gly Arg Cys Gly Leu
1               5                   10

<210> SEQ ID NO 567
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 567

Cys Ile Arg Cys Asn Gly Arg Cys Ser Val
1               5                   10

<210> SEQ ID NO 568
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 568

Cys Gly Glu Cys Asn Gly Arg Cys Val Glu
1               5                   10

<210> SEQ ID NO 569
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 569

Cys Glu Gly Val Asn Gly Arg Arg Leu Arg
1               5                   10

<210> SEQ ID NO 570
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 570

Cys Leu Ser Cys Asn Gly Arg Cys Pro Ser
1               5                   10

<210> SEQ ID NO 571
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 571

Cys Glu Val Cys Asn Gly Arg Cys Ala Leu
1               5                   10

```
<210> SEQ ID NO 572
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 572

Gly Arg Ser Gln Met Gln Ile
1               5

<210> SEQ ID NO 573
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 573

His His Thr Arg Phe Val Ser
1               5

<210> SEQ ID NO 574
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 574

Ser Lys Gly Leu Arg His Arg
1               5

<210> SEQ ID NO 575
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 575

Val Ala Ser Val Ser Val Ala
1               5

<210> SEQ ID NO 576
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 576

Trp Arg Val Leu Ala Ala Phe
1               5

<210> SEQ ID NO 577
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 577

Lys Met Gly Pro Lys Val Trp
1               5

<210> SEQ ID NO 578
```

```
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 578

Ile Phe Ser Gly Ser Arg Glu
1               5

<210> SEQ ID NO 579
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 579

Ser Pro Gly Ser Trp Thr Trp
1               5

<210> SEQ ID NO 580
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 580

Asn Pro Arg Trp Phe Trp Asp
1               5

<210> SEQ ID NO 581
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 581

Gly Arg Trp Tyr Lys Trp Ala
1               5

<210> SEQ ID NO 582
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 582

Ile Lys Ala Arg Ala Ser Pro
1               5

<210> SEQ ID NO 583
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 583

Ser Gly Trp Cys Tyr Arg Cys
1               5

<210> SEQ ID NO 584
<211> LENGTH: 7
```

<212> TYPE: PRT
<213> ORGANISM: Artificial Sequence
<220> FEATURE:
<223> OTHER INFORMATION: Synthetic Sequence

<400> SEQUENCE: 584

Ala Leu Val Gly Leu Met Arg
1               5

<210> SEQ ID NO 585
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 585

Leu Trp Ala Glu Met Thr Gly
1               5

<210> SEQ ID NO 586
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 586

Cys Trp Ser Gly Val Asp Cys
1               5

<210> SEQ ID NO 587
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 587

Asp Thr Leu Arg Leu Arg Ile
1               5

<210> SEQ ID NO 588
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 588

Ser Lys Ser Ser Gly Val Ser
1               5

<210> SEQ ID NO 589
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 589

Ile Val Ala Asp Tyr Gln Arg
1               5

<210> SEQ ID NO 590
<211> LENGTH: 7
<212> TYPE: PRT

```
<213> ORGANISM: Artificial Sequence
<220> FEATURE:
<223> OTHER INFORMATION: Synthetic Sequence

<400> SEQUENCE: 590

Val Trp Arg Thr Gly His Leu
1               5

<210> SEQ ID NO 591
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 591

Val Val Asp Arg Phe Pro Asp
1               5

<210> SEQ ID NO 592
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 592

Leu Ser Met Phe Thr Arg Pro
1               5

<210> SEQ ID NO 593
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 593

Gly Leu Pro Val Lys Trp Ser
1               5

<210> SEQ ID NO 594
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 594

Ile Met Tyr Pro Gly Trp Leu
1               5

<210> SEQ ID NO 595
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 595

Cys Val Met Val Arg Asp Gly Asp Cys
1               5

<210> SEQ ID NO 596
<211> LENGTH: 7
<212> TYPE: PRT
<213> ORGANISM: Artificial Sequence
```

```
<220> FEATURE:
<223> OTHER INFORMATION: Synthetic Sequence

<400> SEQUENCE: 596

Cys Val Arg Ile Arg Pro Cys
1               5

<210> SEQ ID NO 597
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 597

Cys Gln Leu Ala Ala Val Cys
1               5

<210> SEQ ID NO 598
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 598

Cys Gly Val Gly Ser Ser Cys
1               5

<210> SEQ ID NO 599
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 599

Cys Val Ser Gly Pro Arg Cys
1               5

<210> SEQ ID NO 600
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 600

Cys Gly Leu Ser Asp Ser Cys
1               5

<210> SEQ ID NO 601
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 601

Cys Gly Glu Gly His Pro Cys
1               5

<210> SEQ ID NO 602
<211> LENGTH: 7
<212> TYPE: PRT
<213> ORGANISM: Artificial Sequence
<220> FEATURE:
```

```
<223> OTHER INFORMATION: Synthetic Sequence

<400> SEQUENCE: 602

Cys Tyr Thr Ala Asp Pro Cys
1               5

<210> SEQ ID NO 603
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 603

Cys Glu Leu Ser Leu Ile Ser Lys Cys
1               5

<210> SEQ ID NO 604
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 604

Cys Pro Glu His Arg Ser Leu Val Cys
1               5

<210> SEQ ID NO 605
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 605

Cys Leu Val Val His Glu Ala Ala Cys
1               5

<210> SEQ ID NO 606
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 606

Cys Tyr Val Glu Leu His Cys
1               5

<210> SEQ ID NO 607
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 607

Cys Trp Arg Lys Phe Tyr Cys
1               5

<210> SEQ ID NO 608
<211> LENGTH: 7
<212> TYPE: PRT
<213> ORGANISM: Artificial Sequence
<220> FEATURE:
<223> OTHER INFORMATION: Synthetic Sequence
```

<400> SEQUENCE: 608

Cys Phe Trp Pro Asn Arg Cys
1               5

<210> SEQ ID NO 609
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 609

Cys Tyr Ser Tyr Phe Leu Ala Cys
1               5

<210> SEQ ID NO 610
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 610

Cys Pro Arg Gly Ser Arg Cys
1               5

<210> SEQ ID NO 611
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 611

Cys Arg Leu Gly Ile Ala Cys
1               5

<210> SEQ ID NO 612
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 612

Cys Asp Asp Ser Trp Lys Cys
1               5

<210> SEQ ID NO 613
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 613

Cys Ala Gln Leu Leu Gln Val Ser Cys
1               5

<210> SEQ ID NO 614
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 614

Cys Tyr Pro Ala Asp Pro Cys
1               5

<210> SEQ ID NO 615
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 615

Cys Lys Ala Leu Ser Gln Ala Cys
1               5

<210> SEQ ID NO 616
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 616

Cys Thr Asp Tyr Val Arg Cys
1               5

<210> SEQ ID NO 617
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 617

Cys Gly Glu Thr Met Arg Cys
1               5

<210> SEQ ID NO 618
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 618

Cys Leu Ser Gly Ser Leu Ser Cys
1               5

<210> SEQ ID NO 619
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 619

Trp Gly Thr Gly Leu Cys
1               5

<210> SEQ ID NO 620
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 620

```
Gly Ile Cys Lys Asp Asp Trp Cys Gln
1               5
```

<210> SEQ ID NO 621
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 621

```
Thr Ser Cys Asp Pro Ser Leu Cys Glu
1               5
```

<210> SEQ ID NO 622
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 622

```
Lys Gly Cys Gly Thr Arg Gln Cys Trp
1               5
```

<210> SEQ ID NO 623
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 623

```
Tyr Arg Cys Arg Glu Val Leu Cys Gln
1               5
```

<210> SEQ ID NO 624
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 624

```
Cys Trp Gly Thr Gly Leu Cys
1               5
```

<210> SEQ ID NO 625
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 625

```
Trp Ser Cys Ala Asp Arg Thr Cys Met
1               5
```

<210> SEQ ID NO 626
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 626

Ala Gly Cys Arg Leu Lys Ser Cys Ala
1               5

<210> SEQ ID NO 627
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 627

Ser Arg Cys Lys Thr Gly Leu Cys Gln
1               5

<210> SEQ ID NO 628
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 628

Pro Ile Cys Glu Val Ser Arg Cys Trp
1               5

<210> SEQ ID NO 629
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 629

Trp Thr Cys Arg Ala Ser Trp Cys Ser
1               5

<210> SEQ ID NO 630
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 630

Gly Arg Cys Leu Leu Met Gln Cys Arg
1               5

<210> SEQ ID NO 631
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 631

Thr Glu Cys Asp Met Ser Arg Cys Met
1               5

<210> SEQ ID NO 632
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 632

Ala Arg Cys Arg Val Asp Pro Cys Val

```
1               5
```

<210> SEQ ID NO 633
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 633

```
Cys Ile Glu Gly Val Leu Gly Gly Cys
1               5
```

<210> SEQ ID NO 634
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 634

```
Cys Ser Val Ala Asn Ser Cys
1               5
```

<210> SEQ ID NO 635
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 635

```
Cys Ser Ser Thr Met Arg Cys
1               5
```

<210> SEQ ID NO 636
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 636

```
Ser Ile Asp Ser Thr Thr Phe
1               5
```

<210> SEQ ID NO 637
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 637

```
Gly Pro Ser Arg Val Gly Gly
1               5
```

<210> SEQ ID NO 638
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 638

```
Trp Trp Ser Gly Leu Glu Ala
1               5
```

<210> SEQ ID NO 639
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 639

Leu Gly Thr Asp Val Arg Gln
1               5

<210> SEQ ID NO 640
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 640

Leu Val Gly Val Arg Leu Leu
1               5

<210> SEQ ID NO 641
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 641

Gly Arg Pro Gly Asp Trp
1               5

<210> SEQ ID NO 642
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 642

Thr Val Trp Asn Pro Val Gly
1               5

<210> SEQ ID NO 643
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 643

Gly Leu Leu Leu Val Val Pro
1               5

<210> SEQ ID NO 644
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 644

Phe Ala Ala Thr Ser Ala Glu
1               5

<210> SEQ ID NO 645
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 645

Trp Cys Cys Arg Gln Phe Asn
1               5

<210> SEQ ID NO 646
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 646

Val Gly Phe Gly Lys Ala Leu
1               5

<210> SEQ ID NO 647
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 647

Asp Ser Ser Leu Arg Leu Pro
1               5

<210> SEQ ID NO 648
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 648

Lys Leu Trp Cys Ala Met Ser
1               5

<210> SEQ ID NO 649
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 649

Ser Leu Val Ser Phe Leu Gly
1               5

<210> SEQ ID NO 650
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 650

Gly Ser Phe Ala Phe Leu Val
1               5

```
<210> SEQ ID NO 651
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 651

Ile Ala Ser Val Arg Trp Ala
1               5

<210> SEQ ID NO 652
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 652

Thr Trp Gly His Leu Arg Ala
1               5

<210> SEQ ID NO 653
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 653

Gln Tyr Arg Glu Gly Leu Val
1               5

<210> SEQ ID NO 654
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 654

Gln Ser Ala Asp Arg Ser Val
1               5

<210> SEQ ID NO 655
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 655

Tyr Met Phe Trp Thr Ser Arg
1               5

<210> SEQ ID NO 656
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 656

Leu Val Arg Arg Trp Tyr Leu
1               5

<210> SEQ ID NO 657
```

```
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 657

Thr Ala Arg Gly Ser Ser Arg
1               5

<210> SEQ ID NO 658
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 658

Thr Thr Arg Glu Lys Asn Leu
1               5

<210> SEQ ID NO 659
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 659

Pro Lys Trp Leu Leu Phe Ser
1               5

<210> SEQ ID NO 660
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 660

Leu Arg Thr Asn Val Val His
1               5

<210> SEQ ID NO 661
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 661

Ala Val Met Gly Leu Ala Ala
1               5

<210> SEQ ID NO 662
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 662

Val Arg Asn Ser Leu Arg Asn
1               5

<210> SEQ ID NO 663
<211> LENGTH: 9
```

```
<212> TYPE: PRT
<213> ORGANISM: Artificial Sequence
<220> FEATURE:
<223> OTHER INFORMATION: Synthetic Sequence

<400> SEQUENCE: 663

Thr Asp Cys Thr Pro Ser Arg Cys Thr
1               5

<210> SEQ ID NO 664
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 664

Ser Trp Cys Gln Phe Glu Lys Cys Leu
1               5

<210> SEQ ID NO 665
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 665

Val Pro Cys Arg Phe Lys Gln Cys Trp
1               5

<210> SEQ ID NO 666
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 666

Cys Thr Ala Met Arg Asn Thr Asp Cys
1               5

<210> SEQ ID NO 667
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 667

Cys Arg Glu Ser Leu Lys Asn Cys
1               5

<210> SEQ ID NO 668
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 668

Cys Met Glu Met Gly Val Lys Cys
1               5

<210> SEQ ID NO 669
<211> LENGTH: 9
<212> TYPE: PRT
```

```
<213> ORGANISM: Artificial Sequence
<220> FEATURE:
<223> OTHER INFORMATION: Synthetic Sequence

<400> SEQUENCE: 669

Val Thr Cys Arg Ser Leu Met Cys Gln
1               5

<210> SEQ ID NO 670
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 670

Cys Asn Asn Val Gly Ser Tyr Cys
1               5

<210> SEQ ID NO 671
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 671

Cys Gly Thr Arg Val Asp His Cys
1               5

<210> SEQ ID NO 672
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 672

Cys Ile Ser Leu Asp Arg Ser Cys
1               5

<210> SEQ ID NO 673
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 673

Cys Ala Met Val Ser Met Glu Asp
1               5

<210> SEQ ID NO 674
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 674

Cys Tyr Leu Gly Val Ser Asn Cys
1               5

<210> SEQ ID NO 675
<211> LENGTH: 8
<212> TYPE: PRT
<213> ORGANISM: Artificial Sequence
```

<220> FEATURE:
<223> OTHER INFORMATION: Synthetic Sequence

<400> SEQUENCE: 675

Cys Tyr Leu Val Asn Val Asp Cys
1               5

<210> SEQ ID NO 676
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 676

Cys Ile Arg Ser Ala Val Ser Cys
1               5

<210> SEQ ID NO 677
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 677

Leu Val Cys Leu Pro Pro Ser Cys Glu
1               5

<210> SEQ ID NO 678
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 678

Arg His Cys Phe Ser Gln Trp Cys Ser
1               5

<210> SEQ ID NO 679
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 679

Phe Tyr Cys Pro Gly Val Gly Cys Arg
1               5

<210> SEQ ID NO 680
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 680

Ile Ser Cys Ala Val Asp Ala Cys
1               5

<210> SEQ ID NO 681
<211> LENGTH: 9
<212> TYPE: PRT
<213> ORGANISM: Artificial Sequence
<220> FEATURE:

<223> OTHER INFORMATION: Synthetic Sequence

<400> SEQUENCE: 681

Glu Ala Cys Glu Met Ala Gly Cys Leu
1               5

<210> SEQ ID NO 682
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 682

Pro Arg Cys Glu Ser Gln Leu Cys Pro
1               5

<210> SEQ ID NO 683
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 683

Arg Ser Cys Ile Lys His Gln Cys Pro
1               5

<210> SEQ ID NO 684
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 684

Gln Trp Cys Ser Arg Arg Trp Cys Thr
1               5

<210> SEQ ID NO 685
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 685

Met Phe Cys Arg Met Arg Ser Cys Asp
1               5

<210> SEQ ID NO 686
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 686

Gly Ile Cys Lys Asp Leu Trp Cys Gln
1               5

<210> SEQ ID NO 687
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 687

Asn Ala Cys Glu Ser Ala Ile Cys Gly
1               5

<210> SEQ ID NO 688
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 688

Ala Pro Cys Gly Leu Leu Ala Cys Ile
1               5

<210> SEQ ID NO 689
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 689

Asn Arg Cys Arg Gly Val Ser Cys Thr
1               5

<210> SEQ ID NO 690
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 690

Phe Pro Cys Glu Gly Lys Lys Cys Leu
1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 691

Ala Asp Cys Arg Gln Lys Pro Cys Leu
1               5

<210> SEQ ID NO 692
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 692

Phe Gly Cys Val Met Ala Ser Cys Arg
1               5

<210> SEQ ID NO 693
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 693

Ala Gly Cys Ile Asn Gly Leu Cys Gly
1               5

<210> SEQ ID NO 694
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 694

Arg Ser Cys Ala Glu Pro Trp Cys Tyr
1               5

<210> SEQ ID NO 695
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 695

Asp Thr Cys Arg Ala Leu Arg Cys Asn
1               5

<210> SEQ ID NO 696
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 696

Lys Gly Cys Gly Thr Arg Gln Cys Trp
1               5

<210> SEQ ID NO 697
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 697

Gly Arg Cys Val Asp Gly Gly Cys Thr
1               5

<210> SEQ ID NO 698
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 698

Tyr Arg Cys Ile Ala Arg Glu Cys Glu
1               5

<210> SEQ ID NO 699
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 699

Lys Arg Cys Ser Ser Ser Leu Cys Ala
1               5

<210> SEQ ID NO 700
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 700

Ile Cys Leu Leu Ala His Cys Ala
1               5

<210> SEQ ID NO 701
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 701

Gln Ala Cys Pro Met Leu Leu Cys Met
1               5

<210> SEQ ID NO 702
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 702

Leu Asp Cys Leu Ser Glu Leu Cys Ser
1               5

<210> SEQ ID NO 703
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 703

Ala Gly Cys Arg Val Glu Ser Cys
1               5

<210> SEQ ID NO 704
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 704

His Thr Cys Leu Val Ala Leu Cys Ala
1               5

<210> SEQ ID NO 705
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 705

Ile Tyr Cys Pro Gly Gln Glu Cys Glu
1               5

<210> SEQ ID NO 706
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 706

Arg Leu Cys Ser Leu Tyr Gly Cys Val
1               5

<210> SEQ ID NO 707
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 707

Arg Lys Cys Glu Val Pro Gly Cys Gln
1               5

<210> SEQ ID NO 708
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 708

Glu Asp Cys Thr Ser Arg Phe Cys Ser
1               5

<210> SEQ ID NO 709
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 709

Leu Glu Cys Val Val Asp Ser Cys Arg
1               5

<210> SEQ ID NO 710
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 710

Glu Ile Cys Val Asp Gly Leu Cys Val
1               5

<210> SEQ ID NO 711
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 711

Arg Trp Cys Arg Glu Lys Ser Cys Trp

```
<210> SEQ ID NO 712
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 712

Phe Arg Cys Leu Glu Arg Val Cys Thr
1               5

<210> SEQ ID NO 713
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 713

Arg Pro Cys Gly Asp Gln Ala Cys Glu
1               5

<210> SEQ ID NO 714
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 714

Cys Asn Lys Thr Asp Gly Asp Glu Gly Val Thr Cys
1               5                   10

<210> SEQ ID NO 715
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 715

Pro Gln Arg Arg Ser Ala Arg Leu Ser Ala
1               5                   10

<210> SEQ ID NO 716
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 716

Ile Glu Leu Leu Gln Ala Arg
1               5

<210> SEQ ID NO 717
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 717

Ile Ser Leu Leu Gln Ala Arg
1               5
```

<210> SEQ ID NO 718
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 718

Ile Asp Leu Met Gln Ala Arg
1               5

<210> SEQ ID NO 719
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 719

Ile Ile Leu Leu Gln Gly Arg
1               5

<210> SEQ ID NO 720
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 720

Ile Ser Leu Leu Gly Ala Arg
1               5

<210> SEQ ID NO 721
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 721

Phe Ser Leu Leu Asp Ala Arg
1               5

<210> SEQ ID NO 722
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 722

Cys Thr Pro Ser Pro Phe Ser His Cys
1               5

<210> SEQ ID NO 723
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 723

Ala Gly Thr Arg Met Ser Trp Glu Val
1               5

<210> SEQ ID NO 724
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 724

Cys Ser Asn Arg Asp Ala Arg Arg Cys
1               5

<210> SEQ ID NO 725
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 725

Trp Gln Pro Asp Thr Ala His His Trp Ala Thr Leu
1               5                   10

<210> SEQ ID NO 726
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 726

His Asn Ala Tyr Trp His Trp Pro Pro Ser Met Thr
1               5                   10

<210> SEQ ID NO 727
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 727

Gly His Leu Ile Pro Leu Arg Gln Pro Ser His
1               5                   10

<210> SEQ ID NO 728
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 728

Tyr Thr Ser Pro His His Ser Thr Thr Gly His Leu
1               5                   10

<210> SEQ ID NO 729
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 729

Trp Thr His His His Ser Tyr Pro Arg Pro Leu
1               5                   10

```
<210> SEQ ID NO 730
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 730

Asn Ser Phe Pro Leu Met Leu Met His His His Pro
1               5                   10

<210> SEQ ID NO 731
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 731

Lys His Met His Trp His Pro Pro Ala Leu Asn
1               5                   10

<210> SEQ ID NO 732
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 732

Ser Leu Asp Ser Met Ser Pro Gln Trp His Ala Asp
1               5                   10

<210> SEQ ID NO 733
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 733

Ser Glu Phe Ile His His Trp Thr Pro Pro Pro Ser
1               5                   10

<210> SEQ ID NO 734
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 734

Asn Gly Phe Ser His His Ala Pro Leu Met Arg Tyr
1               5                   10

<210> SEQ ID NO 735
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 735

His His Glu Trp Thr His His Trp Pro Pro Pro
1               5                   10

<210> SEQ ID NO 736
```

```
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 736

Ala Trp Pro Glu Asn Pro Ser Arg Arg Pro Phe
1               5                   10

<210> SEQ ID NO 737
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 737

Ala Gly Phe Gln His His Pro Ser Phe Tyr Arg Phe
1               5                   10

<210> SEQ ID NO 738
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 738

Gln Arg Ser Pro Met Met Ser Arg Ile Arg Leu Pro
1               5                   10

<210> SEQ ID NO 739
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 739

Tyr Arg His Trp Pro Ile Asp Tyr Pro Pro Pro
1               5                   10

<210> SEQ ID NO 740
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 740

Met Ile His Thr Asn His Trp Trp Ala Gln Asp
1               5                   10

<210> SEQ ID NO 741
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 741

Cys Ala Leu Ile Ile Gln Lys Asn Glu Cys
1               5                   10

<210> SEQ ID NO 742
<211> LENGTH: 10
```

```
<212> TYPE: PRT
<213> ORGANISM: Artificial Sequence
<220> FEATURE:
<223> OTHER INFORMATION: Synthetic Sequence

<400> SEQUENCE: 742

Cys Gly Leu Ile Leu Gln Lys Asn Glu Cys
1               5                   10

<210> SEQ ID NO 743
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 743

Cys Gly Leu Ile Ile Gln Arg Asn Glu Cys
1               5                   10

<210> SEQ ID NO 744
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 744

Cys Gly Leu Ile Ile Asn Lys Asn Glu Cys
1               5                   10

<210> SEQ ID NO 745
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 745

Cys Asn Ala Ala Glu Ser Ser Lys Asn Cys
1               5                   10

<210> SEQ ID NO 746
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 746

Cys Asn Ala Gly Glu Ser Ser Arg Asn Cys
1               5                   10

<210> SEQ ID NO 747
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 747

Cys Asn Ala Gly Glu Ser Thr Lys Asn Cys
1               5                   10

<210> SEQ ID NO 748
<211> LENGTH: 10
<212> TYPE: PRT
```

<213> ORGANISM: Artificial Sequence
<220> FEATURE:
<223> OTHER INFORMATION: Synthetic Sequence

<400> SEQUENCE: 748

Cys Asn Ala Gly Asp Ser Ser Lys Asn Cys
1               5                   10

<210> SEQ ID NO 749
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 749

Cys Leu Ser Asp Gly Lys
1               5

<210> SEQ ID NO 750
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 750

Cys Leu Ser Asp Gly Lys Pro Val Ser
1               5

<210> SEQ ID NO 751
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 751

Cys Ser Met Ser Ala Lys Lys Lys Cys
1               5

<210> SEQ ID NO 752
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 752

Cys Lys Thr Arg Val Ser Cys Gly Val
1               5

<210> SEQ ID NO 753
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 753

Cys Ala Ser Leu Ser Cys Arg
1               5

<210> SEQ ID NO 754
<211> LENGTH: 9
<212> TYPE: PRT
<213> ORGANISM: Artificial Sequence

```
<220> FEATURE:
<223> OTHER INFORMATION: Synthetic Sequence

<400> SEQUENCE: 754

Cys Ser Gly Gly Lys Val Leu Asp Cys
1               5

<210> SEQ ID NO 755
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 755

Cys Ala Ser Leu Ser Cys Arg
1               5

<210> SEQ ID NO 756
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 756

Cys Ser Gly Gly Lys Val Leu Asp Cys
1               5

<210> SEQ ID NO 757
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 757

Cys Ser Met Ser Ala Lys Lys Lys Cys
1               5

<210> SEQ ID NO 758
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 758

Cys Lys Thr Arg Val Ser Cys Gly Val
1               5

<210> SEQ ID NO 759
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 759

Cys Ala Ser Leu Ser Cys Arg
1               5

<210> SEQ ID NO 760
<211> LENGTH: 8
<212> TYPE: PRT
<213> ORGANISM: Artificial Sequence
<220> FEATURE:
```

```
<223> OTHER INFORMATION: Synthetic Sequence

<400> SEQUENCE: 760

Trp Ile Phe Pro Trp Ile Gln Leu
1               5

<210> SEQ ID NO 761
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 761

Trp Asp Leu Ala Trp Met Phe Arg Leu Pro Val Gly
1               5                   10

<210> SEQ ID NO 762
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 762

Cys Arg Gly Ser Gly Ala Gly Arg Cys
1               5

<210> SEQ ID NO 763
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 763

Cys Lys Gly Gly Arg Ala Lys Asp Cys
1               5

<210> SEQ ID NO 764
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 764

Cys Gly Ser Pro Gly Trp Val Arg Cys
1               5

<210> SEQ ID NO 765
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 765

Val Gly Val Gly Glu Trp Ser Val
1               5

<210> SEQ ID NO 766
<211> LENGTH: 5
<212> TYPE: PRT
<213> ORGANISM: Artificial Sequence
<220> FEATURE:
<223> OTHER INFORMATION: Synthetic Sequence
```

<400> SEQUENCE: 766

Ser Arg Pro Arg Arg
1               5

<210> SEQ ID NO 767
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: is any amino acid

<400> SEQUENCE: 767

Cys Xaa Ser Arg Pro Arg Arg Glx Cys
1               5

<210> SEQ ID NO 768
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 768

Cys Ser Arg Pro Arg Arg Ser Val Cys
1               5

<210> SEQ ID NO 769
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 769

Cys Ser Arg Pro Arg Arg Ser Trp Cys
1               5

<210> SEQ ID NO 770
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 770

Cys Gly Leu Ser Gly Leu Gly Val Ala
1               5

<210> SEQ ID NO 771
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 771

Cys Pro Ile Arg Pro Met Glu Asp Cys
1               5

<210> SEQ ID NO 772
<211> LENGTH: 9
<212> TYPE: PRT

<213> ORGANISM: Artificial Sequence
<220> FEATURE:
<223> OTHER INFORMATION: Synthetic Sequence

<400> SEQUENCE: 772

Cys Pro Ile Asp Glu Arg Pro Met Cys
1               5

<210> SEQ ID NO 773
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 773

Cys Ala Leu Arg Asp Arg Pro Met Cys
1               5

<210> SEQ ID NO 774
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 774

Cys Pro Glu Lys Phe Arg Pro Met Cys
1               5

<210> SEQ ID NO 775
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 775

Cys Ser Pro Gln Ser Gln Pro Met Cys
1               5

<210> SEQ ID NO 776
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 776

Cys Gly Leu Ile Ile Gln Lys Asn Glu Cys
1               5                   10

<210> SEQ ID NO 777
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 777

Cys Arg Gly Asp Lys
1               5

<210> SEQ ID NO 778
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 778

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 779
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 779

Cys Gly Gln Lys Arg Thr Arg Gly Cys
1               5

<210> SEQ ID NO 780
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 780

Asn Val Val Arg Gln
1               5

<210> SEQ ID NO 781
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 781

Pro His Ser Cys Asn Lys
1               5

<210> SEQ ID NO 782
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 782

His Pro Leu Ser Lys His Pro Tyr Trp Ser Gln Pro
1               5                   10

<210> SEQ ID NO 783
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 783

Ile Phe Leu Leu Trp Gln Arg
1               5

<210> SEQ ID NO 784
<211> LENGTH: 5

```
<212> TYPE: PRT
<213> ORGANISM: Artificial Sequence
<220> FEATURE:
<223> OTHER INFORMATION: Synthetic Sequence

<400> SEQUENCE: 784

Ala Pro Arg Pro Gly
1               5

<210> SEQ ID NO 785
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 785

Cys Arg Gly Asp Arg Cys Pro Asp Cys
1               5

<210> SEQ ID NO 786
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 786

Cys Val Asn His Pro Ala Phe Ala Cys
1               5

<210> SEQ ID NO 787
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 787

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 788
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 788

Cys Gly Lys Arg Lys
1               5

<210> SEQ ID NO 789
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 789

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys Cys
```

```
<210> SEQ ID NO 790
<211> LENGTH: 54
<212> TYPE: DNA
<213> ORGANISM: Artificial Sequence
<220> FEATURE:
<223> OTHER INFORMATION: Synthetic sequence

<400> SEQUENCE: 790
cagctgggca aaaaaaaaca tcgccgccgc ccgagcaaaa aaaaacgcca ttgg          54

<210> SEQ ID NO 791
<211> LENGTH: 54
<212> TYPE: DNA
<213> ORGANISM: Artificial Sequence
<220> FEATURE:
<223> OTHER INFORMATION: Synthetic sequence

<400> SEQUENCE: 791
cagctgggcg cggcggcgca tcgccgccgc ccgagcaaaa aaaaacgcca ttgg          54

<210> SEQ ID NO 792
<211> LENGTH: 54
<212> TYPE: DNA
<213> ORGANISM: Artificial Sequence
<220> FEATURE:
<223> OTHER INFORMATION: Synthetic sequence

<400> SEQUENCE: 792
cagctgggcc gccgccgcca tcgccgccgc ccgagccgcc gccgccgcca ttgg          54

<210> SEQ ID NO 793
<211> LENGTH: 54
<212> TYPE: DNA
<213> ORGANISM: Artificial Sequence
<220> FEATURE:
<223> OTHER INFORMATION: Synthetic sequence

<400> SEQUENCE: 793
cagctgggca aaaaaattct ggcggcgcgc ccgagcaaaa aaaaacgcca ttgg          54

<210> SEQ ID NO 794
<211> LENGTH: 36
<212> TYPE: DNA
<213> ORGANISM: Artificial Sequence
<220> FEATURE:
<223> OTHER INFORMATION: Synthetic sequence

<400> SEQUENCE: 794
catcgccgcc gcccgagcaa aaaaaaacgc cattgg                              36

<210> SEQ ID NO 795
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 795

His Leu Tyr Val Ser Pro Trp
1               5

<210> SEQ ID NO 796
<211> LENGTH: 9
<212> TYPE: PRT
```

```
<213> ORGANISM: Artificial Sequence
<220> FEATURE:
<223> OTHER INFORMATION: Synthetic Sequence

<400> SEQUENCE: 796

Cys Gly Phe Tyr Trp Leu Arg Ser Cys
1               5

<210> SEQ ID NO 797
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 797

Cys Gln Asp Gly Arg Met Gly Phe Cys
1               5

<210> SEQ ID NO 798
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 798

Ala Ala Val Ala Leu Leu Pro Ala Val Leu Leu Ala Leu Leu Ala Pro
1               5                   10                  15
```

CYTOTOXIC HEXIM1 PEPTIDES AND USES THEREOF

CROSS-REFERENCE TO RELATED APPLICATIONS

This patent application is a U.S. National Phase Application under 35 U.S.C. § 371 of International Application No. PCT/SG2016/050101, filed on 3 Mar. 2016, entitled CYTOTOXIC HEXIM1 PEPTIDES AND USES THEREOF, which claims priority to Singapore provisional application Nos. 10201501642V filed on 4 Mar. 2015 and 10201504803T filed on 17 Jun. 2015, the contents of which were incorporated by reference in their entirety for all purposes.

INCORPORATION BY REFERENCE

This application incorporates by reference the material (i.e., Sequence Listing) in the ASCII text file named 9869SG3622 corrected ST25_3868247_1.txt, created on Jan. 4, 2018, having a file size of 172,132 bytes.

FIELD OF THE INVENTION

The present invention generally relates to the field of biochemistry. In particular, the present invention relates to cytotoxic peptides, compositions containing cytotoxic peptides and the use of the peptides and compositions in the prevention and treatment of cancers.

BACKGROUND OF THE INVENTION

Cancer is the second leading cause of death worldwide, accounting for 8.2 million deaths in 2012. It is expected that annual cancer cases will rise from 14 million in 2012 to 22 million within the next two decades.

Conventional treatments for cancer using radiation or chemotherapeutic drugs target rapidly proliferating cells and induce such cells to undergo apoptosis. Most chemotherapeutic agents exhibit some degree of toxicity toward normal cells at therapeutic doses, causing undesired side effects that may be dose limiting, thereby reducing the usefulness of the drugs. Furthermore, these traditional methods of treatment are not successful in treating many types of cancers, particularly those that are resistant to apoptotic stimuli. Since the cytotoxic agents in most chemotherapeutic drugs act primarily through p53-dependent induction of apoptosis, and p53 is often mutated in cancers cells, resistance to chemotherapy is often observed in cancer patients. As a consequence, there is an ongoing need for new therapeutic agents that are more effective in treating cancers.

SUMMARY OF THE INVENTION

In one aspect, the present invention refers to an isolated cytotoxic peptide having sequence identity of at least 66% to SEQ ID NO: 3 or functional part thereof.

In another aspect, the present invention refers to an isolated cytotoxic peptide comprising at least one amino acid sequence represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36), or functional part thereof, wherein X is any amino acid.

In one aspect, the present invention refers to an isolated nucleic acid molecule comprising the nucleotide sequence encoding the isolated cytotoxic peptide as described herein.

In another aspect, the present invention refers to a vector comprising the isolated nucleic acid molecule as described herein.

In another aspect, the present invention refers to a pharmaceutical composition comprising the isolated cytotoxic peptide or conjugate thereof, the isolated nucleic acid molecule, or the vector as described herein.

In yet another aspect, the present invention refers to a method of treating or preventing cancer in a subject, comprising administering the isolated cytotoxic peptide or conjugate thereof, the isolated nucleic acid molecule, the vector or the pharmaceutical composition as described herein.

In one aspect, the present invention refers to a method of eliminating undifferentiated stem cells in a subject having stem cell transplantation, comprising administering the isolated cytotoxic peptide or conjugate thereof, the isolated nucleic acid molecule, the vector or the pharmaceutical composition as described herein.

In another aspect, the present invention refers to a method of treating or preventing obesity in a subject, comprising administering the isolated cytotoxic peptide or conjugate thereof, the isolated nucleic acid molecule, the vector or the pharmaceutical composition as described herein.

BRIEF DESCRIPTION OF THE DRAWINGS

The invention will be better understood with reference to the detailed description when considered in conjunction with the non-limiting examples and the accompanying drawings, in which:

FIG. 1 shows FGF-tagged BR peptide (SEQ ID NO: 19) and FGF-tagged mutant BR peptides induce cell death in various cell lines. FGF tag is a cell membrane-translocating peptide derived from Kaposi fibroblast growth factor. (A) Alignment of the HDM2 ubiquitination sites of p53 (amino acids (AAs) 370-386, SEQ ID NO: 34) and HEXIM1 (AAs 150-161, SEQ ID NO: 35) shows that ubiquitin sites of p53 and HEXIM1 exhibit similar distribution of the lysine residues (the HDM2-ubiquitinated lysine residues are underlined). (B) Alignment of wild-type and mutant HEXIM1 BR peptides (RRR12 and ILAA) indicates the amino acid residues that have been mutated (the mutated residues are underlined). (C) Cell viability plots showing the effects of FGF-tagged BR peptide in various cancer cell lines. Cancer cell lines: Acute Myeloid Leukemia cell lines—AML2, AML3, cervical cancer cell line—HeLa, and non-cancer cell lines—Human Embryonic Kidney 293 (293) and Human Foreskin Fibroblast (HFF) cell lines were treated overnight with various concentrations of indicated FGF-fused peptides before cell viability was determined by Cell-Titer Glo assays. Cells treated with the FGF-X13 peptide (SEQ ID NO: 18) were used as a negative control. The results show that FGF-tagged BR peptide induces cell death in AML2, AML3, HeLa, HEK293 and HFF cell lines. (D) Cell viability plots showing the effects of FGF-tagged BR peptide and variants thereof in human colon cancer cell line HCT116 with wild-type p53 (p53 WT) or p53 knockout (p53KO). HCT116 (p53 WT) and HCT116 (p53 KO) cells were treated with FGF-X13, FGF-BR, FGF-BR-RRR12 (SEQ ID NO: 20) and FGF-BR-ILAA (SEQ ID NO: 21) peptides at various concentrations overnight before cell viability assays were performed. Data representative of at least three independent experiments performed in triplicate were shown with values expressed as mean±SD. The results indicate that FGF-tagged BR peptide shows similar level of cytotoxicity in HCT116 p53 wild-type (p53 WT) and HCT116 p53 knockout (p53 KO) cell lines. FGF-tagged mutant BR peptides, BR(RRR12) and BR(ILAA) also show cytotoxicity in both HCT116 (p53 WT) and HCT116 (p53KO) cell lines.

The results indicate that LTV-tagged BR peptide requires all three stretches of basic residues (KKK, RRR and KKK) to establish full potency in cell killing.

FIG. 8 shows cell viability plots (upper panel) of cells treated control, LTV-tagged BR and alanine substituted variants thereof (sequences indicated in the lower panel). MDA-MB-231 breast cancer cells were treated with indicated alanine-substituted LTV-tagged peptides at 10 μM and 30 μM overnight before cell viability assays were performed. Cells treated with LTV-X13 were used as negative control, cells treated with LTV-BR were used as positive control. Data representative of at least three independent experiments performed in triplicate were shown with values expressed as mean±SD. The results indicate that alanine residue substitution in the middle and C-terminal regions of the HEXIM1 BR peptide abolished the cytotoxic activity of LTV-BR.

Figure 9:
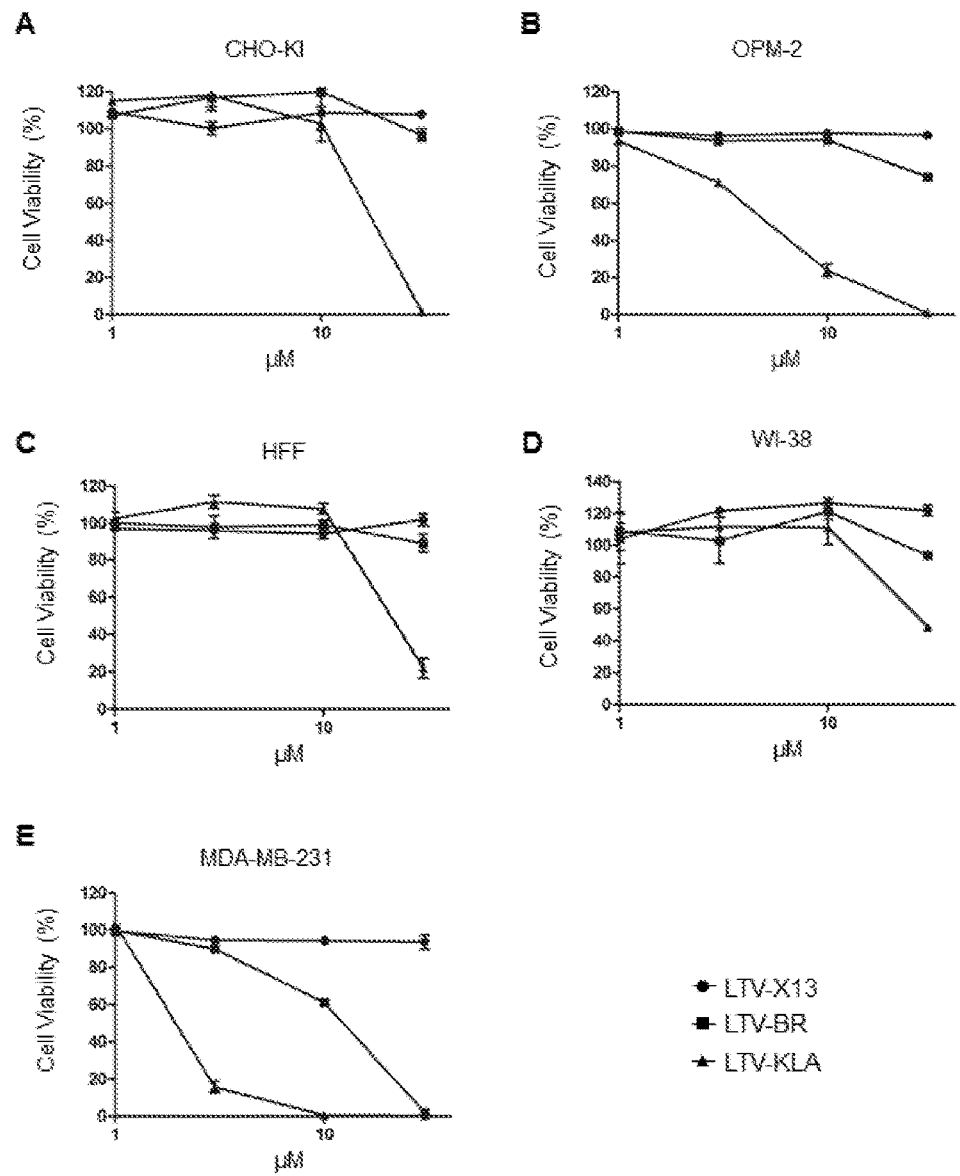

FIG. 9 shows cell viability plots of various cell lines treated with control and LTV-tagged BR and LTV-tagged KLA peptides. Chinese hamster ovary cancer cell line, CHO-K1; multiple myeloma cell line, OPM-2, human foreskin fibroblasts, HFF; and human lung fibroblasts, WI-38 were treated with indicated LTV-fused peptides at various concentrations overnight before cell viability assays were performed. Cells treated with LTV-X13 was used as a negative control. Data representative of at least three independent experiments performed in triplicate were shown with values expressed as mean±SD. The results indicate that LTV-tagged KLA peptide exhibits non-specific killing on non-breast cancer cell lines and normal human fibroblasts, while LTV-tagged BR peptide does not show such non-specific cytotoxicity.

Figure 10:
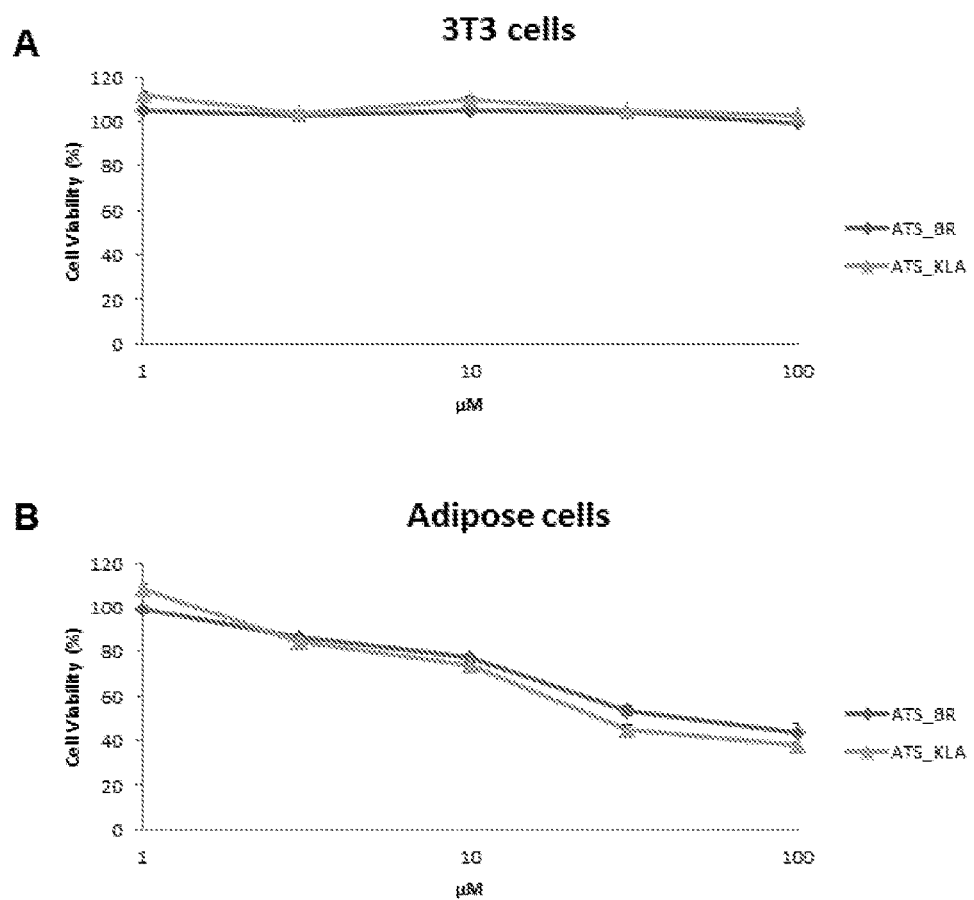

FIG. 10 shows cell viability plots of (A) undifferentiated 3T3 cells and (B) adipose cells treated with $BR_D$ and $KLA_D$ peptides tagged with lipocyte-targeting peptide, ATS (ATS-$BR_D$ and ATS-$KLA_D$ peptides). The results indicate that the ATS-$BR_D$ peptide has no cytotoxic effect on undifferentiated 3T3 mouse fibroblast cells, but has significant cytotoxic effect on differentiated adipose cells. The cytotoxic effect of ATS-$BR_D$ peptide on adipose cells is of similar potency as ATS-$KLA_D$ peptide.

FIG. 11 shows that the cytotoxic effect exerted by BR is independent of p53. AML2 and AML3 cells were treated with FGF-tagged p53 and FGF-tagged BR peptides at the indicated concentrations. Cell viability was measured 16 hours post-incubation by Cell-Titer Glo. Cells treated with vehicle, DMSO (0.5%), were used as control. (A) Cell viability plots showing the effects of FGF-tagged p53 and FGF-tagged BR peptides in AML2 cell line. (B) Cell viability plots showing the effects of FGF-tagged p53 and FGF-tagged BR peptides in AML3 cell line.

DETAILED DESCRIPTION OF THE PRESENT INVENTION

In the search for new therapeutic agents that are more effective in treating cancers, it was found that the basic region (BR) of hexamethylene bisacetamide inducible protein 1 (HEXIM1, represented by SEQ ID NO: 1) exerts its cytotoxic effects independent of the status of p53. Thus, the present disclosure provides an isolated peptide that has the cytotoxic activity of the BR of HEXIM1.

In one example, there is provided an isolated cytotoxic peptide having sequence identity of at least 66% to SEQ ID NO: 3, or functional part thereof. In some examples, the isolated cytotoxic peptide has sequence identity of at least 72%, at least 77%, at least 83%, at least 88% or at least 94% to SEQ ID NO: 3, or functional part thereof. In some other examples, the isolated cytotoxic peptide has sequence identity of 66% to 78%, 77% to 89%, 88% to 95% to SEQ ID NO: 3, or functional part thereof.

As used herein, the basic region (BR) of HEXIM refers to the region between AAs 150-180 of HEXIM1, which includes a stretch of basic residues. The BR is represented by the sequence of KKKHRRRPSKKKRHWK-PYYKLTWEEKKKFDE (SEQ ID NO: 2).

As used herein, an "isolated" peptide is intended to mean a peptide removed from its native environment, such as recombinantly produced peptides expressed in host cells and native or recombinant peptides which have been substantially purified by any suitable technique. Isolated peptides according to the present disclosure further include such compounds produced synthetically.

The terms "peptide" used herein refers to polymers of amino acid residues of any length. The polymer may be linear or branched, it may comprise modified amino acids or amino acid analogues, and it may be interrupted by chemical moieties other than amino acids. The terms also encompass an amino acid polymer that has been modified naturally or by intervention, for example disulfide bond formation, glycosylation, lipidation, acetylation, phosphorylation, or any other manipulation or modification, such as conjugation with a labelling or bioactive component. The term peptide encompasses two or more naturally occurring or synthetic amino acids linked by a covalent bond (for example, an amide bond). The peptide as disclosed herein can be of various lengths, such as having 6 to 200, 8 to 190, 10 to 180, 12 to 170, 14 to 160, 16 to 150, 18 to 140, 20 to 130, 22 to 120, 24 to 110, 26 to 100, 28 to 90, 30 to 80, 32 to 70, 34 to 60, 36 to 50 or 38 to 45 amino acid residues.

As used herein, the term "amino acid" is defined as having at least one primary, secondary, tertiary or quaternary amino group, and at least one acid group, wherein the acid group may be a carboxylic, sulfonic, or phosphoric acid, or mixtures thereof. The amino groups may be "alpha", "beta", "gamma" to "omega" with respect to the acid group(s). Suitable amino acids include, without limitation, both the D- and L-isomers of the 20 common naturally occurring amino acids found in peptides (for example, A, R, N, C, D, Q, E, G, H, I, L, K, M, F, P, S, T, W, Y, V (as known by the one-letter or three letter abbreviations)) as well as the naturally occurring and unnaturally occurring amino acids prepared by organic synthesis or other metabolic routes.

The term "sequence identity" as used herein refers to a relationship between two or more peptide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, for example, the sequences are "identical" at a particular position if at that position, the amino acid residues are identical. The total number of such position identities is then divided by the total number of amino acid residues in the reference sequence to give % sequence identity. Sequence identity can be readily calculated by known methods. Some methods used to determine the sequence identity are designed to give the largest match between the sequences tested. Methods to determine sequence identity are codified in publicly available computer programs that determine sequence identity between given sequences. These programs optimally align sequences using default gap weights in order to produce the highest level of sequence identity between the given and reference sequences. As an illustration, by a peptide or polypeptide having a given amino acid sequence having at least, for example, 66% sequence identity to a reference amino acid sequence, it is intended that the given amino acid sequence of the peptide or polypeptide is identical to the reference sequence except that the given peptide or polypeptide sequence may include up to 34 amino acid alterations per each 100 amino acids of the reference amino acid sequence. In other words, to obtain a given peptide or polypeptide sequence having at least 66% sequence identity with a reference amino acid sequence, up to 34% of the amino acid residues in the reference sequence may be deleted or substituted with another amino acid, or a number of amino acids up to 34% of the total number of amino acid residues in the reference sequence may be inserted into the reference sequence. These alterations of the reference sequence may occur at the amino or the carboxyl terminal positions of the reference amino acid sequence or anywhere between those terminal positions, interspersed either individually among residues in the reference sequence or in the one or more contiguous groups within the reference sequence. In some examples, residue positions that are not identical differ by conservative amino acid substitutions. However, conservative substitutions are not included as a match when determining sequence identity. For example, the isolated cytotoxic peptide QLGKKILAARPSKKKRHW (SEQ ID NO: 5) has 77.8% sequence identity with SEQ ID NO: 3; the isolated cytotoxic peptides QLGRRRHRRRPSKKKRHW (SEQ ID NO: 4) and HRRRPSKKKRHW (SEQ ID NO: 37) both have 66.7% sequence identity with SEQ ID NO: 3, the isolated cytotoxic peptide QLGAAAHRRRPSKKKRHW (SEQ ID NO: 38) has 83.3% sequence identity with SEQ ID NO: 3.

Thus, in some examples, the isolated cytotoxic peptide as described herein has at least 12, at least 13, at least 14, at least 15, at least 16 or at least 17 amino acid residues that are the same as SEQ ID NO: 3, or functional part thereof. In some other examples, the isolated cytotoxic peptide has 12 to 14 or 15 to 17 amino acid residues that are the same as SEQ ID NO: 3, or functional part thereof.

The terms "cytotoxic" and "cytotoxicity" as used herein refer to the effect of a compound or composition of being toxic to the cells. Effects of cytotoxicity on cells include, but are not limited to, cell swelling, cell lysis, loss of cell membrane integrity, decreased rate of metabolism, decreased cell viability, cell deaths (by inducing apoptosis or necrosis). Thus, the cytotoxic effects can be exerted via various pathways. Examples of possible pathways include, but are not limited to, apoptosis-independent pathways, positive transcription elongation factor b (P-TEFb)-independent pathway, p53-independent pathway. The terms "low toxicity" or "reduced toxicity" as used in the present disclosure refer to a decrease in toxicity towards non-cancerous cells and tissue relative or compared to cancerous cells and tissue. In some examples, the low or reduced toxicity towards non-cancerous cells and tissue is at most about 0.9 times, at most about 0.8 times, at most about 0.7 times, at most about 0.6 times, at most about 0.5 times, at most about 0.4 times, at most about 0.3 times, at most about 0.2 times, at most about 0.1 times, or at most about 0.05 times the toxicity towards cancer cells and tissue samples obtained from the same or a different subject.

The term "apoptosis" as used herein refers to programmed cell death, characterized by cell changes such as blebbing, cell shrinkage, nuclear fragmentation, chromatin condensation, chromosomal DNA fragmentation, and global mRNA decay.

As used herein, the term "functional part" of a peptide or amino acid sequence refers to the part of the peptide or the amino acid sequence that produces the overall function of a peptide or amino acid sequence. In some examples, the functional part of a peptide or amino acid sequence comprises 6 to 17, 7 to 16, 8 to 15, 9 to 14, 10 to 13 or 11 to 12 amino acid residues of the peptide or amino acid sequence. In one example, the functional part of SEQ ID NO: 3 refers to the part of SEQ ID NO: 3 that has cytotoxic effect. In some specific examples, the functional part of SEQ ID NO: 3 comprises at least six, at least seven, at least eight, at least nine, at least ten, at least eleven, at least twelve, at least thirteen, at least fourteen, at least fifteen, at least sixteen or at least seventeen amino acid residues of the peptide or amino acid sequence. In some other examples, the functional part of SEQ ID NO: 3 comprises at least the following stretches of amino acid residues RRR (AAs 8-10 of SEQ ID NO: 3) and KKK (AAs 13-15 of SEQ ID NO: 3). Thus, some examples of the isolated cytotoxic peptide as described herein comprises amino acid residues at positions corresponding to amino acids 8 to 10 and 13 to 15 of SEQ ID NO: 3. Exemplary peptides include, but are not limited to, the sequences of:

i)
(SEQ ID NO: 3)
QLGKKKHRRRPSKKKRHW;

ii)
(SEQ ID NO: 37)
HRRRPSKKKRHW;
and ii)
(SEQ ID NO: 38)
QLGAAAHRRRPSKKKRHW.

The isolated cytotoxic peptide as described above may comprise at least one amino acid sequence that can be represented by a consensus sequence. Thus, in one example, there is provided an isolated cytotoxic peptide having sequence identity of at least 66% to SEQ ID NO: 3, or functional part thereof, comprising at least one amino acid sequence represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36), or functional part thereof. In some examples, the isolated cytotoxic peptide has sequence identity of at least 72%, at least 77%, at least 83%, at least 88% or at least 94% to SEQ ID NO: 3, or functional part thereof. In some other examples, the isolated cytotoxic peptide has sequence identity of 66% to 78%, 77% to 89%, 88% to 95% to SEQ ID NO: 3, or functional part thereof.

In another example, there is provided an isolated cytotoxic peptide comprising at least one amino acid sequence represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36), or functional part thereof.

The term "consensus sequence" as used herein refers to an amino acid sequence determined by aligning a series of multiple sequences. It defines an idealized sequence that represents the predominant choice of amino acid at each corresponding position of the multiple sequences.

In some examples, $X_4$, $X_5$ and $X_6$ can be any amino acids or may be deleted. In some examples, $X_4$, $X_5$ and $X_6$ are positively charged amino acids. In some examples, $X_4$, $X_5$ and $X_6$ are the same. In some other examples, at least two of $X_4$, $X_5$ and $X_6$ are different from each other. In some examples, $X_7$ can be histidine (H) or leucine (L). In some examples, $X_8$ and $X_9$ are positively charged amino acids. In some other examples, $X_8$ and $X_9$ can be small amino acid residues including but are not limited to alanine (A). In some examples, $X_8$ and $X_9$ are the same, while in some other examples, $X_8$ and $X_9$ are different. In some examples, $X_{13}$, $X_{14}$ and $X_{15}$ are positively charged amino acids. In some examples, $X_{13}$, $X_{14}$ and $X_{15}$ are the same. In some other examples, at least two of $X_{13}$, $X_{14}$ and $X_{15}$ are different from each other.

In general, the positively charged amino acids may include, but are not limited to, lysine (K), arginine (R) or histidine (H). The positively charged amino acids may also include positively charged unnatural amino acids such as ornithine; 2,4-diaminobutanoic acid 2,3-diaminopropanoic acid), 3-(aminoiminomethyl)amino-alanine, 2-amino-4-(aminoiminomethyl)aminobutanoic acid, $N^6$-(aminoiminomethyly) lysine, 2-amino-7-(aminoiminomethyl)amino-heptanoic acid, 2,7-diaminoheptanoic acid, 2,8-diaminooxtanoic acid, 2,9-diaminononanoic acid, 2,10-diaminodecanoic acid, 4-(aminoiminomethyl)phenylalanine or 4-(aminoiminomethyl)aminophenylalanine.

Exemplary peptides represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ include, but are not limited to, the following sequences:

i)
QLGKKKHRRRPSKKKRHW; (SEQ ID NO: 3)

ii)
QLGRRRHRRRPSRRRRHW; (SEQ ID NO: 4)

iii)
QLGKKILAARPSKKKRHW; (SEQ ID NO: 5)

iv)
HRRRPSKKKRHW; (SEQ ID NO: 37)
and v)
QLGAAAHRRRPSKKKRHW. (SEQ ID NO: 38)

In one example, the isolated cytotoxic peptide as described herein excludes the sequence of QLGKK-KHRRRPSKKKRHW (SEQ ID NO: 3).

In some examples, the isolated cytotoxic peptide comprising the amino acid sequence represented by the consensus sequence as described above can include one or more additional amino acids at either end of the amino acid sequence represented by the consensus sequence. For example, the isolated cytotoxic peptide can include at least 1, at least 3, at least 5, at least 7, at least 9, at least 11, at least 13, at least 15, at least 17, at least 19, or 2, 4, 6, 8, 10, 12, 14, 16, 18, 20 additional amino acid residues at the N-terminal and/or the C-terminal of the amino acid sequence represented by the consensus sequence.

In some examples, the functional part of the amino acid sequence represented by the consensus sequence comprises at least the following stretches of amino acid residues $X_8$-$X_9$-$R_{10}$ and $X_{13}X_{14}X_{15}$. Exemplary peptides comprising such functional part include, but are not limited to, the following sequences:

i)
HRRRPSKKKRHW; (SEQ ID NO: 37)
and ii)
QLGAAAHRRRPSKKKRHW. (SEQ ID NO: 38)

In some other examples, the isolated cytotoxic peptide comprising the amino acid sequence represented by the consensus sequence as described above can include more than one amino acid sequence represented by the consensus sequence. In some specific examples, the isolated cytotoxic peptide as described above includes at least 2, at least 3 or at least 4 amino acid sequences represented by the consensus sequence. In some examples, at least 2 or at least 3 of the amino acid sequences represented by the consensus sequence are of the same sequence. In some other examples, all the amino acid sequences represented by the consensus sequence are different. In some examples, the more than one amino acid sequences represented by the consensus sequence are separated by 1 to 3, 4 to 6, 7 to 9, 10 to 12, 11 to 13, 14 to 16, 17 to 19, 20 to 22 or 23 to 25 other amino acid residues. In some other examples, at least 2 or at least 3 of the more than one amino acid sequences represented by the consensus sequence are not separated by any other amino acid residues.

In some examples, the isolated cytotoxic peptide as described herein can exert it cytotoxicity via the apoptosis-independent pathway, the p53-independent pathway or the p-TEFb-independent pathway. Thus, in some examples, the isolated cytotoxic peptide or conjugate thereof is effective against cancer resistant to p53-directed therapy, cancer resistant to the TEFb-directed pathway, or cancer resistant to therapies targeting other apoptosis-dependent pathways.

The term "resistant" or grammatical variants are used herein in the context of being drug-resistant, and refer to the reduction in effectiveness of a drug in curing a disease or condition. Drug resistance can result from, for example, defects in a pathway or defects in element(s) in a pathway targeted by the drug. In one specific example, a patient with a mutated or an otherwise defective p53 protein will show resistance to a drug targeting the p53-dependent pathway.

The isolated cytotoxic peptide as disclosed herein may contain peptide modifications. The term "modification" is used herein to refer to post-translational modification in general, which are modifications that occur on a peptide usually after its translation by ribosome is complete. Post-translational modification generally refers to the addition of a functional group covalently to a protein. These modifications include, but are not limited to, phosphorylation, glycosylation, sulfation, biotinylation, hydroxylation, acetylation, ubiquitination, nitrosylation, methylation, acetylation and lipidation.

In some examples, the isolated cytotoxic peptide as described herein contains at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or 1 to 4, 5 to 8, 9 to 12, 13 to 16, 17 to 20, 21 to 24, 25 to 28, 29 to 32, 33 to 36, 37 to 40, 41 to 44, 45 to 48 or 49 to 52 modified amino acid residues. In some examples, all the modified amino acid residues contain the same type of modification. In some other examples, at least some of the modified amino acid residues contain different types of modifications. In some examples, wherein the isolated cytotoxic peptide comprises more than one amino acid sequence represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36), at least two of the amino acid sequences represented by the consensus sequence contain the same amino acid modifications. In some other examples, wherein the isolated cytotoxic peptide comprises more than one amino acid sequence represented by the consensus sequence, all the amino acid sequences represented by the consensus sequence are modified differently. In some examples, one amino acid residue may contain multiple modifications, such as one, two or three modifications. In some examples, all the modifications on the same amino acid residue are of the same type. In some other examples, at least some of the modifications on the same amino acid residue are of different types. Examples of such modification include, but are not limited to glycosylation, sulfation, phosphorylation, ubiquitination, methylation, lipidation, biotinylation, hydroxylation and acetylation.

The term "glycosylation" as used herein refers to the addition of a glycosyl group, usually to, but not limited to an arginine, an asparagine, a cysteine, a hydroxylysine, a serine, a threonine, a tyrosine, or a tryptophan residue, resulting in a glycoprotein. A glycosyl group refers to a substituent structure obtained by removing the hemiacetal hydroxyl group from the cyclic form of a monosaccharide and, by extension, of a lower oligosaccharide.

The term "sulfation" as used herein refers to the addition of a sulfo group usually to a tyrosine residue. A sulfo group refers to group $SO_3H^-$, derived from sulfuric acid.

The term "phosphorylation" as used herein refers to the addition of a phosphate group. Protein phosphorylation commonly takes place at the serine, threonine, tyrosine, arginine, lysine, or cysteine residues. Phosphorylation may alter the structural conformation of a protein, causing it to become activated, deactivated, or modifying its function.

The term "ubiquitination" as used herein refers to the addition of a ubiquitin. Ubiquitin is a small protein that is found in almost all cellular tissues in humans and other eukaryotic organisms, which helps to regulate the processes of other proteins in the body. The genes in the human genome that produce ubiquitin include, but are not limited to: UBB, UBC, UBA52 and RPS27A. Ubiquitination may affect, for example, the activity and location of a protein, as well the interaction of the ubiquitinated protein with other proteins. In some examples, ubiquitination may lead to the degradation of the protein. In some examples, the protein is degraded via the proteasome.

The term "methylation" as used herein refers to the addition of a methyl group. A methyl group refers to an alkyl derived from methane, containing one carbon atom bonded to three hydrogen atoms, that is —$CH_3$. Protein methylation can commonly take place at the arginine or lysine amino acid residues.

The term "lipidation" as used herein refers to the addition of a lipid group. Examples of lipidation include but are not limited to N-Myristoylation, Palmitoylation, Glycosylphosphatidylinositol (GPI)-anchor addition and Prenylation.

The term "biotinylation" as used herein refers to the addition of a biotin. A biotin refers to 5-[(3aS,4S,6aR)-2-oxohexahydro-1H-thieno[3,4-d]imidazol-4-yl]pentanoic acid, with the following structural formula:

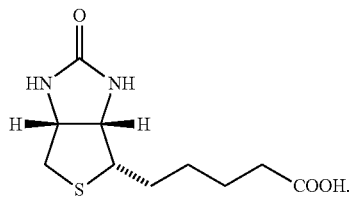 [SMILES: O=C(O)CCCC[C@@H]1SC[C@@H]2NC(=O)N[C@@H]21]

The term "hydroxylation" as used herein refers to the addition of a hydroxyl group (—OH).

The term "acetylation" as used herein refers to the addition of an acetyl group. An acetyl group contains a methyl group single-bonded to a carbonyl, represented by the following formula:

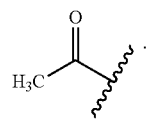

Amino acid changes in the polypeptide or fragment thereof may be effected by techniques well known to persons skilled in the relevant art. For example, amino acid changes may be effected by nucleotide replacement techniques which include the addition, deletion or substitution of nucleotides, under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction.

The cell internalization of the cytotoxic peptide disclosed herein may require facilitators such as cell penetrating or cell targeting peptides or proteins. Thus, in one example, the isolated cytotoxic peptide as described herein is conjugated to at least one internalizing peptide or protein.

The term "conjugate" as used herein refers to the attachment of the isolated cytotoxic peptide to another object, such as other peptide(s) or polypeptide(s), protein(s), antibody(ies), or particle(s). The attachments can be resulted from covalent bonding or weak interactions. The term "conjugation" should be construed accordingly.

In some examples, the isolated cytotoxic peptide as described herein can be conjugated to an antibody.

The term "antibody" is used in the broadest sense to refer to an immunoglobulin molecule, a fragment of an immunoglobulin molecule, or a derivative of either thereof. The antibody can be a monoclonal antibody or a polyclonal antibody. In some examples, the antibody is an antibody for cancer therapy. Examples of an antibody for cancer therapy include, but are not limited to, Ado-trastuzumab emtansine (CAS No. 1018448-65-1), Alemtuzumab (CAS No. 216503-57-0), Bevacizumab (CAS No. 216974-75-3), Blinatumomab (CAS No. 853426-35-4), Brentuximab vedotin (CAS No. 914088-09-8), Cetuximab (CAS No. 205923-56-4), Daratumumab (CAS No. 945721-28-8), Denileukin diftitox (CAS No. 173146-27-5), Gemtuzumab (CAS No. 220578-59-6), Ibritumomab tiuxetan (CAS No. 174722-31-7), Ipilimumab (CAS No. 477202-00-9), Nivolumab (CAS No. 946414-94-4), Ofatumumab (CAS No. 679818-59-8), Panitumumab (CAS No. 339177-26-3), Rituximab (CAS No. 174722-31-7), Tositumomab (CAS No. 192391-48-3)

and Trastuzumab (CAS No. 180288-69-1). Other antibodies for cancer therapy can also be used.

The isolated cytotoxic peptide as described herein can be conjugated to a protein or an antibody by, for example but not limited to, a cross-linker, a bifunctional linker or a trifunctional linker. Linker groups can be, for example but not limited to, small organic compounds or peptides substituted with chemical linkers. In some examples, the chemical linkers can be, but not limited to, any one of the following: succinimidyl 3-(2-pyridyldithio)propionate (SPDP), succinimidyl 4-(N-maleimidomethyl)cyclohexane-1-carboxylate (SMCC), succinimidyl 4-(p-maleimidophenyl)butyrate (SMPB), 4-succinimidyloxycarbonyl-alpha-methyl-α(2-pyridyldithio)toluene (SMPT), EMCS (N-ε-malemido-caproyl-oxysuccinimide ester) and Sulfo-MBS (m-maleimidobenzoyl-N-hydroxysulfosuccinimide ester).

In some examples, a thiol group on the peptide is required for conjugating the isolated cytotoxic peptide as described herein to a linker. Thus, the isolated cytotoxic peptide will have at least one additional cysteine residue at either end of the peptide. Therefore, in some examples, the isolated cytotoxic peptide as described herein further comprises at least one cysteine residue at the N-terminal and/or the C-terminal end.

In general, the isolated cytotoxic peptide as described herein can exert its cytotoxic effect on any cell type, once the isolated cytotoxic peptide is internalized into the cell. Therefore, depending on the type of internalizing peptide or protein being conjugated to, the isolated cytotoxic peptide as described herein can exert its cytotoxic effect on a specific type of cell. In some examples, the internalizing peptide or protein is a cell penetrating peptide or protein. In some other examples, the internalizing peptide or protein is a cell targeting peptide or protein. In some examples, a cell penetrating peptide or protein can also function as a cell targeting peptide or protein. Examples of peptides that can function as both a cell penetrating peptide and a cell targeting peptide include but are not limited to, LTVSPWY peptide (LTV, SEQ ID NO: 8), HLYVSPW peptide (Pep2, SEQ ID NO: 795), CGFYWLRSC peptide (NRP, SEQ ID NO: 796) and CQDGRMGFC peptide (BLA, SEQ ID NO: 797). In some specific examples, the cell targeting peptide or protein is a cancer cell targeting peptide or protein. In some other specific examples, the cell targeting peptide or protein is a lipocyte targeting peptide or protein. In some further examples, the cell targeting peptide or protein is a stem cell targeting peptide or protein. In some examples, such conjugation can result in the internationalization of both the cytotoxic peptide and the internalizing peptide or protein. Examples of a cell-penetrating peptide include, but are not limited to, transactivator of transcription (TAT), penetratin, R6-Pen, transportan, MPG peptide, sweet arrow peptide (SAP), peptide from vascular endothelial-cadherin protein (pVEC), Pep-1 (KETWWETWWTEWSQPKKKRKV) (SEQ ID NO: 6), polylysines, polyarginines, model amphipathic peptide (MAP), FGF (AAVALLPAVLLALLAP) (SEQ ID NO: 798) and R6W3 (RRWWRRWRR)(SEQ ID NO: 7). Examples of a cancer cell-targeting peptide include but are not limited to arginine-glycine-aspartic acid (RGD), asparagine-glycine-arginine (NGR), TCP-1 phage peptide (TCP-1), and the peptides listed in Table 1. Examples of a lipocyte-targeting peptide include but are not limited to, CKGGRAKDC peptide (ATS, SEQ ID NO: 39). Examples of stem cell targeting peptide are listed in Table 2. Examples of conjugated peptides and their effects are discussed in details in Examples 6 to 8.

TABLE 1

Sequences of cancer cell targeting peptides

| SEQ ID NO: | Cancer cell targeting peptide |
|---|---|
| 8 | LTVSPWY |
| 9 | IFLLWQR |
| 10 | CGNSNPKSC |
| 11 | SVSVGMKPSPRP |
| 64 | CSNIDARAC |
| 65 | CDPSRGKNC |
| 66 | CPSDLKDAC |
| 67 | CRTTRGTKC |
| 68 | CRMTRNKPC |
| 69 | CRVSRQNKC |
| 70 | CAKIDPELC |
| 71 | CGGERGKSC |
| 72 | YSINDWH |
| 73 | YSFNSWM |
| 74 | PNPNNST |
| 75 | YPTPYDI |
| 76 | LPAMPNS |
| 77 | CNRRTKAGC |
| 78 | SRHDLNS |
| 79 | STVATSQ |
| 80 | QRLGNQWAVGHLM |
| 81 | RGDF |
| 82 | KGVSLSYR |
| 83 | QFPPKLTNNSML |
| 84 | SYDILKPNPQRL |
| 85 | SHGKPPSFSPYT |
| 86 | LLADTTHHRPWT |
| 87 | CTPSPPFSHC |
| 88 | CPNGRC |
| 89 | CLSYYPSYC |
| 90 | RTRYED |
| 91 | GMMYRS |
| 92 | RWRTNF |
| 93 | RLQLKL |
| 94 | RIPLEM |
| 95 | QFDEPR |
| 96 | TSAVRT |
| 97 | GLWQGP |

TABLE 1-continued

Sequences of cancer cell targeting peptides

| SEQ ID NO: | Cancer cell targeting peptide |
|---|---|
| 98 | QCTGRF |
| 99 | LPGMMG |
| 100 | DVGTTE |
| 101 | TDLGAM |
| 102 | DSNAES |
| 103 | ITDMAA |
| 104 | WRPCES |
| 105 | WRNTIA |
| 106 | IDKQLE |
| 107 | FMEIET |
| 108 | HEVVAG |
| 109 | GGHTRQ |
| 110 | INGKVT |
| 111 | VPWXEPAYQRFL |
| 112 | GRDS |
| 113 | RGEPAYQRFL |
| 114 | RGDPAYQRFL |
| 115 | WXEPAYQGRFL |
| 116 | WXEPAYNGRFL |
| 117 | RGEPAYQGRFL |
| 118 | RGDPAYQGRFL |
| 119 | RGEPAYNGRFL |
| 120 | RGDPAYNGRFL |
| 121 | WXEPAYQRFL |
| 122 | AXEPAYQRFL |
| 123 | WAEPAYQRFL |
| 124 | WXAPAYQRFL |
| 125 | WXEAAYQRFL |
| 126 | WXEPAAQRFL |
| 127 | WXEPAYARFL |
| 128 | WXEPAYQAFL |
| 129 | WXEPAYQAAL |
| 130 | WXEPAYQAFA |
| 131 | EXEPAYQRFL |
| 132 | LXEPAYQRFL |
| 133 | KXEPAYQRFL |
| 134 | QXEPAYQRFL |
| 135 | YXEPAYQRFL |

TABLE 1-continued

Sequences of cancer cell targeting peptides

| SEQ ID NO: | Cancer cell targeting peptide |
|---|---|
| 136 | FXEPAYQRFL |
| 137 | F*XEPAYQRFL |
| 138 | WXEPAYREL |
| 139 | WXEPAYRLL |
| 140 | WXEPAYRKL |
| 141 | WXEPAYQRQ |
| 142 | WXEPAYQRYL |
| 143 | WXEPAYQRF*L |
| 144 | WXEPAYQRFL |
| 145 | WXEPAYQRRE |
| 146 | WXEPAYQRFK |
| 147 | WXEPAYQRFQ |
| 148 | WXEPAYQRFT |
| 149 | WXEPAYQRFF |
| 150 | XEPAYQRFL |
| 151 | XEPAYQREL |
| 152 | XEPAYQRLL |
| 153 | XEPAYQRKL |
| 154 | XEPAYQRQL |
| 155 | XEPAYQRYL |
| 156 | XEPAYQRF*L |
| 157 | XEPAYQRFL |
| 158 | XEPAYQRFE |
| 159 | XEPAYQRFK |
| 160 | XEPAYQRFQ |
| 161 | XEPAYQRFT |
| 162 | XEPAYQRFF |
| 163 | KSLSRHDHIHHH |
| 164 | GGCLQILPTLSECFGR |
| 165 | GLKVCGRYPGICDGIR |
| 166 | GKYTWYGYSLRANWMR |
| 167 | VPCQKRPGWVCLW |
| 168 | KWCVIWSKEGCLF |
| 169 | SSWCMRGQYNKICMW |
| 170 | VECYLIRDNLCIY |
| 171 | WWCLGERVVRCAH |
| 172 | FYCVIERLGVCLY |
| 173 | RVCFLWQDGRCVF |

TABLE 1-continued

Sequences of cancer cell targeting peptides

| SEQ ID NO: | Cancer cell targeting peptide |
|---|---|
| 174 | NRLKCRAQATHSAAPCIRGY |
| 175 | RQNSCTYSDARRWALCWSGE |
| 176 | QLNSCIFISGDRAIRGCMDWV |
| 177 | KYGLCRDETVFPSHSCTFTG |
| 178 | GSPQCPGGFNCPRCDCGAGY |
| 179 | GTGSCGYGKLHTGYWCSYFP |
| 180 | NSSSCDTSVVRSTWACILQP |
| 181 | VRAVCTTLKSRGHEECWSLQ |
| 182 | VYAQCGVNVRTGRGGCSRLM |
| 183 | VHMNCSWMRVSEGHPCESAD |
| 184 | GRQGCYEHLWRLIAWCAIFL |
| 185 | LRMTCAFGVAQRSADCALSS |
| 186 | SIVNCSAALTDLPTRCGGNI |
| 187 | CGTRCVRCQNGPEASCEQPL |
| 188 | TPLFCGNHGRQPSPLCMKWD |
| 189 | FTTVCRQPRGHEAIVCGSGK |
| 190 | APSFCGTAMLGASRYCYSGP |
| 191 | GARECESGGPGMRKLCTQIN |
| 192 | NNRACFRTSKGNPAECPYLG |
| 193 | GSLACQNIVVCVKKQCNALC |
| 194 | KRASCQNPLFSNFFVCGLSE |
| 195 | LPNFCMDTSGRAGPLCMGSE |
| 196 | RHTVCRVSLSSVQGSCSHEY |
| 197 | CGLIIQKNEC |
| 198 | CNAGESSKNC |
| 199 | GRRTRSRRLRRS |
| 200 | SMSIASPQIPWS |
| 201 | TPRNLRTSNTHR |
| 202 | GRRIAGPYIALE |
| 203 | SMPINSPYIPWS |
| 204 | GRRPMKLNKTP |
| 205 | GRRINTRLILPRN |
| 206 | GRRTRSSRLRNS |
| 207 | CLSDGKRKC |
| 208 | CLDGGRPKC |
| 209 | CREAGRKAC |
| 210 | CAGRRSAYC |
| 211 | CNRRTKAGC |
| 212 | CPIEDRPMC |
| 213 | CGRRAGGSC |
| 214 | CGNSNPKSC |
| 215 | CPHNLTKLC |
| 216 | GPLPLR |
| 217 | CDCRGDCFC |
| 218 | GHGKHKNK |
| 219 | HKHGHGKHKNKGK |
| 220 | KHGHGHGK |
| 221 | KGHHGKHG |
| 222 | HKNKGKKN |
| 223 | CRGRRST |
| 224 | CRSRKG |
| 225 | CKAAKNK |
| 226 | CKGAKAR |
| 227 | FRVGVADV |
| 228 | CEYQLDVE |
| 229 | CSRPRRSEC |
| 230 | CGKRK |
| 231 | CDTRL |
| 232 | CGTKRKC |
| 233 | CDTAVVEGL |
| 234 | CRSRKG |
| 235 | CEYQLDVE |
| 236 | CPIEDRPMC |
| 237 | PIEDRPM |
| 238 | PIDERPM |
| 239 | ALRDRPM |
| 240 | PMMRQRPM |
| 241 | PLASRPM |
| 242 | PEKFRPM |
| 243 | VPEQRPM |
| 244 | DLPMHPM |
| 245 | QFQSQPM |
| 246 | QPPMEYS |
| 247 | NGRSL |
| 248 | MTQMIS |
| 249 | TALSPQ |

TABLE 1-continued

Sequences of cancer cell targeting peptides

| SEQ ID NO: | Cancer cell targeting peptide |
|---|---|
| 250 | WNLPWYYSVSPT |
| 251 | LTVLPW |
| 252 | LTVEPWL |
| 253 | LTVSPLWD |
| 254 | LTVTPWL |
| 255 | LTVQPWP |
| 256 | LTVSPWT |
| 257 | VLTVQPW |
| 258 | LTVSLWT |
| 259 | PGVIPWN |
| 260 | LTYQTWP |
| 261 | ELYVSRL |
| 262 | NLYYASW |
| 263 | TLTVLPW |
| 264 | NLYVASW |
| 265 | SMSIARL |
| 266 | VSFLEYR |
| 267 | CPGPEGAGC |
| 268 | RGDfK |
| 269 | PRPGAPLAGSWPGTS |
| 270 | ADGAPRPGAPLA |
| 271 | DRWRPALPVVLFPLH |
| 272 | ASSSYPLIHWRPWAR |
| 273 | DRWRPALP |
| 274 | IHWRPWAR |
| 275 | AAEWLDAFFVRHVDR |
| 276 | GDVWLFLTSTSHFAR |
| 277 | GCSVSSVGALCTHV |
| 278 | APCCSHLDASPFQRP |
| 279 | AQSNFVTWGYNVAV |
| 280 | RASDVGSDVVPRYPF |
| 281 | MARSGL |
| 282 | MARAKE |
| 283 | MSRTMS |
| 284 | MTKSAG |
| 285 | MTKCRG |
| 286 | MTRNLQ |
| 287 | MTRQIG |
| 288 | MSRPHK |
| 289 | MAKHAM |
| 290 | CWWRLEGC |
| 291 | CLQLFSTC |
| 292 | CAKGYRSC |
| 293 | CTGSWLGC |
| 294 | AEGEFMYWGDSHWLQYWYEGDPAK |
| 295 | AEGEFWGDSHWLQYWYEGDPAK |
| 296 | AEGEFIHNRYNRFFYWYGDPAK |
| 297 | AEGEFPRWGDSHWLQYWYEGDPAK |
| 298 | AEGEFLMWGGSHWLEYWYEGDPAK |
| 299 | AEGEFGHWCDQHWLQYWYEGDPAK |
| 300 | AEGEFGWWGDSHWLQYEGDPAK |
| 301 | CRGDCF |
| 302 | CDCRGDCFC |
| 303 | CNGRCVSGCAGRC |
| 304 | CGSLVRC |
| 305 | CRGDCGGKWCFRVCYRGICYRRCR |
| 306 | MCPKHPLGC |
| 307 | LCPKHPLGC |
| 308 | HLQIQPWYPQIS |
| 309 | VPWMEPAYQRFL |
| 310 | LSSVNSFPVVTP |
| 311 | QPWLEQAYYSTF |
| 312 | SALLPWPVLVNY |
| 313 | ITTPWDEMRSFL |
| 314 | HSFLHPWDLFDY |
| 315 | VPWMEPAYQRFL |
| 316 | MLPKPSSFPVPG |
| 317 | HSFLHPWDLFDY |
| 318 | CNGRCVSGCAGRC |
| 319 | CVLNGRMEC |
| 320 | FDDARL |
| 321 | FSDARL |
| 322 | FSDMRL |
| 323 | FVDVRL |
| 324 | FTDIRL |
| 325 | FNDYRL |

TABLE 1-continued

Sequences of cancer cell targeting peptides

| SEQ ID NO: | Cancer cell targeting peptide |
|---|---|
| 326 | FSDTRL |
| 327 | DPAFIFYHSTLFFNS |
| 328 | GGHDGDPVLTGTLFY |
| 329 | AVDPRMFYLLLRGGA |
| 330 | PIHYIF |
| 331 | YIHYIF |
| 332 | RIHYIF |
| 333 | WREWFL |
| 334 | WWAMKP |
| 335 | LILSSGELLRHPRG |
| 336 | TAASGVRSMH |
| 337 | LTLRWVGLMS |
| 338 | GGGTRAGMKY |
| 339 | WGKIEDPLRA |
| 340 | AGQTLTASGD |
| 341 | DLLAVSWLRA |
| 342 | SAERGVVAMS |
| 343 | AIHSELMWVS |
| 344 | FWTERAGWAY |
| 345 | MVWSKGPLFL |
| 346 | AGTRMSWEVL |
| 347 | VSRSSRWGSI |
| 348 | DAHVLVPRTP |
| 349 | AQGIVLQLAL |
| 350 | LSPLLSPATA |
| 351 | CDCRGDCFC |
| 352 | CNGRCVSGCAGRC |
| 353 | NGRAHA |
| 354 | CVLNGRMEC |
| 355 | HGRFILPWWYAFSPS |
| 356 | RFRGLISLSQVYLSP |
| 357 | ARVSFWRYSSFAPTY |
| 358 | GSWYAWSPLVPSAQI |
| 359 | KKEKDIMKKTI |
| 360 | GRGDSPK |
| 361 | SNPFSKPYGLTV |
| 362 | YPHYSLPGSSTL |
| 363 | KDEPQRRSARLSAKPAPPKPEPKPKKAPAKK |
| 364 | TLTYTWS |
| 365 | CREKA |
| 366 | CGQKRTRGC |
| 367 | RPARPAR |
| 368 | CRGDGWC |
| 369 | RGDGWK |
| 370 | TSPLNIHNGQKL |
| 371 | CRGDKGPDC |
| 372 | CRGDRGPDC |
| 373 | CRGDKTTNC |
| 374 | CRGDHAGDC |
| 375 | CRGDHGVEC |
| 376 | CGRGDNLPC |
| 377 | CGRGDNLAC |
| 378 | CEKRGDNLC |
| 379 | CEKRGDSVC |
| 380 | CSGRGDSLC |
| 381 | CGKRGDSIC |
| 382 | CTGRGDALC |
| 383 | CRGDSAC |
| 384 | CRGDKGENC |
| 385 | CGRGDSPDC |
| 386 | CRGDKGPEC |
| 387 | CRGDKHADC |
| 388 | CRGDHAANC |
| 389 | CRGDAGINC |
| 390 | CGRGDMPSC |
| 391 | CEKRGDSLC |
| 392 | KDEPQRRSARLSAKPAPPKPEPKPKKAPAKK |
| 393 | CREKA |
| 394 | TDSILRSYDWTY |
| 395 | DMPKQLLAPWYY |
| 396 | DMPKQLLAPWYY |
| 397 | SYPLSFLGPLIS |
| 398 | TQQPLEGHQLPY |
| 399 | TGVSWSVAQPSF |

TABLE 1-continued

Sequences of cancer cell targeting peptides

| SEQ ID NO: | Cancer cell targeting peptide |
|---|---|
| 400 | SVSVGMKPSPRP |
| 401 | SQWNSPPSSAAF |
| 402 | CGNSNPKSC |
| 403 | SFSIIHTPILPL |
| 404 | GNGRAHA |
| 405 | AHLPIVRASLPS |
| 406 | TPMNHHSQHAER |
| 407 | GNIIPDRPMHPT |
| 408 | FPSSLIIPPLPN |
| 409 | EDIKPKTSLAFR |
| 410 | YEDIKPKTSLAFR |
| 411 | TQPADLQTHNHN |
| 412 | FDHSSKWTRTSP |
| 413 | YSHNTITNLYFS |
| 414 | WPRYAESTLQLR |
| 415 | KGVSLSYRKKGVSLSYR |
| 416 | SVSVGMKPSPRP |
| 417 | WPLHTSVYPPSP |
| 418 | NTLPPFSPPSPP |
| 419 | SFPDSNIAPSSP |
| 420 | QHAPSNSKSVLT |
| 421 | WPTYLNPSSLKA |
| 422 | GPSGNLHIRPAS |
| 423 | SPLLSTRAVQLS |
| 424 | SPMFTMIQGDAQ |
| 425 | VNSHQALWSPAQ |
| 426 | STLPPPLRFANV |
| 427 | SFNQPYLYKTAF |
| 428 | YHTRIALPDNLP |
| 429 | AQSTAFQKPLLM |
| 430 | KCCYSL |
| 431 | RLLDTNRPLLPY |
| 432 | CSDSWHYWC |
| 433 | FQHPSFI |
| 434 | SMSIASPYIALE |
| 435 | SMSIASPY1PWS |
| 436 | SPGPMKLLKTPL |
| 437 | TLNINRLILPRT |
| 438 | SMSIGSPYITFG |
| 439 | VPNTNSLPAAVN |
| 440 | LIAKTALPQTNK |
| 441 | LIAKTALPQTN |
| 442 | CPHSKPCLC |
| 443 | GGCRGDMFGC |
| 444 | FRPNRAQDYNTN |
| 445 | QEFSPYMGLEFKKH |
| 446 | QEFSPNLWGLEFQKN |
| 447 | QEYSPNLWGHEFRSH |
| 448 | HTFEPGV |
| 449 | PSTNHAL |
| 450 | PSTLTSS |
| 451 | APSQTYH |
| 452 | KAMSWYA |
| 453 | SRESPHP |
| 454 | QSRLSLG |
| 455 | LDHFAPM |
| 456 | LDKKTTS |
| 457 | NMSPQLD |
| 458 | SQRQTLD |
| 459 | STKLLHE |
| 460 | TSPTNRS |
| 461 | PHSPTSL |
| 462 | HGKYFVS |
| 463 | PQRHVNY |
| 464 | MMSQLAH |
| 465 | PMAHLEF |
| 466 | ELIKESR |
| 467 | QPENLPT |
| 468 | NTHMTAF |
| 469 | PFKLSKH |
| 470 | ASSLHTI |
| 471 | HPLRLPA |
| 472 | HQSVNKE |
| 473 | LQNPTPE |
| 474 | PTEAQLQ |
| 475 | LFAQLGP |

TABLE 1-continued

Sequences of cancer cell targeting peptides

| SEQ ID NO: | Cancer cell targeting peptide |
|---|---|
| 476 | NQPTRAL |
| 477 | TPRTQKA |
| 478 | IHFPSAS |
| 479 | PLRIAQH |
| 480 | CRLTGGKGVGC |
| 481 | CRRTNWQGAGC |
| 482 | CQLTGTHGAGC |
| 483 | CADPNSVRAMC |
| 484 | CADPNSVRAHC |
| 485 | CAAHYRVGPWC |
| 486 | PQNSKIPGPTFLDPH |
| 487 | SMEPALPDWWWKMFK |
| 488 | DKPTAFVSVYLKTAL |
| 489 | APRPGPWLWSNADSV |
| 490 | GVTDSSTSNLDMPHW |
| 491 | PKMTLQRSNIRPSMP |
| 492 | LYPLHTYTPLSLPLF |
| 493 | LTGTCLQYQSRCGNTR |
| 494 | AYTKCSRQWRTCMTTH |
| 495 | ANTPCGPYTHDCPVKR |
| 496 | NISRCTHPFMACGKQS |
| 497 | PRNICSRRDPTCWTTY |
| 498 | GCNGRC |
| 499 | QHWSYKCIRP |
| 500 | CVSNPRWKC |
| 501 | CHVLWSTRC |
| 502 | SWLAYPGAVSYR |
| 503 | YSAYPDSVPMMS |
| 504 | SRESPHP |
| 505 | VPWMEPAYQRFL |
| 506 | CDSDSDITWDQLWDLMK |
| 507 | ATLDGVS |
| 508 | RRHSVSG |
| 509 | SGWFAGS |
| 510 | GSVSHRR |
| 511 | GSVLPVL |
| 512 | RSGRVSN |
| 513 | NSVRGSR |
| 514 | NVVRQ |
| 515 | CDCRGDCFC |
| 516 | CSDSWHYWC |
| 517 | CSDWQHPWC |
| 518 | CSDYNHHWC |
| 519 | CSDGQHYWC |
| 520 | CYDSWHYWC |
| 521 | CFDGNHIWC |
| 522 | CTDFPRSFC |
| 523 | CTQDRQHPC |
| 524 | CLSRYLDQC |
| 525 | CPRECESIC |
| 526 | CTTHWGFTLC |
| 527 | CRRHWGFEFC |
| 528 | CVPELGHEC |
| 529 | HTMYYHHYQHHL |
| 530 | CGNKRTRGC |
| 531 | CGRECPRLCQSSC |
| 532 | CGEACGGQCALPC |
| 533 | IWSGYGVYW |
| 534 | PSCAYMCIT |
| 535 | WESLYFPRE |
| 536 | SKVLYYNWE |
| 537 | CGLMCQGACFDVC |
| 538 | CERACRNLCREGC |
| 539 | CPRGCLAVCVSQC |
| 540 | CKVCNGRCCG |
| 541 | CEMCNGRCMG |
| 542 | CPLCNGRCAL |
| 543 | CPTCNGRCVR |
| 544 | CGVCNGRCGL |
| 545 | CEQCNGRCGQ |
| 546 | CRNCNGRCEG |
| 547 | CVLCNGRCWS |
| 548 | CVTCNGRCRV |
| 549 | CTECNGRCQ |
| 550 | CRTCNGRCLE |
| 551 | CETCNGRCVG |

TABLE 1-continued

Sequences of cancer cell targeting peptides

| SEQ ID NO: | Cancer cell targeting peptide |
|---|---|
| 552 | CAVCNGRCGF |
| 553 | CSCCNGRCGD |
| 554 | CWGCNGRCRM |
| 555 | CPLCNGRCAR |
| 556 | CKSCNGRCLA |
| 557 | CVPCNGRCHE |
| 558 | CQSCNGRCVR |
| 559 | CRTCNGRCQV |
| 560 | CVQCNGRCAL |
| 561 | CRCCNGRCSP |
| 562 | CASNNGRVVL |
| 563 | CGRCNGRCLL |
| 564 | CWLCNGRCGR |
| 565 | CSKCNGRCGH |
| 566 | CVWCNGRCGL |
| 567 | CIRCNGRCSV |
| 568 | CGECNGRCVE |
| 569 | CEGVNGRRLR |
| 570 | CLSCNGRCPS |
| 571 | CEVCNGRCAL |
| 572 | GRSQMQI |
| 573 | HHTRFVS |
| 574 | SKGLRHR |
| 575 | VASVSVA |
| 576 | WRVLAAF |
| 577 | KMGPKVW |
| 578 | IFSGSRE |
| 579 | SPGSWTW |
| 580 | NPRWFWD |
| 581 | GRWYKWA |
| 582 | IKARASP |
| 583 | SGWCYRC |
| 584 | ALVGLMR |
| 585 | LWAEMTG |
| 586 | CWSGVDC |
| 587 | DTLRLRI |
| 588 | SKSSGVS |
| 589 | IVADYQR |

TABLE 1-continued

Sequences of cancer cell targeting peptides

| SEQ ID NO: | Cancer cell targeting peptide |
|---|---|
| 590 | VWRTGHL |
| 591 | VVDRFPD |
| 592 | LSMFTRP |
| 593 | GLPVKWS |
| 594 | IMYPGWL |
| 595 | CVMVRDGDC |
| 596 | CVR1RPC |
| 597 | CQLAAVC |
| 598 | CGVGSSC |
| 599 | CVSGPRC |
| 600 | CGLSDSC |
| 601 | CGEGHPC |
| 602 | CYTADPC |
| 603 | CELSLISKC |
| 604 | CPEHRSLVC |
| 605 | CLVVHEAAC |
| 606 | CYVELHC |
| 607 | CWRKFYC |
| 608 | CFWPNRC |
| 609 | CYSYFLAC |
| 610 | CPRGSRC |
| 611 | CRLGIAC |
| 612 | CDDSWKC |
| 613 | CAQLLQVSC |
| 614 | CYPADPC |
| 615 | CKALSQAC |
| 616 | CTDYVRC |
| 617 | CGETMRC |
| 618 | CLSGSLSC |
| 619 | WGTGLC |
| 620 | GICKDDWCQ |
| 621 | TSCDPSLCE |
| 622 | KGCGTRQCW |
| 623 | YRCREVLCQ |
| 624 | CWGTGLC |
| 625 | WSCADRTCM |
| 626 | AGCRLKSCA |
| 627 | SRCKTGLCQ |

TABLE 1-continued

Sequences of cancer cell targeting peptides

| SEQ ID NO: | Cancer cell targeting peptide |
|---|---|
| 628 | PICEVSRCW |
| 629 | WTCRASWCS |
| 630 | GRCLLMQCR |
| 631 | TECDMSRCM |
| 632 | ARCRVDPCV |
| 633 | CIEGVLGGC |
| 634 | CSVANSC |
| 635 | CSSTMRC |
| 636 | SIDSTTF |
| 637 | GPSRVGG |
| 638 | WWSGLEA |
| 639 | LGTDVRQ |
| 640 | LVGVRLL |
| 641 | GRPGDJW |
| 642 | TVWNPVG |
| 643 | GLLLVVP |
| 644 | FAATSAE |
| 645 | WCCRQFN |
| 646 | VGFGKAL |
| 647 | DSSLRLP |
| 648 | KLWCAMS |
| 649 | SLVSFLG |
| 650 | GSFAFLV |
| 651 | IASVRWA |
| 652 | TWGHLRA |
| 653 | QYREGLV |
| 654 | QSADRSV |
| 655 | YMFWTSR |
| 656 | LVRRWYL |
| 657 | TARGSSR |
| 658 | TTREKNL |
| 659 | PKWLLFS |
| 660 | LRTNVVH |
| 661 | AVMGLAA |
| 662 | VRNSLRN |
| 663 | TDCTPSRCT |
| 664 | SWCQFEKCL |
| 665 | VPCRFKQCW |
| 666 | CTAMRNTDC |
| 667 | CRESLKNC |
| 668 | CMEMGVKC |
| 669 | VTCRSLMCQ |
| 670 | CNNVGSYC |
| 671 | CGTRVDHC |
| 672 | CISLDRSC |
| 673 | CAMVSMED |
| 674 | CYLGVSNC |
| 675 | CYLVNVDC |
| 676 | CIRSAVSC |
| 677 | LVCLPPSCE |
| 678 | RHCFSQWCS |
| 679 | FYCPGVGCR |
| 680 | ISCAVDAC |
| 681 | EACEMAGCL |
| 682 | PRCESQLCP |
| 683 | RSCIKHQCP |
| 684 | QWCSRRWCT |
| 685 | MFCRMRSCD |
| 686 | GICKDLWCQ |
| 687 | NACESAICG |
| 688 | APCGLLACI |
| 689 | NRCRGVSCT |
| 690 | FPCEGKKCL |
| 691 | ADCRQKPCL |
| 692 | FGCVMASCR |
| 693 | AGCINGLCG |
| 694 | RSCAEPWCY |
| 695 | DTCRALRCN |
| 696 | KGCGTRQCW |
| 697 | GRCVDGGCT |
| 698 | YRCIARECE |
| 699 | KRCSSSLCA |
| 700 | ICLLAHCA |
| 701 | QACPMLLCM |
| 702 | LDCLSELCS |
| 703 | AGCRVESC |

TABLE 1-continued

Sequences of cancer cell targeting peptides

| SEQ ID NO: | Cancer cell targeting peptide |
|---|---|
| 704 | HTCLVALCA |
| 705 | IYCPGQECE |
| 706 | RLCSLYGCV |
| 707 | RKCEVPGCQ |
| 708 | EDCTSRFCS |
| 709 | LECVVDSCR |
| 710 | EICVDGLCV |
| 711 | RWCREKSCW |
| 712 | FRCLERVCT |
| 713 | RPCGDQACE |
| 714 | CNKTDGDEGVTC |
| 715 | PQRRSARLSA |
| 716 | IELLQAR |
| 717 | ISLLQAR |
| 718 | IDLMQAR |
| 719 | IILLQGR |
| 720 | ISLLGAR |
| 721 | FSLLDAR |
| 722 | CTPSPFSHC |
| 723 | AGTRMSWEV |
| 724 | CSNRDARRC |
| 725 | WQPDTAHHWATL |
| 726 | HNAYWHWPPSMT |
| 727 | GHLIPLRQPSH |
| 728 | YTSPHHSTTGHL |
| 729 | WTHHHSYPRPL |
| 730 | NSFPLMLMHHHP |
| 731 | KHMHWHPPALN |
| 732 | SLDSMSPQWHAD |
| 733 | SEFIHHWTPPPS |
| 734 | NGFSHHAPLMRY |
| 735 | HHEWTHHWPPP |
| 736 | AWPENPSRRPF |
| 737 | AGFQHHPSFYRF |
| 738 | QRSPMMSRIRLP |
| 739 | YRHWPIDYPPP |
| 740 | MIHTNHWWAQD |
| 741 | CALIIQKNEC |
| 742 | CGLILQKNEC |
| 743 | CGLIIQRNEC |
| 744 | CGLIINKNEC |
| 745 | CNAAESSKNC |
| 746 | CNAGESSRNC |
| 747 | CNAGESTKNC |
| 748 | CNAGDSSKNC |
| 749 | CLSDGK |
| 750 | CLSDGKPVS |
| 751 | CSMSAKKKC |
| 752 | CKTRVSCGV |
| 753 | CASLSCR |
| 754 | CSGGKVLDC |
| 755 | CASLSCR |
| 756 | CSGGKVLDC |
| 757 | CSMSAKKKC |
| 758 | CKTRVSCGV |
| 759 | CASLSCR |
| 760 | WIFPWIQL |
| 761 | WDLAWMFRLPVG |
| 762 | CRGSGAGRC |
| 763 | CKGGRAKDC |
| 764 | CGSPGWVRC |
| 765 | VGVGEWSV |
| 766 | SRPRR |
| 767 | CXSRPRRZC |
| 768 | CSRPRRSVC |
| 769 | CSRPRRSWC |
| 770 | CGLSGLGVA |
| 771 | CPIRPMEDC |
| 772 | CPIDERPMC |
| 773 | CALRDRPMC |
| 774 | CPEKFRPMC |
| 775 | CSPQSQPMC |
| 776 | CGLIIQKNEC |
| 777 | CRGDK |
| 778 | KDEPQRRSARLSAKPAPPKPEPKPKKAPAKK |

TABLE 1-continued

Sequences of cancer cell targeting peptides

| SEQ ID NO: | Cancer cell targeting peptide |
|---|---|
| 779 | CGQKRTRGC |
| 780 | NVVRQ |
| 781 | PHSCNK |
| 782 | HPLSKHPYWSQP |
| 783 | IFLLWQR |
| 784 | APRPG |
| 785 | CRGDRCPDC |
| 786 | CVNHPAFAC |
| 787 | KDEPQRRSARLSAKPAPPKPEPKPKKAPAKK |
| 788 | CGKRK |
| 789 | KDEPQRRSARLSAKPAPPKPEPKPKKAPAKKC |

TABLE 2

Sequences of stein cell targeting peptides

| SEQ ID NO: | Stem cell targeting peptide sequence |
|---|---|
| 41 | AVGPYSGLKVFR |
| 42 | SPLSKGSTHLST |
| 43 | TNKPVQPRQTLP |
| 44 | AMHPSPASAKMN |
| 45 | AGAPYRNTNAGT |
| 46 | TPTERFNTHHVE |
| 47 | QAGDEKEWLGPK |
| 48 | GSNQSVRYLQQT |
| 49 | NVDYAFGKREQS |
| 50 | DPLLHSQADVQS |
| 51 | LPHSSWNPKLAL |
| 52 | HQVHAKPLDLMP |
| 53 | QYTFSVNPLMRA |
| 54 | VPHFSTPTSVFQ |
| 55 | NYAIAVVNVLSH |
| 56 | NTKVPDPTARLL |
| 57 | HGAAWGTRTGHV |
| 58 | VPATETAQAGHA |
| 59 | VEYHFNHTMTAY |
| 60 | VGGEAWSSPTDL |
| 61 | HSDQVALKMTRS |

TABLE 2-continued

Sequences of stein cell targeting peptides

| SEQ ID NO: | Stem cell targeting peptide sequence |
|---|---|
| 62 | QPHSVSVSDTWH |
| 63 | SNNDNLAHRVRL |

The isolated cytotoxic peptide or conjugate thereof as described herein can exert its cytotoxicity selectively. Thus, in some examples, the isolated cytotoxic peptide or conjugate thereof has low toxicity towards cells and tissue that are not the target of the conjugated cell penetrating peptide or cell targeting peptide.

In some examples, the isolated cytotoxic peptide or conjugate thereof exerts its cytotoxic effects only upon internalization into a target cell.

The stability of the isolated cytotoxic peptide as disclosed herein can be enhanced by conjugating to a particle, in particular a small particle. Examples of a particle include but are not limited to, nanoparticle or microparticle. In some examples, the nanoparticle or microparticle is made from materials including but not limited to, metal, silica, carbon, polymeric materials, and mixtures thereof. Examples of metal include, but are not limited to, gold and silver. Examples of polymeric materials include, but are not limited to, bio-degradable polymers such as a poly(lactide-co-glycolide), poly(lactic acid), poly(alkylene glycol), polybutylcyanoacrylate, poly(methylmethacrylate-co-methacrylic acid), poly-allylamine, polyanhydride and polyhydroxybutyric acid.

In the present disclosure, there is provided an isolated nucleic acid molecule comprising the nucleotide sequence encoding a peptide as described herein.

Since the degeneracy of the genetic code permits substitutions of certain codons by other codons which specify the same amino acid and hence give rise to the same protein, the disclosure is not limited to a specific nucleic acid molecule but includes all nucleic acid molecules comprising a nucleotide sequence coding for the peptide as described herein.

A nucleic acid molecule, such as DNA (including cDNA and genomic DNA), RNA (such as mRNA), is regarded to be 'capable of expressing a nucleic acid molecule or a coding nucleotide sequence' or capable 'to allow expression of a nucleotide sequence' if it contains regulatory nucleotide sequences which contain transcriptional and translational information and such sequences are "operably linked" to nucleotide sequences which encode the peptide. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced peptide to a specific compartment of a host cell, which is used for producing a peptide described above. The isolated nucleic acid molecule as described herein can be obtained by cloning or produced synthetically. Examples of the isolated nucleic acid molecules are listed in Table 3.

TABLE 3

Examples of isolated nucleic acid molecules encoding the polypeptides as described herein

| SEQ ID NO: | Sequences (5' to 3') |
|---|---|
| 790 | cagctgggcaaaaaaaaacatcgccgccgcccgagcaaaaaaaacgccattgg |
| 791 | cagctgggcgcggcggcgcatcgccgccgcccgagcaaaaaaaacgccattgg |
| 792 | cagctgggccgccgccgccatcgccgccgcccgagccgccgccgccgccattgg |
| 793 | cagctgggcaaaaaaattctggcggcgcgcccgagcaaaaaaaacgccattgg |
| 794 | catcgccgccgcccgagcaaaaaaaaacgccattgg |

The isolated nucleic acid molecule comprising the nucleotide sequence encoding the peptide as disclosed herein can be comprised in a vector, for example an expression vector. Thus, in the present disclosure, there is provided a vector comprising an isolated nucleic acid molecule as described herein. Representative vectors include plasmids, cosmids, and viral vectors. Vectors can also comprise nucleic acids including expression control elements, such as transcription/translation control signals, origins of replication, polyadenylation signals, internal ribosome entry sites, promoters and enhancers, wherein the control elements are operatively associated with a nucleic acid encoding a gene product. Selection of these and other common vector elements are conventional and many such sequences can be derived from commercially available vectors. A vector can be introduced into targeting cells using any suitable method known in the art for introducing DNA into cells, including but not limited to microinjection, electroporation, calcium phosphate precipitation, liposome-mediated delivery, viral infection, protoplast fusion, and particle-mediated uptake.

The vector comprising the isolated nucleic acid molecule can be transformed into host cells capable of expressing the genes. The transformation can be carried out in accordance with standard techniques. Thus, the disclosure is also directed to a (recombinant) host cell containing a vector as described herein. In this context, the transformed host cells can be cultured under conditions suitable for expression of the nucleotide sequence encoding the peptide as described above. Host cells can be established, adapted and completely cultivated under serum free conditions, and optionally in media which are free of any protein/peptide of animal origin. Commercially available media such as RPMI-1640 (Sigma), Dulbecco's Modified Eagle's Medium (DMEM; Sigma), Minimal Essential Medium (MEM; Sigma), CHO-S-SFMII (Invitrogen), serum free-CHO Medium (Sigma), and protein-free CHO Medium (Sigma) are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that are known to those skilled in the art.

The isolated cytotoxic peptide or conjugate thereof, the isolated nucleic acid molecule or the vector as described herein can be formulated into compositions, for example pharmaceutical compositions, suitable for administration. Where applicable, the peptide or conjugate thereof, the nucleic acid molecule or the vector can be administered with a pharmaceutically acceptable carrier. A "carrier" can include any pharmaceutically acceptable carrier as long as the carrier is compatible with other ingredients of the formulation and not injurious to the patient. Accordingly, pharmaceutical compositions for use may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Thus, in one example, the present disclosure provides a pharmaceutical composition comprising, but not limited to, an isolated cytotoxic peptide or conjugate thereof, an isolated nucleic acid molecule or a vector as described herein. In another example, the pharmaceutical composition further comprises one or more pharmaceutically acceptable excipients, vehicles or carriers.

Examples of pharmaceutically acceptable excipients, carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The isolated cytotoxic peptide or conjugate thereof as described herein may be present in the compositions in any of a wide variety of forms. For example, two, three, four or more peptides or conjugates thereof may be merely mixed together or may be more closely associated through complexation, crystallization, or ionic or covalent bonding. The peptides or conjugates thereof can also be formulated as prodrugs.

The term "prodrug" as used herein refers to compounds that rapidly convert in vivo into pharmacologically active compounds. Suitable prodrugs can be made, for instance, by conjugating the isolated cytotoxic peptide as described herein to one or more protective peptides. Various linkers known in the art can be used in such conjugations, for example but not limited to valine-citrulline dipeptide linker. Such linkers can be cleavable, resulting in the release of the pharmacologically active compounds. For example, valine-citrulline dipeptide linker is cleavable by lysosomal cathepsin B, resulting in the release of the cytotoxic peptide.

The isolated cytotoxic peptide or conjugate thereof, the isolated nucleic acid molecule and the vector as described herein can also be used in combination with one or more other therapeutic agents to achieve better results of treatment and/or to reduce potential side effects. Thus, in one example, the pharmaceutical composition further comprises one or more therapeutic agent. The isolated cytotoxic peptide or conjugate thereof, the isolated nucleic acid molecule and/or the vector as described herein may be administered simultaneously, sequentially or separately from the one or more further therapeutic agent. By simultaneous is meant that the isolated cytotoxic peptide or conjugate thereof, the isolated nucleic acid molecule or the vector as described herein may be contained in the same pharmaceutical composition as the one or more further therapeutic agent, or they are contained in different pharmaceutical compositions but taken at the same time. By sequential is meant that the isolated cytotoxic peptide or conjugate thereof, the isolated nucleic acid molecule or the vector as described herein and the one or more further therapeutic agent are contained in different pharmaceutical compositions, and are administered one immediately after another. By separately is meant the isolated cytotoxic peptide or conjugate thereof, the isolated nucleic acid molecule or the vector as described herein and the one or more further therapeutic agent are contained in different pharmaceutical compositions, and are administered with a period of time apart. For example, they can be administered separately with about 12 hours, 10 hours, 8 hours, 6 hours, 4 hours, 2 hours, 1 hour, 30 minutes, or 15 minutes apart. In some examples, when the isolated cytotoxic peptide or conjugate thereof, the isolated nucleic acid molecule or the vector as described herein and the one or more further therapeutic agent are contained in different pharmaceutical compositions, they can be administered using different routes.

The one or more therapeutic agent can be therapeutic agent against cancer, therapeutic agent for weight loss, or therapeutic agent with other effects, including but not limited to, reducing inflammation, reducing infection and relieving pain. In one example, the one or more therapeutic agent is a therapeutic agent against cancer, including but not limited to, general chemotherapeutic agents such as alkylating agents, antimetabolites, anti-tumor antibiotics, topoisomerase inhibitors, mitotic inhibitors and corticosteroids, inhibitors of translation and transcription; immunotherapeutic agents such as antibodies, in particular monoclonal antibodies, cytokines and vaccines; and targeted therapeutic agents such as small molecule drugs. In another example, the one or more therapeutic agent is a therapeutic agent for weight loss, including but not limited to, benzphetamine, bupropion hydrochloride, diethylpropion, lorcaserin, methamphetamine, naltrexone hydrochloride, orlistat, phendimetrazine, phentermine and sibutramine.

The isolated cytotoxic peptide or conjugate thereof, the isolated nucleic acid molecule, the vector or the pharmaceutical composition as described herein can be administered in a number of ways depending upon whether local or systemic administration is desired and upon the area to be treated. For example, administration may be oral, intraadiposal, intraarterial, intraarticular, intracranial, intradermal, intralesional, intramuscular, intranasal, intraocularal, intrapericardial, intraperitoneal, intrapleural, intraprostatical, intrarectal, intrathecal, intratracheal, intratumoral, intraumbilical, intravenous, intravesicularl, intravitreal, liposomal, local, mucosal, enteral, parenteral, rectal, subconjunctival, subcutaneous, sublingual, topical, transbuccal, transdermal, vaginal, in crèmes, in lipid compositions, via a catheter, via a lavage, via continuous infusion, via infusion, via inhalation, via injection, via local delivery, via localized perfusion or any combination thereof. One skilled in the art will be able to identify the method to adapt the pharmaceutically active component to the characteristics suitable for the selected route of administration. Such characteristics include, but are not limited to, solubility, stability, and deliverability.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, emulsions, and liposome-containing formulations. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms including, but not limited to tablets, capsules, liquid syrups and soft gels. The compositions as described herein may also be formulated as suspensions in aqueous, non-aqueous or mixed media. Aqueous suspensions may further contain substances that increase the viscosity of the suspension including, for example, sodium carboxymethyl cellulose, sorbitol and/or dextran. The suspension may also contain stabilizers.

The compositions as described herein may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, including but not limited to, lubricants, preservatives, stabilizers, wetting agents, emulsifiers, salts for influencing osmotic pressure, buffers, colorings, flavorings and/or aromatic substances and the like which do not deleteriously interact with the antibody(s) of the formulation.

The isolated cytotoxic peptide or conjugate thereof, the isolated nucleic acid molecule, the vector or the pharmaceutical composition as described herein can be used in the treatment or prevention of diseases. Examples of such diseases include, but are not limited to, cancer and obesity. Thus, in one example, there is provided a method of treating or preventing, for example, but not limited to cancer and obesity, in a subject comprising administering an isolated cytotoxic peptide as described herein, an isolated nucleic acid molecule as described herein, a vector as described herein or a pharmaceutical composition as described herein.

In another example, there is provided an isolated cytotoxic peptide or conjugate thereof as described herein, an isolated nucleic acid molecule as described herein, a vector as described herein or a pharmaceutical composition as described herein, for use in treating or preventing, for example, but not limited to cancer and obesity, in a subject.

In yet another example, there is provided use of an isolated cytotoxic peptide or conjugate thereof as described herein, an isolated nucleic acid molecule as described herein or a vector as described herein in the manufacture of a medicament for treating or preventing, for example, but not limited to cancer and obesity, in a subject.

The major types of cancers that can be treated include but are not limited to carcinoma, sarcoma, lymphoma, germ cell tumor and blastoma. The specific types of cancers that can be treated include but are not limited to breast cancer, colorectal cancer, gastric cancer, melanoma, pancreatic cancer, skin cancer, leukemia, myeloma, hepatocellular cancer, pancreatic cancer, cervical cancer, ewings tumour, neuroblastoma, kaposis sarcoma, prostate cancer, bladder cancer, melanoma, lung cancer—non small cell lung cancer (NSCLC), and small cell lung cancer (SCLC), head and neck cancer, renal cancer, lymphoma, prostate cancer, neuroblastoma, a blood cancer, testicular cancer, ovarian cancer, liver cancer or esophageal cancer, cervical cancer, non-melanoma skin cancer, glioblastoma, carcinoma, uterus cancer, chronic lymphoid leukemia, lymphoblastic leukemia, follicular lymphomas, melanomas, malignant homeopathies, acute leukemia, basal cell carcinoma, bone cancer, brain and central nervous system (CNS) cancer, connective tissue cancer, eye cancer, kidney cancer, larynx cancer, Hodgkin's lymphoma, non-Hodgkin's lymphoma, oral cavity cancer (for example, lip, tongue, mouth, and pharynx), and rhabdomyosarcoma. In one specific example, the cancer is breast cancer.

In some examples, the cancer is invasive and/or metastatic cancer. In some other examples, the cancer is stage I cancer, stage II cancer, stage III cancer or stage IV cancer.

Stem cell therapy is a promising treatment for various diseases such as cancers, cardiovascular diseases, brain and spinal cord injury, blood related diseases, Parkinson's disease, Alzheimer's disease, diabetes, wound healing and so forth. The major types of stem cells include but are not limited to, embryonic stem cells, induced pluripotent stem cells and tissue stem cells. One main concern of the stem cell therapy, in particular the therapy using embryonic stem cells or induced pluripotent stem cells, is that the transplantation of any undifferentiated stem cells can lead to side effects such as the formation of teratoma, which is a tumor containing tissues derived from all three embryonic germ layers, i.e., ectoderm, mesoderm, and endoderm. To prevent the formation of teratoma resulted from stem cell transplantation, drugs with specific cytotoxic effect against undifferentiated stem cells can be used.

Thus, in one example, the isolated cytotoxic peptide or conjugate thereof, the isolated nucleic acid molecule, the vector or the pharmaceutical composition as described herein can be used in the prevention or treatment of diseases associated with stem cell transplantation. In some examples, the stem cell transplantation can be, but not limited to, transplantation of embryonic stem cells, transplantation of induced pluripotent stem cells, or transplantation of tissue stem cells, or a mixture thereof. One example of such diseases is teratoma. In some examples, the teratoma is benign, while in some other examples, the teratoma is malignant.

In another example, there is provided an isolated cytotoxic peptide or conjugate thereof as described herein, an isolated nucleic acid molecule as described herein, a vector as described herein or a pharmaceutical composition as described herein, for use in preventing or treating diseases associated with stem cell transplantation in a subject.

In yet another example, there is provided use of an isolated cytotoxic peptide or conjugate thereof as described herein, an isolated nucleic acid molecule as described herein or a vector as described herein in the manufacture of a medicament for preventing or treating diseases associated with stem cell transplantation in a subject.

In some examples, the subject that is being treated may be a mammal. In one specific example, the subject may be a human.

As used herein the terms "treatment", "treating", or other grammatical variants thereof, refers to any and all uses which remedy a disease state or symptoms, prevent the establishment of disease, or otherwise prevent, hinder, retard, or reverse the progression of disease or other undesirable symptoms in any way whatsoever. Treatments of cancer include but are not limited to: (i) the prevention or inhibition of cancer or cancer recurrence, (ii) the reduction or elimination of symptoms or cancer cells, and (iii) the substantial or complete elimination of the cancer in question. Treatment may be effected prophylactically (prior to the onset of the disease) or therapeutically (following diagnosis of the disease).

The isolated cytotoxic peptide or conjugate thereof, the isolated nucleic acid molecule, the vector or the composition as described herein may be provided in an amount that is therapeutically effective. The suitable amount includes a sufficient but non-toxic amount of the compound as described herein to provide the desired therapeutic effect. The exact amount required will vary from subject to subject depending on factors such as the species being treated, the age and general condition of the subject, the severity of the condition being treated, the particular agent being administered, the mode of administration, and so forth, and may be determined by one of ordinary skill in the art using only routine experimentation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of the composition. In general, dosage is from 0.01 µg to 100 g/kg of body weight, such as 0.01 g to 100 g, 0.05 µg to 90 g, 0.1 µg to 80 g, 0.5 µg to 70 g, 1 µg to 60 g, 10 µg to 50 g, 20 µg to 40 g, 30 µg to 30 g, 40 µg to 20 g, 50 µg to 10 g, 75 µg to 5 g, 100 µg to 4 g, 200 µg to 3 g, 300 µg to 2 g, 400 µg to 1 g, 500 µg to 900 mg, 600 µg to 800 mg, 700 µg to 700 mg, 800 µg to 600 mg, 900 µg to 500 mg, 1 mg to 400 mg, 2 mg to 300 mg, 3 mg to 200 mg, 3 mg to 100 mg, 4 mg to 90 mg, 5 mg to 80 mg, 6 mg to 70 mg, 7 mg to 60 mg, 8 mg to 50 mg, 9 mg to 40 mg, 10 mg to 30 mg or 15 mg to 25 mg/kg of body weight, and may be given once or more times daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the peptide or composition is administered in maintenance doses, ranging from 0.01 µg to 100 g/kg of body weight, once or more times daily, weekly, monthly, yearly, to once every 2 years.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention will be further described in greater detail by reference to specific Examples, which should not be construed as in any way limiting the scope of the invention.

Example 1—HEXIM1 BR Peptide Induces Cell Death in a P-TEFb- and p53-Independent Fashion HEXIM1 was originally identified from vascular smooth muscle cells treated with HMBA, an anti-proliferation compound. HEXIM1 is known as the inhibitor of P-TEFb. P-TEFb is a protein complex, which is composed of cyclin-dependent kinase 9 (CDK9) and a cyclin partner (cyclin T1, T2a, T2b, or K) with cyclin T1 being the predominant CDK9-associated cyclin. P-TEFb controls the elongation phase of RNAPII transcription and is required for transcriptional regulation of human immunodeficiency virus.

HEXIM1 exerts its inhibitory function on P-TEFb only when associated with the 7SK snRNA, while neither 7SK snRNA nor HEXIM1 alone instigates any effects. It is hypothesized that association of the 7SK snRNA with HEXIM1 leads to a conformational change that renders the cyclin T1-binding domain of HEXIM1 accessible for P-TEFb binding. HEXIM1 contains several functional domains and the domains required for 7SK snRNA and cyclin T1 binding have been identified. The N-terminus of HEXIM1, AA 1-150, has been characterized as a self-inhibitory domain (ID). Deletion of the ID enhances the inhibitory effects of HEXIM1 on P-TEFb activity. The region between AAs 150-180 of HEXIM1, which includes a stretch of basic residues, is referred to as the basic region (BR). The BR contains the binding motif for 7SK snRNA, KHRR (AAs 152-155). The P-TEFb binding motif, PYNT (AAs 202-205), is located between the BR and acidic region (AR, AAs 210-250). In the absence of 7SK snRNA, the AR can interact with the adjacent BR. Since the P-TEFb binding motif is located between the BR and AR, the BR-AR interaction may establish an auto-inhibitory conformation which prevents the association between HEXIM1 and P-TEFb. When 7SK snRNA binds to the BR, the BR-AR interaction is disrupted and the PYNT motif becomes accessible for P-TEFb binding. HEXIM1 can form a homodimer or a heterodimer with a HEXIM1-related protein, HEXIM2, through the dimerization domain (DD) at the C-terminus of HEXIM1.

When the 7SK snRNA binding motif, KHRR, is mutated to ILAA, the mutant HEXIM1 cannot interact with 7SK snRNA or regulate P-TEFb activity (FIG. 1B). It was found that FGF-BR-ILAA mutant still maintained its killing ability, in both HCT116 WT and p53 null cell lines, suggesting that P-TEFb might not be involved in the HEXIM1 BR-mediated cell killing (FIG. 1D).

HEXIM1 stabilizes p53 by blocking the HDM2-mediated ubiquitination of p53 and plays an essential role in p53 activation induced by anti-cancer drugs/compounds. HDM2, a p53-specific E3 ubiquitin ligase, is the master regulator of p53. Ubiquitination of p53 by HDM2 results in proteasome-mediated degradation of p53 protein. Six lysine residues, Lys-370, -372, -373, -381, -382, and -386, located within the C-terminal domain of p53 are known as the target residues for HDM2 ubiquitination. Six lysine residues located within the BR of HEXIM1 (Lys-150-152 and 159-161) are identified as the major sites for HDM2 ubiquitination. Sequence alignment of the ubiquitination sites between p53 (AAs 370-386) and HEXIM1 (AAs 150-161) exhibits similar distribution of the lysine residues (FIG. 1A). This suggests that HEXIM1 peptide containing these ubiquitination sites may have an impact on p53 activation, resulting in p53-dependent cell arrest or cell death.

A commercial p53 activating peptide, FGF-p53, containing the p53 ubiquitination sites (AAs 361-382) fused with a cell membrane-translocating peptide derived from Kaposi fibroblast growth factor, was reported to induce apoptosis in mutant and wild-type p53-bearing human cell lines. The internalized p53 peptide is likely to compete with the endogenous p53 protein in binding to HDM2 and protect the endogenous p53 from HDM2-mediated ubiquitination, resulting in stabilization and activation of p53. A FGF-BR fusion peptide was generated in the present disclosure, in which the cell penetrating FGF peptide was fused with HEXIM1 BR peptide containing the HDM2 ubiquitination residues (AAs 150-161). Two acute myeloid leukemia (AML) cell lines, AML2 and AML3, were treated with FGF-p53 and FGF-BR peptides and the effects of the peptides on cell viability were determined. FGF-p53 exhibited anti-proliferation effects on AML2 cells at high dosage (30 µM) but had no effects on AML3 cells (FIG. 11). The p53 level in AML2 has been shown to be significantly higher than that in AML3. This observation explained the p53-dependent anti-proliferation effects of FGF-p53 peptide in AML2 cells. However, FGF-BR peptide exhibited similar cytotoxicity on both cell lines and much stronger inhibition than FGF-p53 peptide, raising the possibility that the killing mediated by FGF-BR might not depend on p53 (FIG. 11).

Cytotoxicity was also observed in human cervical cancer cells, HeLa cells, when treated with FGF-BR peptide (FIG. 1C). Comparable cytotoxicity was also observed in normal cells, including HEK293 cells and human foreskin fibroblasts (HFFs) (FIG. 1C), suggesting the cytotoxic effect of BR peptide occurs to all cell types once it is internalized into cells.

The effect of FGF-BR peptide was also tested in human colon cancer cell line, HCT116 (p53 KO). The HCT116 (p53 WT) was used as a control. FGF-BR induced cell death in both HCT116 (p53 WT) and HCT116 (p53 KO) cell lines with similar potency, while the negative control peptide, FGF-X13, showed no effects in both cell lines (FIG. 1D). A fusion peptide, FGF-BR-RRR12 was generated, in which all six HDM2 ubiquitinating lysine residues were mutated to arginine and could no longer be ubiquitinated by HDM2 (FIG. 1B). If the BR peptide indeed induces cell death through the HDM2-p53 regulatory pathway, the BR-RRR12 mutant should lose its cytotoxic effects. FGF-BR-RRR12 did not exhibit reduced inhibitory effects but demonstrated stronger cell toxicity when compared to the wild-type FGF-BR peptide (FIG. 1D). It was also noticed that the p53 status had no effects on the cell killing mediated by FGF-BR-RRR12 (FIG. 1D), confirming that the cell death caused by the BR peptide was not p53-dependent.

Example 2—HEXIM1 BR Induced Cell Death is Independent of Apoptosis

Figure 2:
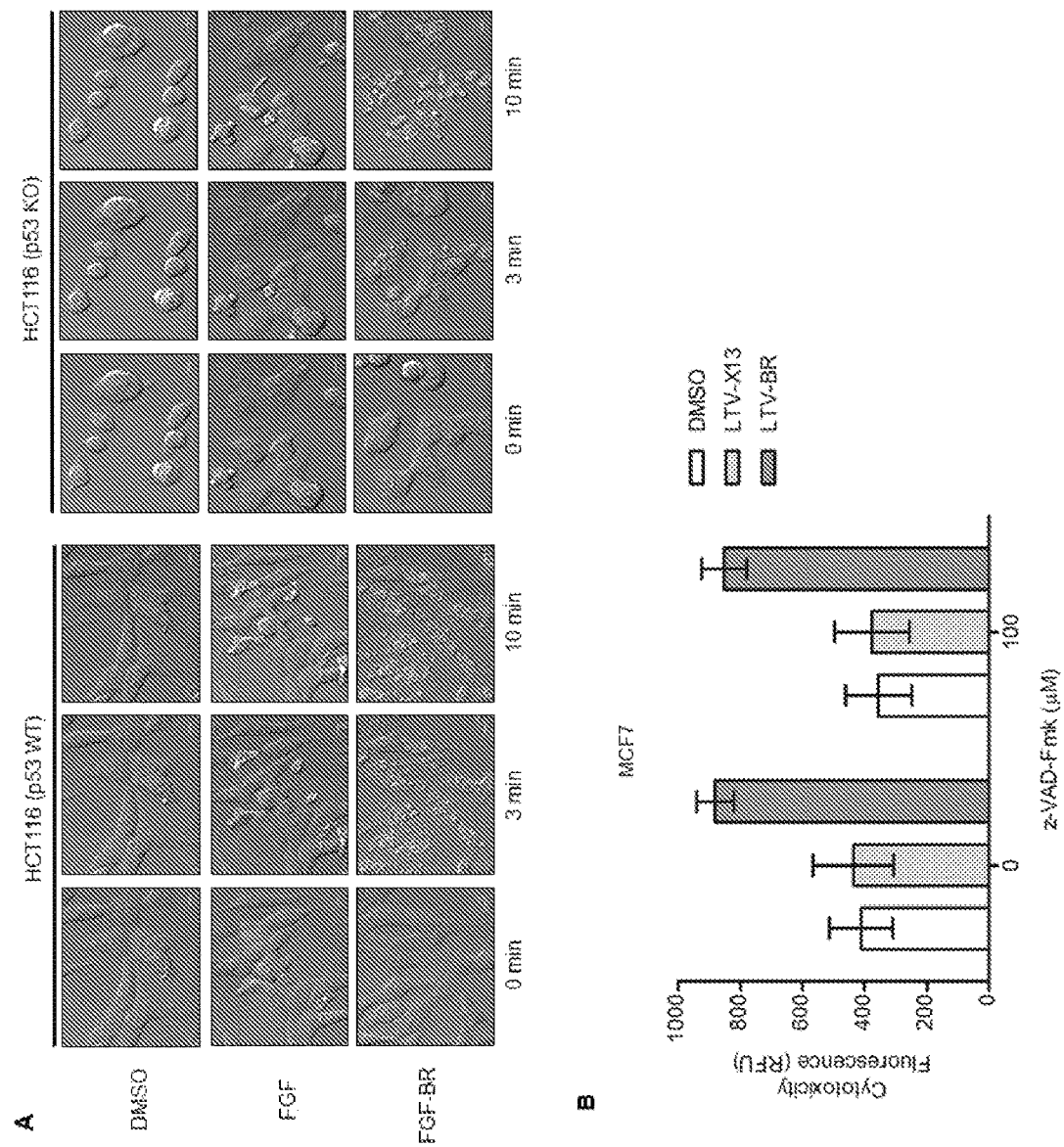
FIG. 2 shows FGF-/LTV-tagged BR peptide induced rapid cell death independently of apoptosis. (A) shows representative time-lapse differential interference contrast (DIC) snapshots of treated HCT116 (p53 WT) and HCT116 (p53 KO) cells (bar represents 100 µm). HCT116 (p53 WT) and HCT116 (p53 KO) cells were cultured on glass slides overnight, treated with vehicle control (0.5% dimethyl sulfoxide (DMSO)) or the indicated FGF peptides (30 µM). Time-lapse DIC imaging highlights dynamic morphological changes in treated HCT116 cells by spinning disk confocal microscopy. The results indicate that in both HCT116 (p53 WT) and HCT116 (p53KO) cell lines, FGF tag alone does not affect morphology or viability of the cells. In contrast, FGF-BR peptide rapidly induces drastic changes to the cell morphology with rupturing of the plasma membrane accompanied with damages to the nuclear membrane and abnormalities to the nucleolus in both cell types. (B) cytotoxicity fluorescence plots of breast cancer cells MCF7 showing the effect of pan-caspase inhibitor z-VAD-Fmk on cells treated with LTV-tagged BR peptide. LTV is a breast cancer cell targeting peptide. MCF7 cells were incubated with or without z-VAD-Fmk (for 90 min) and then with indicated LTV-tagged peptides (30 µM) for thirty minutes at 37° C. Cells treated with LTV-X13 peptide (SEQ ID NO: 14) or vehicles, DMSO (0.5%), were used as negative controls. Treated cells were subjected to the cytotoxicity assay as described in Example 9—Materials and Methods. Data representative of at least three independent experiments performed in triplicate were shown with values expressed as mean±SD. The results indicate that LTV-tagged BR (SEQ ID NO: 15) has significant cytotoxic effect on MCF7 cell line, and the effect could not be inhibited by z-VAD-Fmk.

The mechanism of cell death induced by the HEXIM1 BR peptide was examined. To monitor the real-time changes to the cells upon treatment with BR peptide, the effect of FGF-BR on HCT116 ($p^{53}$ WT) and HCT116 ($p^{53}$ KO) cells was examined in a live cell imaging setting. Cells treated with FGF peptide were included as a control. Within minutes, FGF-BR peptide rapidly induced drastic changes to the cell morphology with rupturing of the plasma membrane accompanied with damages to the nuclear membrane and abnormalities to the nucleolus in both cell types (FIG. 2A). No effects were detected when cells were treated with FGF peptide (FIG. 2A). Similar observations were seen in MCF7 breast cancer cells treated with LTV-tagged BR peptide, where BR peptide was conjugated to a breast cancer-targeting peptide, LTV (data not shown). Since BR-induced cytotoxicity occurred in minutes, whereas the duration of apoptosis is estimated to be from 12 to 24 hours, it is unlikely that FGF-BR lead to apoptosis. Moreover, the morphological changes seen in FGF-BR treated HCT116 cells do not resemble the characteristics of cells dying by apoptosis which include membrane blebbing and formation of apoptotic bodies. Cell swelling and subsequent rupturing of the plasma membrane followed by rapid lysis of the cells observed were descriptive of necrosis instead. In addition, the induction of cell death in LTV-BR-treated MCF7 cells could not be inhibited by a pan-caspase inhibitor z-VAD-Fmk (100 µM) (FIG. 2B), indicating that BR induced cell death is independent of apoptosis.

Taken together, it is unlikely that the conjugated FGF-BR peptide triggered apoptosis in the treated cells. Hence, using this BR peptide provides an attractive approach to eliminate cancer cells that have a defective apoptotic pathway.

Figure 3:
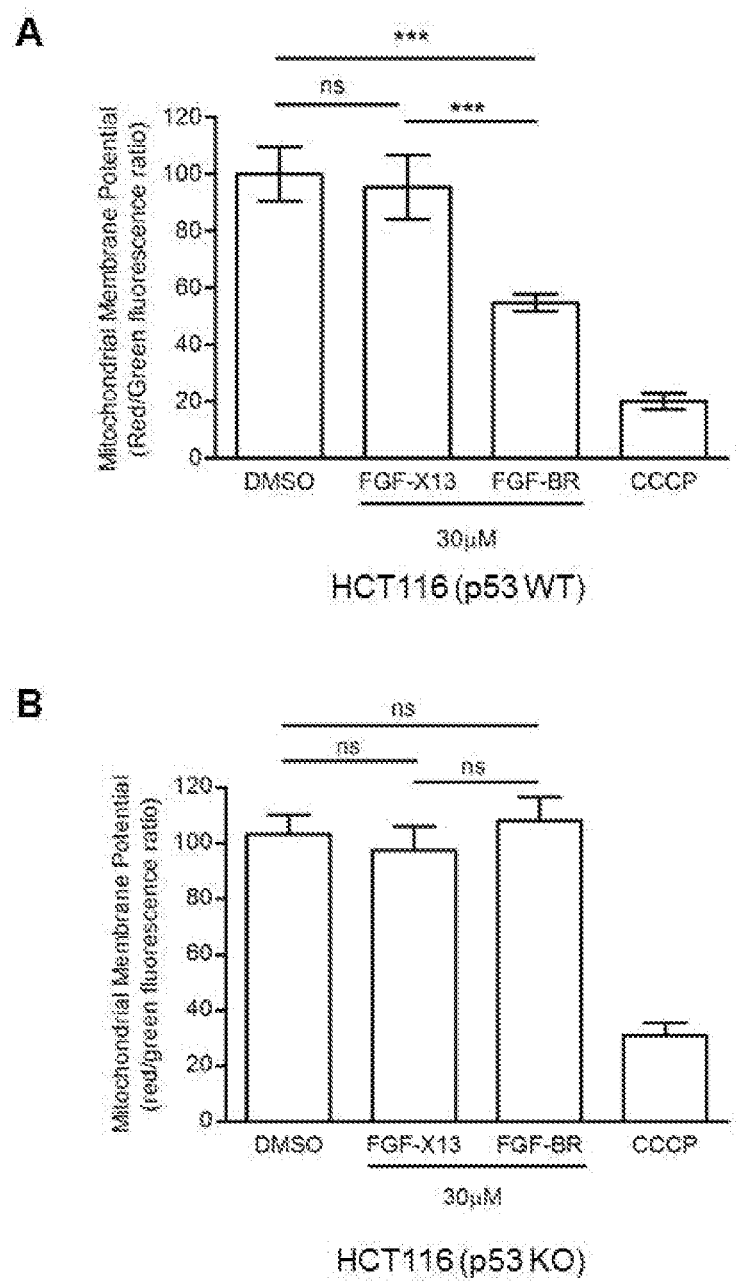
FIG. 3 shows FGF-tagged BR peptide decreases mitochondrial membrane potential in HCT116 (p53 WT) cell line but not in HCT116 (p53 KO) cell line. (A) shows bar chart of mitochondrial membrane potential in HCT116 (p53 WT) cell line treated with negative and positive controls and the FGF-tagged BR peptide. (B) shows bar chart of mitochondrial membrane potential in HCT116 (p53 KO) cell line treated with negative and positive controls and the FGF-tagged BR peptide. HCT116 (p53 WT) and HCT116 (p53 KO) cells were cultured in 96-well plates, treated with indicated FGF-tagged peptides (30 µM) for three minutes. A mitochondrial membrane depolarizer, carbonyl cyanide 3-chlorophenylhydrazone (CCCP), was used as a positive control. Cells treated with FGF-X13 peptide or vehicle, DMSO (0.5%), was used as negative controls. Treated cells were subjected to mitochondrial membrane potential (MMP) measurement using JC-1 fluorescence-based assay for six independent experiments. Results were summarized as mean±SD (***, P<0.0001; ns: not significant, Student's t test). The results indicate that FGF-tagged BR peptide decreased mitochondrial membrane potential in HCT116 cell line is dependent on p53.

Example 3—HEXIM1 BR Induces Rapid Depolarization of Mitochondrial Membrane Potential in a p53-Dependent Manner It has been reported that a cytotoxic basic peptide, KLA, elicit its killing action by disrupting the mitochondrial membrane potential (MMP), which is important for ATP generation and induction of apoptosis. Since HEXIM1 BR contains many basic residues, it is possible that the BR may utilize similar mechanism for its potent killing. MMP was measured using JC-1 dye after incubating with FGF-X13 or FGF-BR peptides for three minutes. Carbonylcyanide m-chlorophenylhydrazone (CCCP), a known mitochondrial membrane depolarizer, was used as a positive control. FGF-BR treated HCT116 (p53 WT) cells experienced rapid mitochondrial depolarization within three minutes (FIG. 3A), which is similar to the time frame that morphological changes occurred upon addition of the FGF-BR peptide (FIG. 2A). However, no mitochondrial depolarization was observed in HCT116 ($p^{53}$ KO) cells treated with FGF-BR (FIG. 3B), although these cells encountered rapid cytotoxicity similar to HCT116 (p53 WT) cells (FIG. 2A). It was known that p53 would translocate to the mitochondria, resulting in the reduction of MMP in p53-mediated apoptosis. Collectively, the data shows that HEXIM1 BR peptide is likely to induce cell killing though an alternative pathway that acts independently of p53 and apoptosis.

Figure 4:
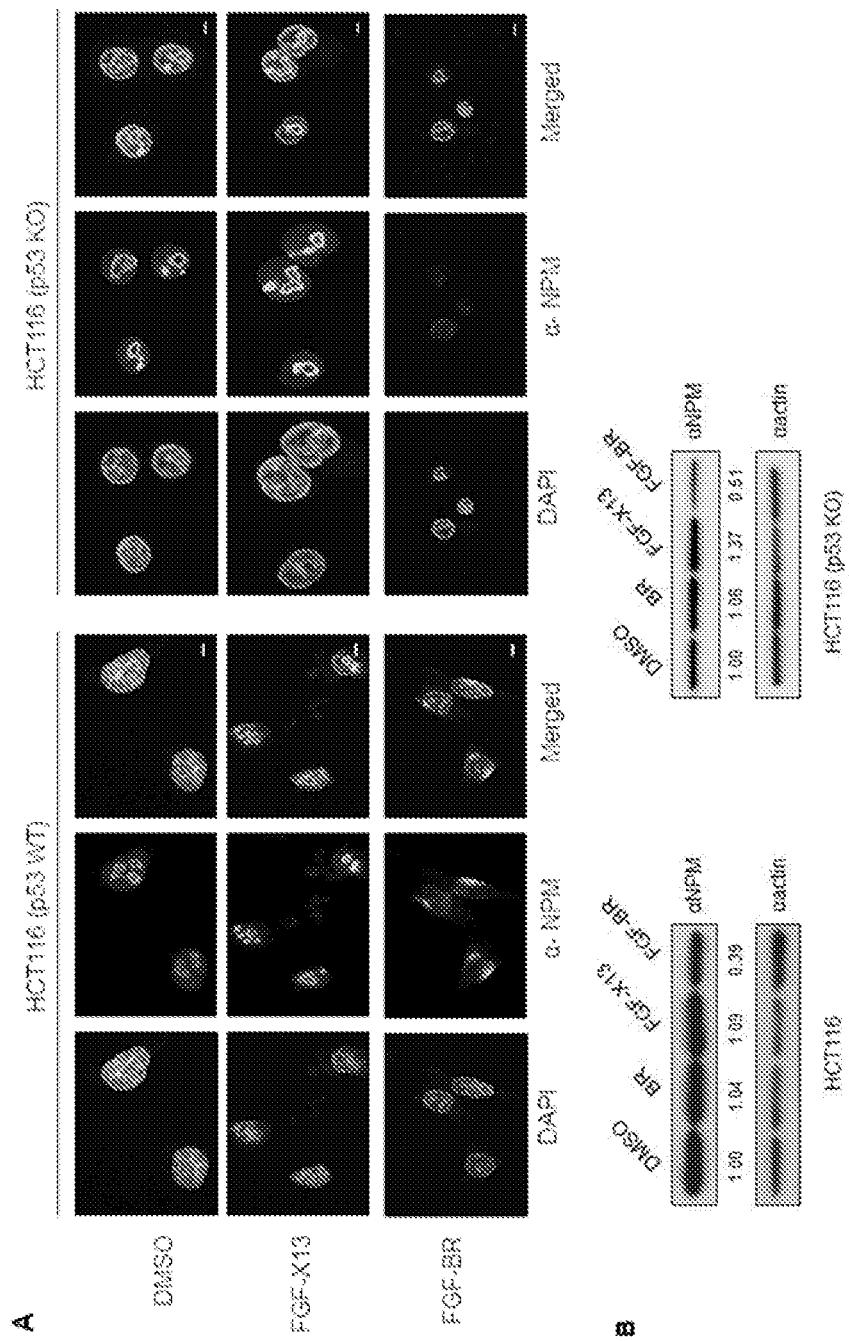
FIG. 4 shows FGF-tagged BR peptide alters the sub-cellular localization and protein level of endogenous NPM. (A) representative immunofluorescence images showing the sub-cellular localization of α-NPM (bar represents 10 µm). HCT116 (p53 WT) and HCT116 (p53KO) cells were cultured on glass slides overnight, treated with FGF-X13 or FGF-BR (30 µM). Cells treated with FGF-X13 peptide or vehicle, DMSO (0.5%), was used as controls. Treated cells were immunostained with an anti-NPM antibody and analyzed by laser scanning confocal microscopy (Zeiss). Nuclei were visualized by staining with 4',6-diamidino-2-phenylindole (DAPI). The results indicate that NPM is mislocated into the cytoplasm in cells treated FGF-tagged BR peptide, in both HCT116 ($p^{53}$ WT) and HCT116 (p53 KO) cell lines. (B) results of western blot showing the expression level of α-NPM protein (α-actin was used as the internal control. HCT116 cells were plated overnight prior to addition of vehicle control (0.5% DMSO) or indicated peptides (30 µM) at 37° C. Lysates were subsequently harvested and subjected to western blotting with anti-NPM and anti-actin antibodies. The level of NPM protein was quantified as described in Example 9—Materials and Methods. The results show that endogenous level of NPM is reduced in cells treated with FGF-tagged BR peptide, in both HCT116 (p53 WT) and HCT116 (p53 KO) cell lines.

Example 4—HEXIM1 BR Peptide Alters Subcellular Localization of NPM and Reduces its Protein Expression NPM is a multi-functional protein and participates in the process of ribosome biogenesis. In addition to its role in protein translation, NPM is required to maintain DNA integrity in cells. Knockout of NPM results in accumulation of DNA damage, which clearly indicates the essential role of NPM in cell proliferation and survival. NPM is located in nucleolus, the sub-cellular site of ribosome synthesis and assembly. About 35% of AML patients carry the cytoplasmic-misallocated mutant form of NPM, NPMc+. NPMc+ is found to interact and sequester a portion of HEXIM1 in the cytoplasm of the NPMc+ AML cell line and activates P-TEFb-dependent transcription, suggesting the involvement of HEXIM1 in tumorigenesis of AML. The BR domain of HEXIM1 was known to contain a nucleolar localization sequence. When the BR was fused with yellow fluorescent protein (YFP), the BR-YFP was found to localize in nucleoli. NPM was identified as a HEXIM1 binding protein, and the BR of HEXIM1 was required for NPM binding. To determine the effects of FGF-BR peptide on NPM, immunofluorescence was performed to examine the sub-cellular distribution of NPM in the FGF-BR-treated HCT116 (p53 WT) and HCT116 (p53 KO) cells. Normal nucleolar localization of NPM was observed in control experiments (FIG. 4A, DMSO and FGF-X13), while mislocalization of NPM was detected in both cell types when incubated with FGF-BR (FIG. 4A, FGF-BR). Furthermore, in both cell types, a reduction in NPM protein level was observed in the FGF-BR treated cells as compared to the FGF-X13 control (FIG. 4B). Various post-translational modifications of p53, such as phosphorylation and acetylation, have been shown to stabilize and activate p53 in response to cellular stress. The expression levels of phosphorylation of p53 on Ser15 and acetylation of p53 on Lys382 were investigated, and it was found that they remained unchanged in HCT116 (p53 WT) cells when treated with FGF-BR peptide (data not shown), suggesting a p53-independent pathway to trigger cell death. These results demonstrated that the BR peptide may interfere with protein translation/ribosome biosynthesis by disrupting sub-cellular localization of NPM and decreasing its expression, hence compromising its normal function.

Example 5—Selective Killing of LTV-BR Fusion Peptide on Breast Cancer Cells

Therapeutic peptides can be divided into two major categories: cell targeting and cytotoxic peptides. Targeting peptides, including the cancer targeting peptides, provide selectivity and specificity to direct the targeted treatment. Cytotoxic peptides can be used as the toxin/payload in fusion peptides, nano-particle conjugates, and antibody drug conjugates (ADCs) for potential cancer treatment.

Figure 5:
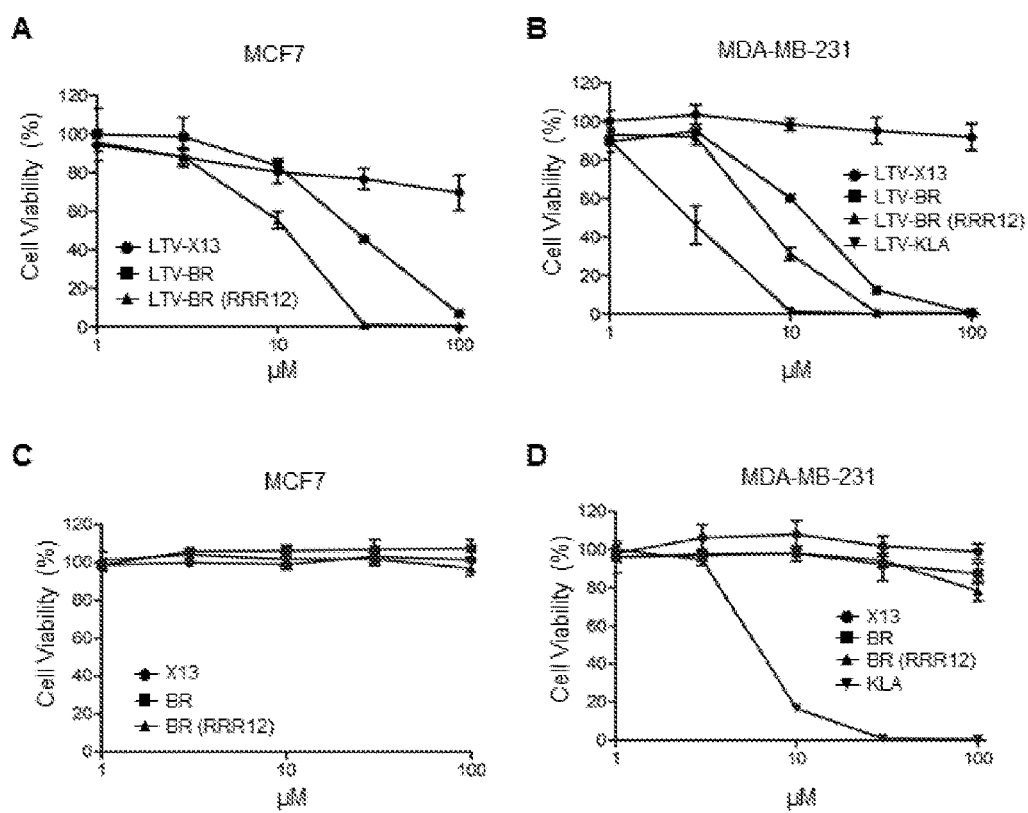
FIG. 5 Cell viability plots showing the effects of LTV-tagged BR peptide and variants thereof, as well as untagged BR peptide and variants thereof, in two breast cancer cell lines, (A) MCF7 and (B) MDA-MB-231. Cells were treated with indicated LTV-tagged peptides at different concentrations overnight before cell viability assays were performed. Both LTV-tagged BR and LTV-tagged BR (RRR12) peptides decreased cell viability in (A) MCF7 and (B) MDA-MB-231 cell lines. Effects of the indicated un-tagged peptides on the viability of (C) MCF7 and (D) MDA-MB-231 cells were analyzed by cell viability assays. The untagged X13 was used as a negative control. The results indicate that untagged BR and BR (RRR12) peptides have no effect on cell viability in (C) MCF7 and (D) MDA-MB-231 cell lines. Data representative of at least three independent experiments performed in triplicate were shown with values expressed as mean±SD. The results indicate that LTV-tagged BR peptide decreases cell viability in breast cancer cells, while BR peptide alone shows no effect on cell viability.

To explore the potential use of the cytotoxic HEXIM1 BR peptide in cancer therapy, a breast cancer targeting peptide, LTV, was fused to HEXIM1 BR and BR-RRR12 to generate the fusion peptide, LTV-BR and LTV-BR-RRR12 (SEQ ID NO: 16). Both LTV-BR and LTV-BR-RRR12 peptides exhibited anti-proliferation effects in breast cancer cell lines MCF7 and MDA-MB-231, while no effects were detected using the LVT-X13 control peptide (FIGS. 5A and 5B). Although MDA-MB-231 cells are triple-negative with the absence of expression of oestrogen receptor, progesterone receptor and HER2, LTV-BR and LTV-BR-RRR12 elicited similar anti-cancer activity as compared to MCF7 cells (FIG. 5B). In addition, untagged control X13 (SEQ ID NO: 12) and the two BR peptides had no effect on cell viability (FIGS. 5C and 5D).

Figure 7:
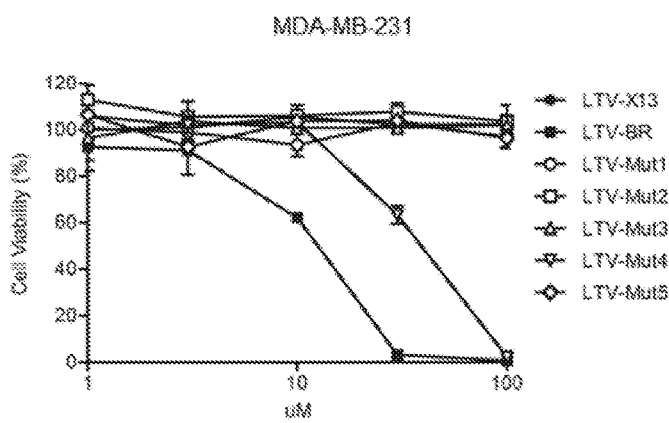
FIG. 7 shows cell viability plots (upper panel) of cells treated control, LTV-tagged BR and mutated variants thereof (sequences indicated in the lower panel). MDA-MB-231 breast cancer cells were treated with indicated truncated LTV-tagged peptides at various concentrations overnight before cell viability assays were performed. Cells treated with LTV-X13 were used as negative control, cells treated with LTV-BR were used as positive control. Data representative of at least three independent experiments performed in triplicate were shown with values expressed as mean±SD.

To define the active region of the BR peptide, a series of truncated BR peptides were generated based on the stretches of basic residues found in the BR peptide sequence. These truncated peptides were fused to LTV (SEQ ID Nos: 22-26) and introduced to MDA-MB-231 cells. The results suggest that the region encompassing the second and third stretch of basic residues (HRRRPSKKKRHW) is more critical in exerting cytotoxic activity as compared to the first stretch of basic residues (FIG. 7). To confirm this hypothesis, stretches of basic residues were replaced by alanine residues in the active region of BR (see SEQ ID Nos: 27-33). Results shown in FIG. 8 demonstrated the importance of the same stretches of basic residues (HRRRPSKKKRHW) in BR induced cytotoxicity. Nonetheless, all three stretches of basic residues are required to exhibit the maximum cytotoxic effect against MDA-MB-231 cells.

KLA peptide (SEQ ID NO: 13), a cytotoxic peptide, was often fused with a cancer-targeting peptide or conjugated to antibodies recognizing cancer cells (as antibody-drug conjugate, ADC) to exert cell-killing effect in anti-cancer therapy. LTV-KLA peptide (SEQ ID NO: 17) was generated and its effect was compared to that of LTV-BR. LTV-KLA exhibited stronger inhibition on the viability of MDA-MB-231 cells (FIG. 5B). However, it was noted that untagged KLA also showed non-specific killing on MDA-MB-231 cells, while BR- or BR-RRR12-treated cells remained highly viable (FIG. 5D). LTV-KLA also exhibited non-specific cell killing on non-breast cancer cell lines such as CHO (Chinese hamster ovary) and OPM-2 (multiple myeloma) cells, while little or no effects were observed in the LTV-BR-treated cells (FIGS. 9A and 9B). Similar observations were seen for normal human fibroblasts HFF and WI-38, indicating the specificity of LTV-BR towards breast cancer cell lines but not LTV-KLA (FIGS. 9C and 9D). It is predicted that a portion of the KLA ADCs will be broken down before reaching the target cancer cells, even though non-cleavable linkers may be used to generate these conjugates. As such, KLA peptides may be released from the conjugates, resulting in an off-target killing of normal cells/tissues. Taken together, the use of KLA as the toxic load in cancer therapy is questionable due to its non-specificity. In contrast, untagged HEXIM1 BR peptide is unable to kill cells when it is not fused with any cell penetrating or targeting peptides, suggesting that HEXIM1 BR peptide may be a safer alternative as compared to KLA, for the development of anti-cancer therapeutics.

Example 6—Cell Penetrating/Targeting Peptide is Required for Internalization HEXIM1 BR Peptide in Cells The HEXIM1 BR peptide did not cause any cytotoxic effects when it was not fused with cell penetrating (for example, FGF) or cancer cell targeting (for example, LTV) peptides. It is thus possible that the unfused BR peptide may fail to internalize into cells without specific guidance. To test this hypothesis, fluorescent-labelled BR and LTV-BR peptides were generated and their presence in cells was examined by confocal microscope.

Figure 6:
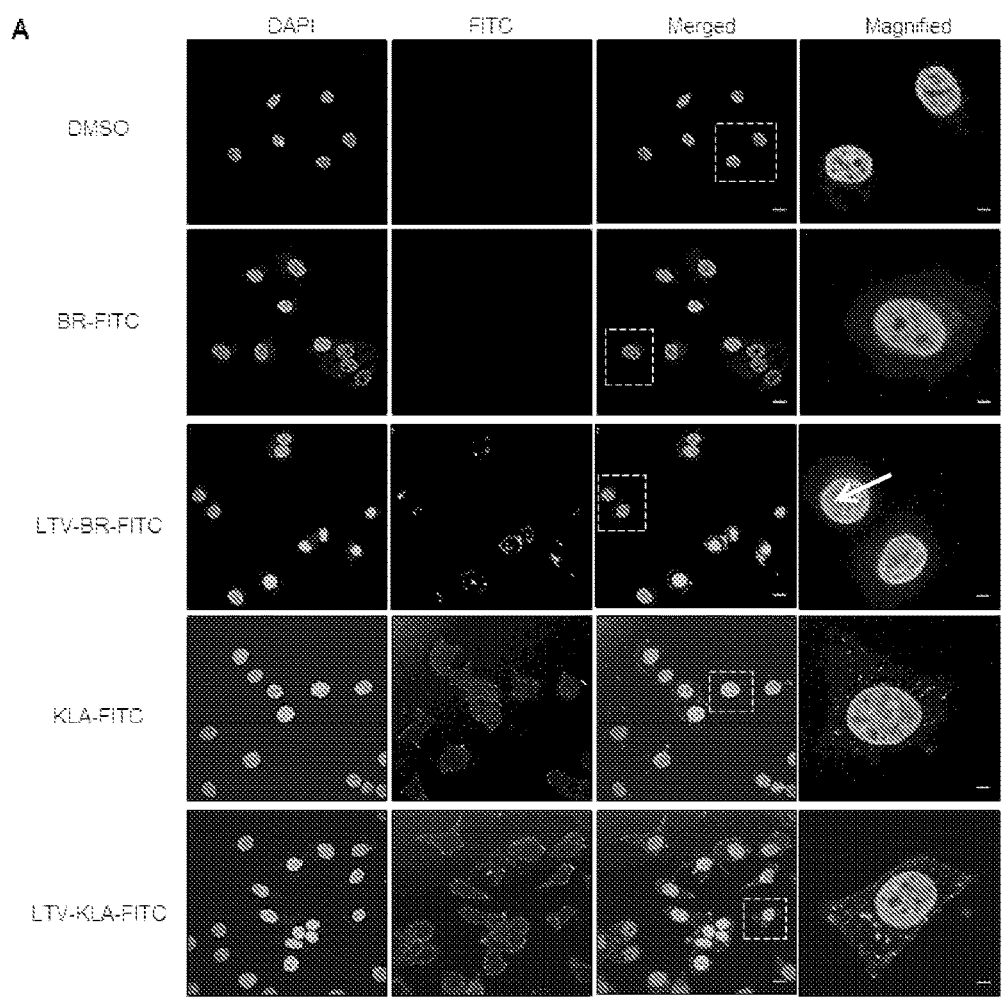
FIG. 6 shows the untagged HEXIM1 BR peptide fails to enter cells by itself, while another cytotoxic peptide, KLA, can enter the cell without a cell penetrating and/or cell targeting tag. (A) shows images of confocal microscopy of MCF7 cells treated with vehicle control and the indicated peptides (bar represents 10 µm). MCF7 cells were cultured on glass slides overnight before incubation with the indicated FITC-labeled peptides (30 µM) for 30 min and subsequently analyzed by laser scanning confocal microscopy. Nuclei were visualized by DAPI. Cells treated with vehicle, DMSO (0.5%) were used as control. Pointed arrow indicates FITC fluorescence. The results show that no FITC fluorescence can be defected in cells treated with BR-FITC peptide, while FITC fluorescence can be detected in cells treated with LTC-BR-FITC, KLA-FITC and LTV-KLA-FITC peptides. (B) shows bar chart of FITC-positive cells quantified by flow cytometry. Data represent percentage of fluorescence-positive cells in total cell population. Results were summarized as mean±SD of three independent experiments (***, P<0.0001, Student's t test). The results indicate that no significant cellular uptake of BR-FITC was observed, while the cellular uptake of KLA-FITC, LTV-BR-FITC and LTV-KLA-FITC is significantly higher compared to BR-FITC.
Figure 6:
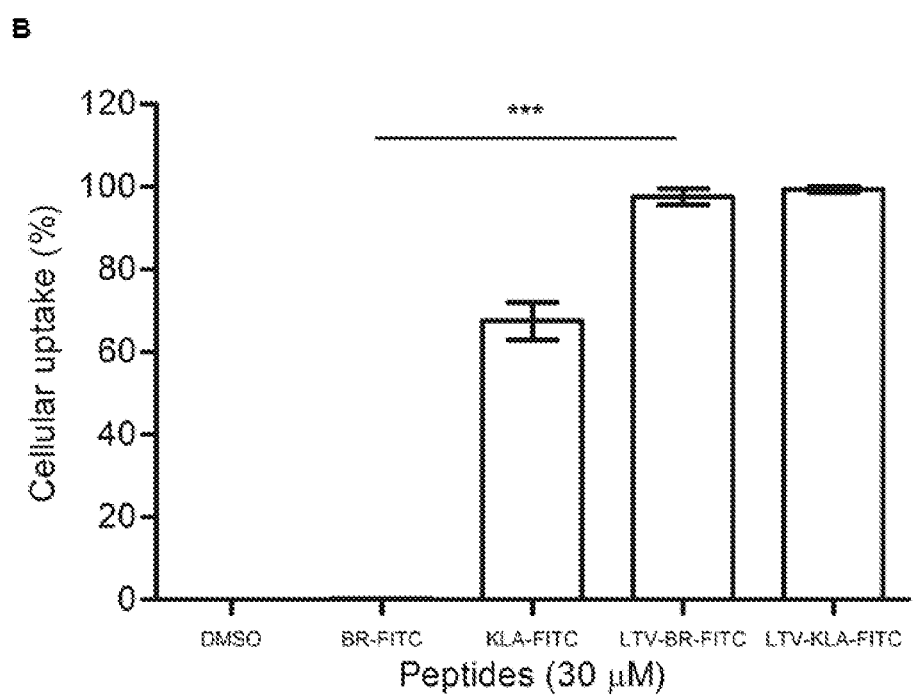

MCF7 cells were incubated with fluorescent-labeled peptides, followed by a washing step to remove the peptides failing to penetrate into cells. No fluorescent signals were observed in HEXIM1 BR peptide-treated cells (FIG. 6A), indicating that the BR peptide was not internalized. In the LTV-BR-incubated cells, fluorescent signals were detected within the cells (FIG. 6). LTV-BR was readily internalized into MCF7 cells and distributed in cytoplasm and nuclei (FIG. 6A). It was noted that its strong fluorescent signals were primarily localized in the nucleoli (FIG. 6A, LTV-BR-FITC). Detection of fluorescent signals in KLA-treated cells helps to explain the non-specific cytotoxicity induced by KLA peptide (FIG. 6A), while no fluorescent signal was observed in HEXIM1 BR-treated cells, indicating that the BR peptide could not enter the cells by itself (FIG. 6A, BR-FITC). Cells treated with LTV-KLA demonstrated that the sub-cellular localization of the peptide was observed mainly in the cytoplasm (FIG. 6A). The different distribution of LTV-BR and LTV-KLA suggests that BR and KLA may utilize different mechanisms for cell killing.

Flow cytometric analysis was also performed to quantify the amount of internalized fluorescent peptide in MCF7 cells. LTV peptide directed the uptake of almost 100% of LTV-fused peptides (LTV-BR and LTV-KLA) into the breast cancer cell line (FIG. 6B). Approximately 65% of KLA-FITC-treated MCF7 cells internalized KLA-FITC, whereas there was no entry of BR-FITC into MCF7 cells (FIG. 6B). These results clearly demonstrate the safety feature of HEXIM1 BR peptide when compared to the non-specific cytotoxic KLA peptide. LTV assisted in the cellular internalization of HEXIM1 BR peptide into its target cells and the nucleolar localization of the fusion peptide might be subsequently guided by BR peptide.

Example 7—Application of HEXIM1 BR Peptide in Weight Loss Study $2.5 \times 10^4$ cells/ml of mouse fibroblast cells 3T3 were cultured in gelatin coated plates in Dulbecco's Modified Eagle Medium (DMEM) supplemented with 10% fetal bovine serum (FBS) and 1% penicillin/streptomycin (Gibco) to reach 100% confluent. The cells were then maintained at 100% confluency by supplementing with fresh media in a 37° C. incubator with 5% $CO_2$ for 3 days. For induction, cells were then cultured in DMI Induction Media (which is DMEM supplemented with 10% fetal bovine serum, 1% penicillin/streptomycin, 0.1% 3-isobutyl-1-methylxanthine (sigma), 0.1% insulin (sigma) and 0.1% dexamethasone (sigma)) for 48 hours. The cells were then cultured in Insulin Induction Media (which is DMEM supplemented with 10% fetal bovine serum, 1% penicillin/streptomycin and 0.1% insulin). The insulin induction media was changed every 2 days until the cells were differentiated to adipose cells.

A D-form BR peptide with the sequence of QLGKKKHRRRPSKKKRHW was tagged to a fat tissue targeting peptide of the sequence CKGGRAKDC (ATS peptide, SEQ ID NO: 39) to generate the ATS-$BR_D$ peptide of the sequence CKGGRAKDCGG(QLGKKKHRRRPSKKKRHW)$_D$ (SEQ ID NO: 40). Both undifferentiated 3T3 cells and differentiated adipose cells were treated with the ATS-$BR_D$ peptide. ATS-tagged $KLA_D$ peptide was used as a positive control. Cell viability results shown in FIG. 10 indicates that the ATS-$BR_D$ peptide has no cytotoxic effect on undifferentiated 3T3 mouse fibroblast cells, but has significant cytotoxic effect on differentiated adipose cells. The cytotoxic effect of ATS-$BR_D$ peptide on adipose cells is of similar potency as ATS-$KLA_D$ peptide.

Example 8—Use of HEXIM1 BR Peptide as the Toxin for Antibody Drug Conjugates (ADCs)

To generate ADCs, the cytotoxic HEXIM1 BR peptides are covalently attached to antibodies through chemical linkers. Cysteine and lysine are two most naturally occurring amino acids which are used to attach the toxin through the linker to the antibody. To conjugate at the lysine residues of antibodies, two chemical linkers, N-succinidyl-3-(2-pyridylothio)propionate (SPDP) and succinimidyl 4-(N-maleimidomethyl)cyclohexane-1-carboxylate (SMCC), are utilized according to manufacturer's manual (Thermo Fisher Scientific). Briefly, the linkers are first crosslinked to the lysine residues of the antibodies. As the thiol group is required for conjugating the peptides to the chemical linkers, a cysteine residue is added at the N- or C-terminal of the BR peptide. After removing excess linkers and peptides, the effects of the BR-conjugated ADCs are analyzed in vitro using the selected breast cancer cell lines.

IgGs have four pairs of interchain disulfide bonds, two between the heavy chains in the hinge region and two on Fab between heavy and light chains. Intrachain disulfide bonds are to be left intact because they are critical to maintain the basic IgG domain structure essential for antigen recognition. Only partial reduction of the interchain disulfide bonds at the hinges gives eight potential conjugation sites through cysteine residues.

Example 9—Materials and Methods

Cell Lines—

Human cell lines including HeLa, HEK293, MCF7, MDA-MB-231, CHO-K1, OPM-2, and WI-38 were obtained from American Type Culture Collection. AML2 and AML3 cells were purchased from Deutsche Sammlung von Mikroorganismen und Zellkulturen. HCT116 p53+/+ and p53−/− cells were kindly given by Dr. Bert Vogelstein. Primary human foreskin fibroblasts (HFF) were obtained from Dr. Mark Stinski. HCT116, HCT116 (p53 KO), HeLa, 293, HFF, MCF7, CHO-K1, and WI-38 cells were cultured in Dulbecco's Modified Eagle Medium (DMEM) supplemented with 10% fetal bovine serum (FBS) and 1% penicillin/streptomycin (Gibco). MDA-MB-231 and OPM-2 cells were cultured in RPMI-1640 (Gibco) containing 10% FBS and 1% penicillin/streptomycin. All cells were routinely maintained in a 37° C. incubator with 5% $CO_2$.

Peptide Synthesis—

All peptides used in this study were chemically synthesized and purified by high performance liquid chromatography with >98% purity (First Base, Singapore). Their sequences are available in the Supplementary Table 1. Stock solutions were obtained by reconstituting the powder in sterile water or 50% DMSO and stored at −80° C.

Immunoblotting Analysis—

Cells were lysed in lysis buffer [50 mM Tris-HCl, (pH 7.5), 150 mM NaCl, 1% NP40, 0.5% sodium deoxycholate, Protease Inhibitor tablet (Roche)] and used for western blotting. Western blotting was carried out as previously mentioned. The primary antibodies used include anti-NPM (Invitrogen) and anti-actin (Millipore). The film of western blot was scanned, and the protein bands were quantified by the GS-800 densitometer (Bio-Rad). The protein level of NPM was quantified after normalizing with the loading control, actin.

Cell Viability and Cytotoxicity Assays—

Cells were plated in clear-bottomed white walled 96-well plates (Corning) and incubated overnight. Cells were treated with indicated peptides in 1% FBS-containing media for overnight or indicated timings at 37° C. Cell viability was measured with CellTiter-Glo reagent (Promega) according to the manufacturer's instructions. For cytotoxicity assay, cells were plated in black walled 96-well plates (Corning) to allow them to adhere overnight. Upon treatment with a pan-caspase inhibitor, z-VAD-Fmk (100 M) (Sigma) and subsequent treatment with LTV-tagged peptides, cytotoxicity induced was determined by CellTox cytotoxicity assay (Promega) 30 minutes after addition of peptides according to the manufacturer's instructions. Luminescence was determined using an Infinite 200 multiplate reader (Tecan).

Measurement of MMP—

The cationic fluorescent dye 1,1',3,3'-tetraethylbenzamidazolocarbocyanin iodide (JC-1) (Invitrogen) was utilized for MMP measurement. JC-1 was dissolved in DMSO (200 µM). Peptide-treated cells in 96-well deep sided, clear bottom, dark sided microplates were incubated with media containing JC-1 for 30 min at 37° C. and then washed twice with warm PBS. Changes in MMP were determined using a multiplate spectrofluorometer (Tecan) (excitation: 475 nm; emission: 530 nm (green); emission: 590 nm (red)). The decrease in the ratio of red to green fluorescence was used to determine relative mitochondrial depolarization.

Flow Cytometry—

MCF7 cells were plated on 6-cm culture dish to allow overnight adherence. FITC-labeled peptides (30 µM) were added to the cells, incubated for 30 min at 37° C., and subsequently washed three times with PBS. The cells were then trypsinized, collected by centrifugation, and finally resuspended in 500 µl ice-cold 2% FBS-containing PBS for flow cytometry analysis.

Immunofluorescence and Confocal Microscopy—

For staining with anti-NPM, cultured cells were fixed in 10% neutral buffered formalin (Sigma) for 10 min, and then in methanol for 10 min, washed in PBS and incubated with blocking buffer (PBS containing 0.5% bovine serum albumin) for 1 hour prior to incubation with a mouse anti-NPM antibody (Invitrogen) in blocking buffer for overnight at 4° C. Cells were then incubated with Alexa Fluor 488-conjugated secondary antibody (Jackson Immuno Research Laboratories) for 1 hour, washed three times with PBS and counterstained with 4',6-diamidino-2-phenylindole (DAPI)-containing mounting solution (Vectashield). Stained cells were examined with a LSM 510 confocal microscope using a 63× objective lens (Zeiss).

To determine the ability of FITC-labeled peptides to enter the cells and to visualize intracellular distribution of the peptides, MCF7 cells were plated on 4-chamber glass cover slides (Lab-Tek) to adhere overnight, incubated with FITC-labeled peptides (30 μM) for 30 min, and then washed three times with PBS before being fixed and mounted with DAPI-containing mounting solution (Vectashield). Images were acquired using a Nikon AIR confocal laser scanning microscope equipped with a 60× oil-immersion objective lens (SBIC-Nikon Imaging Centre).

Statistical Analysis—

All experiments were performed independently for at least three times. All statistical analyses for comparison between two groups were performed with two-tailed unpaired student's t-test using the Prism 5.01 (GraphPad Software).

What is claimed is:

1. A recombinant peptide comprising a cytotoxic peptide and an internalizing peptide, wherein the cytotoxic peptide is conjugated to the internalizing peptide, and wherein the cytotoxic peptide is represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36), wherein,
   i) each of $X_4$, $X_5$, and $X_6$ is any amino acid;
   ii) $X_7$ is histidine or leucine;
   iii) $X_8$ and $X_9$ are independently K or R or H or A; and
   iv) $X_{13}$, $X_{14}$ and $X_{15}$ are independently K or R or H;
   and, wherein the internalizing peptide is a cancer cell-targeting peptide selected from the group consisting of arginine-glycine-aspartic acid (RGD), asparagine-glycine-arginine (NGR), TCP-1 phage peptide (TCP-1) and any one of the peptides of SEQ ID Nos: 8-11, 64-789 and 795-798.

2. The recombinant peptide of claim 1, wherein
   v) $X_8$ and $X_9$ are the same, and are K or R or H or A; and
   vi) $X_{13}$, $X_{14}$ and $X_{15}$ are the same, and are K or R or H.

3. The recombinant peptide of claim 1, wherein the amino acid sequence of the cytotoxic peptide is selected from the group consisting of: i) QLGKKKHRRRPSKKKRHW (SEQ ID NO: 3), ii) QLGRRRHRRRPSRRRRHW (SEQ ID NO: 4), iii) QLGKKILAARPSKKKRHW (SEQ ID NO: 5), and iv) QLGAAAHRRRPSKKKRHW (SEQ ID NO: 38).

4. A peptide conjugate comprising a cytotoxic peptide and a nanoparticle or a microparticle, wherein the cytotoxic peptide is conjugated to the nanoparticle or microparticle, and wherein the cytotoxic peptide is represented by the consensus sequence $Q_1$-$L_2$-$G_3$-$X_4$-$X_5$-$X_6$-$X_7$-$X_8$-$X_9$-$R_{10}$-$P_{11}$-$S_{12}$-$X_{13}$-$X_{14}$-$X_{15}$-$R_{16}$-$H_{17}$-$W_{18}$ (SEQ ID NO: 36),
   wherein,
   i) each of $X_4$, $X_5$, and $X_6$ is any amino acid;
   ii) $X_7$ is histidine or leucine;
   iii) $X_8$ and $X_9$ are independently K or R or H or A; and
   iv) $X_{13}$, $X_{14}$ and $X_{15}$ are independently K or R or H.

5. The peptide conjugate of claim 4, wherein
   v) $X_8$ and $X_9$ are the same, and are K or R or H or A; and
   vi) $X_{13}$, $X_{14}$ and $X_{15}$ are the same, and are K or R or H.

6. The peptide conjugate of claim 4, wherein the amino acid sequence of the cytotoxic peptide is selected from the group consisting of: i) QLGKKKHRRRPSKKKRHW (SEQ ID NO: 3), ii) QLGRRRHRRRPSRRRRHW (SEQ ID NO: 4), iii) QLGKKILAARPSKKKRHW (SEQ ID NO: 5), and iv) QLGAAAHRRRPSKKKRHW (SEQ ID NO: 38).

7. The peptide conjugate of claim 4, wherein the nanoparticle or microparticle is made from a material selected from the group consisting of metal, silica, carbon, polymeric materials, and mixtures thereof.

8. The recombinant peptide of claim 1, wherein the peptide has a modification selected from the group consisting of glycosylation, sulfation, phosphorylation, ubiquitination, methylation, lipidation, biotinylation, hydroxylation and acetylation.

9. The recombinant peptide of claim 1, comprising the peptide of SEQ ID NO: 15.

* * * * *